US011865164B2

(12) United States Patent
Choe et al.

(10) Patent No.: US 11,865,164 B2
(45) Date of Patent: Jan. 9, 2024

(54) PHARMACEUTICAL COMPOSITION FOR TREATING CANCER, CONTAINING GUIDE RNA AND ENDONUCLEASE AS ACTIVE INGREDIENTS

(71) Applicant: G+FLAS LIFE SCIENCES, Seoul (KR)

(72) Inventors: Sunghwa Choe, Seoul (KR); Mi Jin Park, Seoul (KR); Aiden Yeonghoon Park, Seoul (KR); Jung Hak Lim, Seoul (KR); Dong Wook Kim, Seoul (KR); Sungyong In, Seoul (KR); Jongjin Park, West Lafayette, IN (US)

(73) Assignee: G+FLAS LIFE SCIENCES, Seoul (KR)

( * ) Notice: Subject to any disclaimer, the term of this patent is extended or adjusted under 35 U.S.C. 154(b) by 461 days.

(21) Appl. No.: 17/041,670

(22) PCT Filed: Mar. 27, 2019

(86) PCT No.: PCT/KR2019/003585
§ 371 (c)(1),
(2) Date: Sep. 25, 2020

(87) PCT Pub. No.: WO2019/190198
PCT Pub. Date: Oct. 3, 2019

(65) Prior Publication Data
US 2021/0128697 A1      May 6, 2021

(30) Foreign Application Priority Data
Mar. 27, 2018   (KR) .................... 10-2018-0035298

(51) Int. Cl.
| A61K 48/00 | (2006.01) |
| A61K 38/46 | (2006.01) |
| A61K 47/64 | (2017.01) |
| A61P 35/00 | (2006.01) |
| A61K 31/7105 | (2006.01) |

(52) U.S. Cl.
CPC ........ *A61K 38/465* (2013.01); *A61K 31/7105* (2013.01); *A61K 47/64* (2017.08); *A61P 35/00* (2018.01)

(58) Field of Classification Search
CPC ......... A61K 38/465; A61K 48/00; C12N 9/52
See application file for complete search history.

(56) References Cited

U.S. PATENT DOCUMENTS

| 10,240,145 B2 * | 3/2019 | Tang ..................... C12N 9/22 |
| 2016/0186152 A1 | 6/2016 | Brouns et al. |
| 2017/0114413 A1 | 4/2017 | Hahn et al. |
| 2017/0145405 A1 * | 5/2017 | Tang ................... A61K 38/465 |
| 2017/0247690 A1 | 8/2017 | Quake et al. |
| 2018/0237771 A1 | 8/2018 | Kim et al. |

FOREIGN PATENT DOCUMENTS

| KR | 10-2018-0020125 A | 2/2018 |
| KR | 10-2018-0020929 A | 2/2018 |
| WO | 2016/160721 A1 | 10/2016 |
| WO | 2018/009525 A1 | 1/2018 |

OTHER PUBLICATIONS

Clements, "Rice CRISPR: Rapidly Increased Cut Ends by an Exonuclease Cas9 Fusion in Zebrafish", Genesis, vol. 55, No. 8, Aug. 2017, pp. 1-11.
Taeyoung Koo et al., "Selective disruption of an oncogenic mutant allele by CRISPR/Cas9 induces efficient tumor regression", Nucleic Acids Research, 2017, pp. 7897-7908, vol. 45, No. 13.
Euna Lee, G+FLAS Challenges Anti-Cancer Drug Based on 'CRISPR Plus' Technology, BioSpectator, Aug. 16, 2018.
Korean Notice of Preliminary Examination Result for KR 10-2019-0035288.
International Search Report for PCT/KR2019/003585 dated Jul. 5, 2019 [PCT/ISA/210].

* cited by examiner

*Primary Examiner* — Tekchand Saidha
(74) *Attorney, Agent, or Firm* — Sughrue Mion, PLLC

(57) ABSTRACT

A pharmaceutical composition for treating cancer, containing a crRNA and an endonuclease as active ingredients is disclosed. The composition can be customized according to the needs of patients or cell types by specifically treating cancer cells on the basis of specific binding properties of DNA and RNA. The nuclease activity of a CRISPR PLUS system, containing both an endonuclease and an exonuclease can be activated by means of the binding between crRNA and a gene specifically found in cancer cells. Therefore, the cancer treatment effect of the composition is more specific than that of other anti-cancer agents that have been developed up till now.

6 Claims, 33 Drawing Sheets

Specification includes a Sequence Listing.

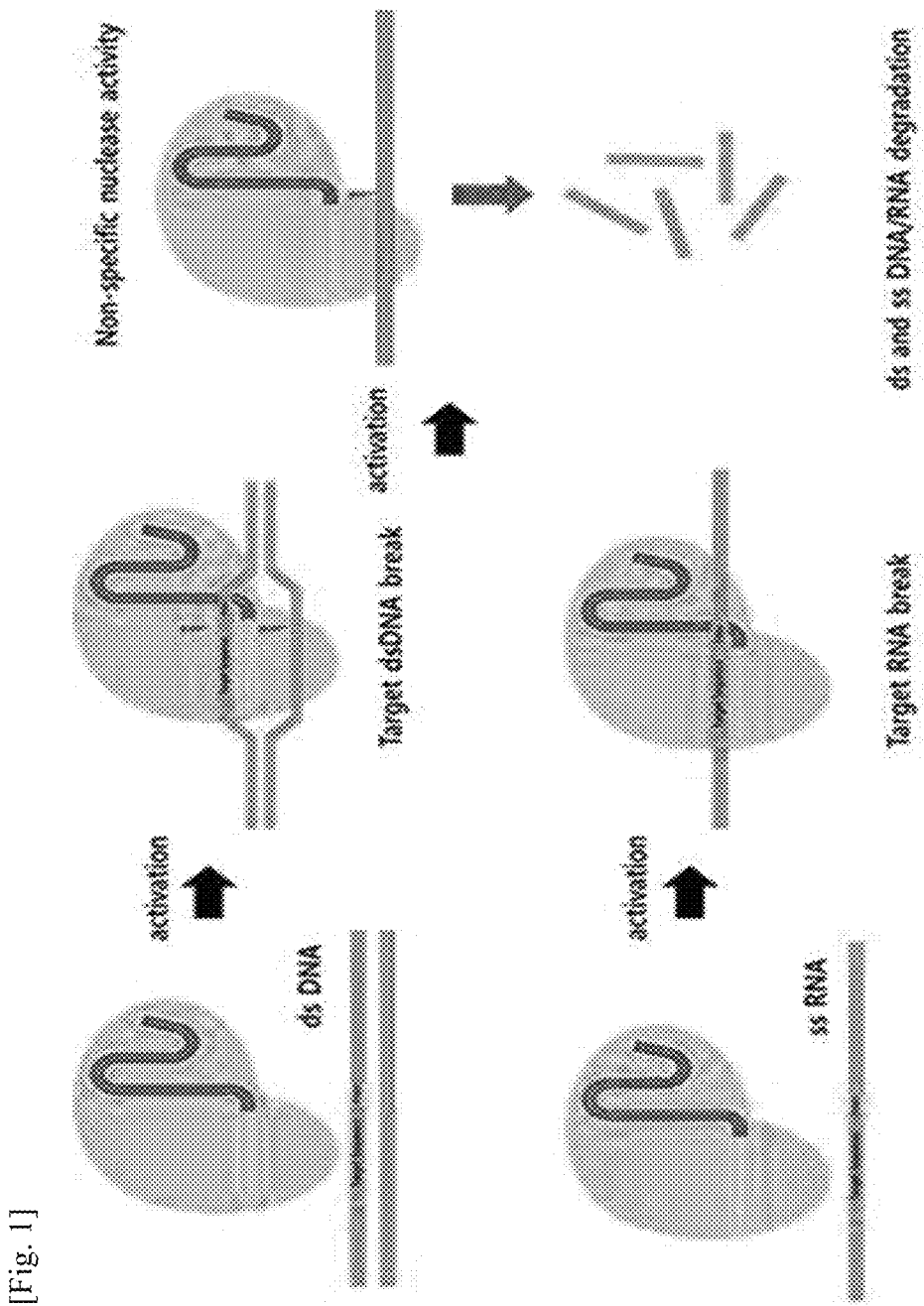
[Fig. 1]

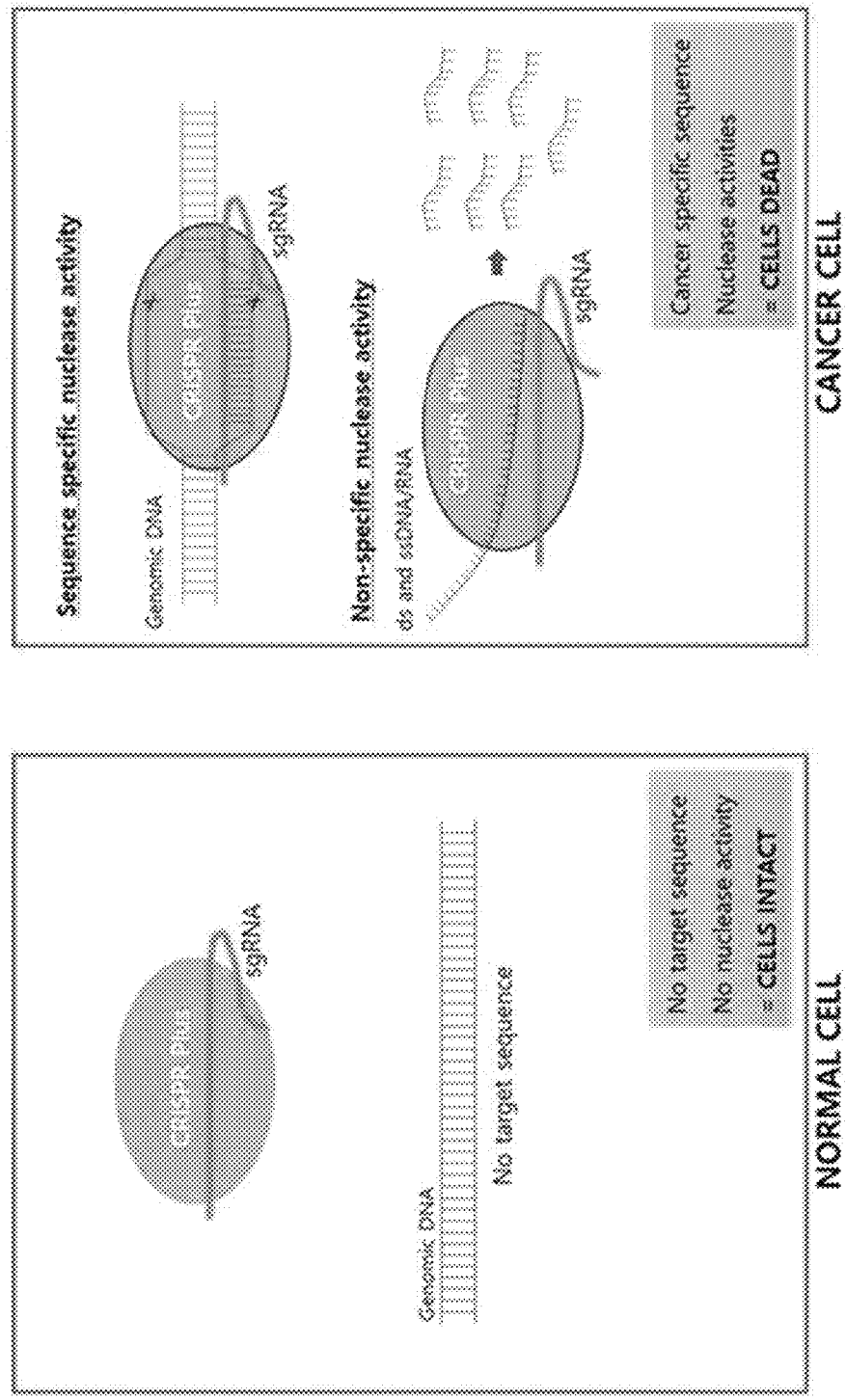
[Fig. 2]

[Fig. 3]
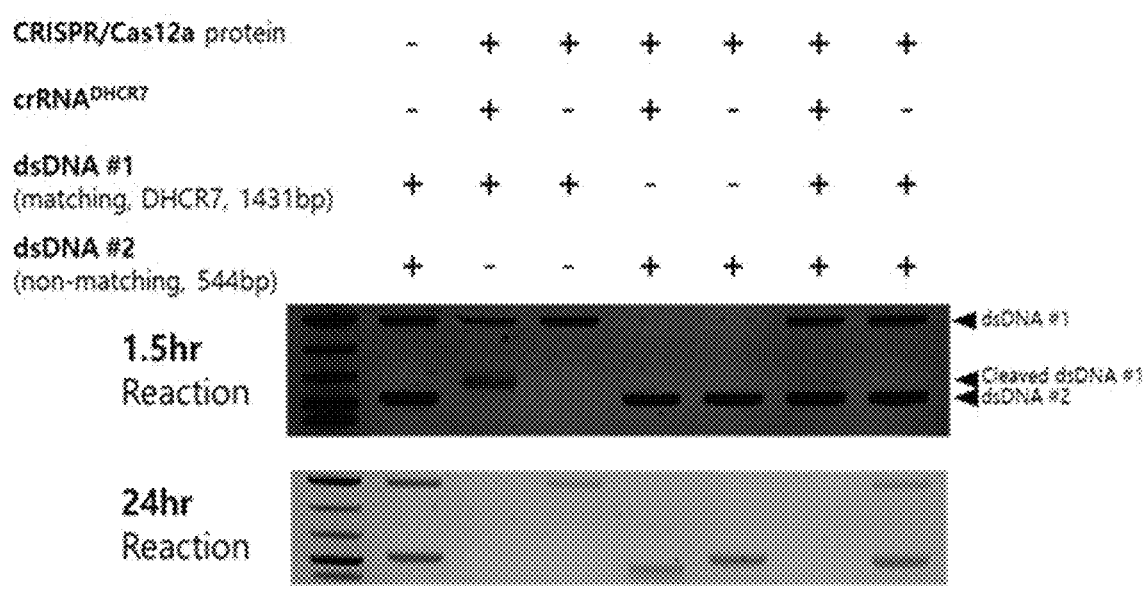

[Fig. 4a]
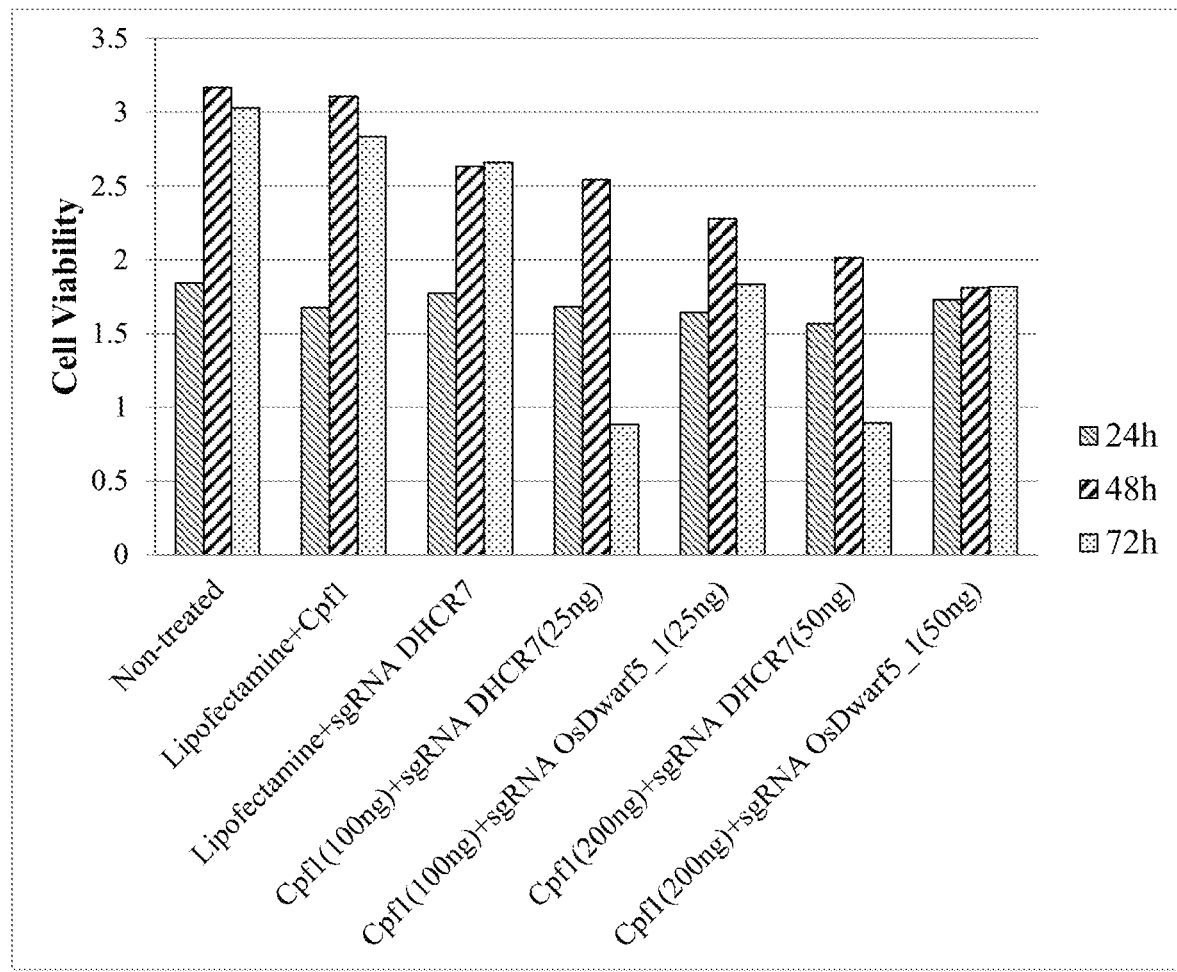

[Fig. 4b]
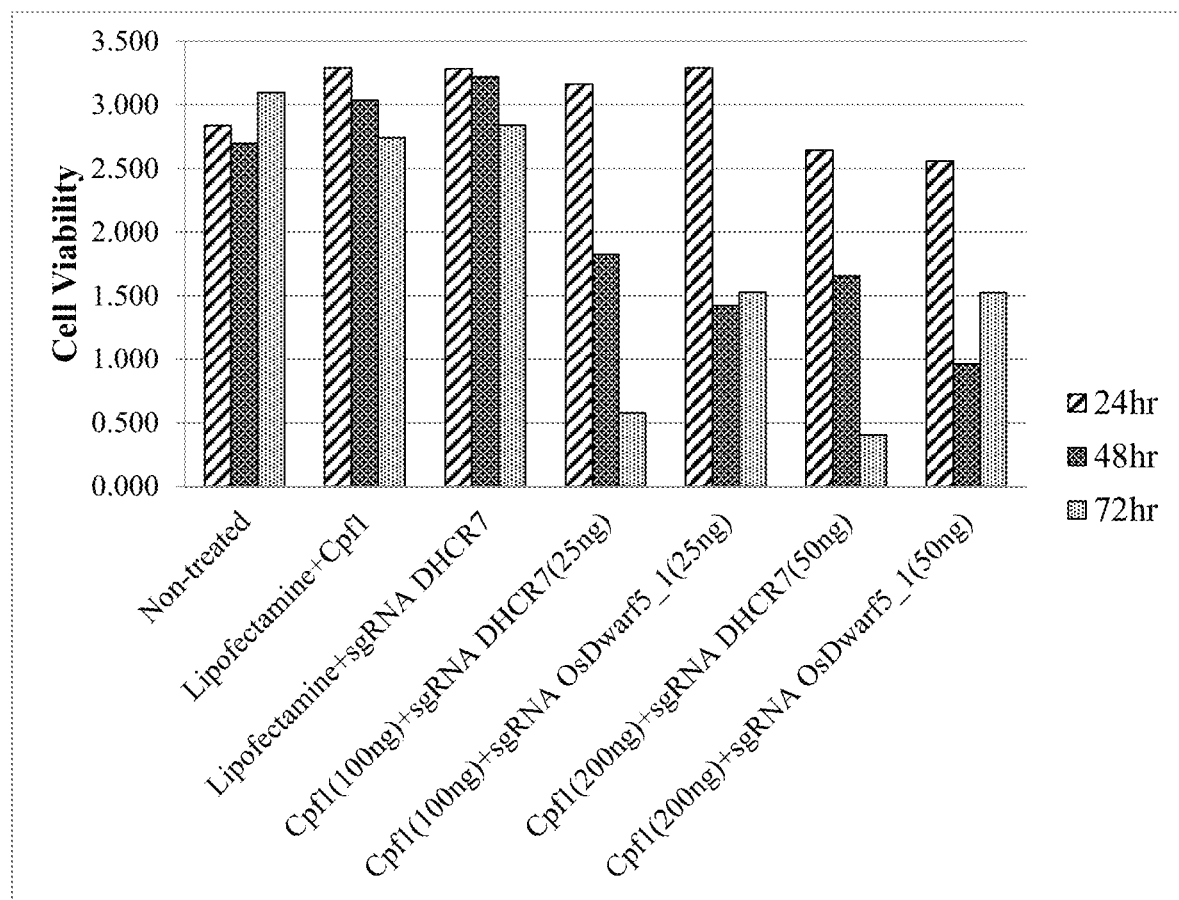

[Fig. 5]
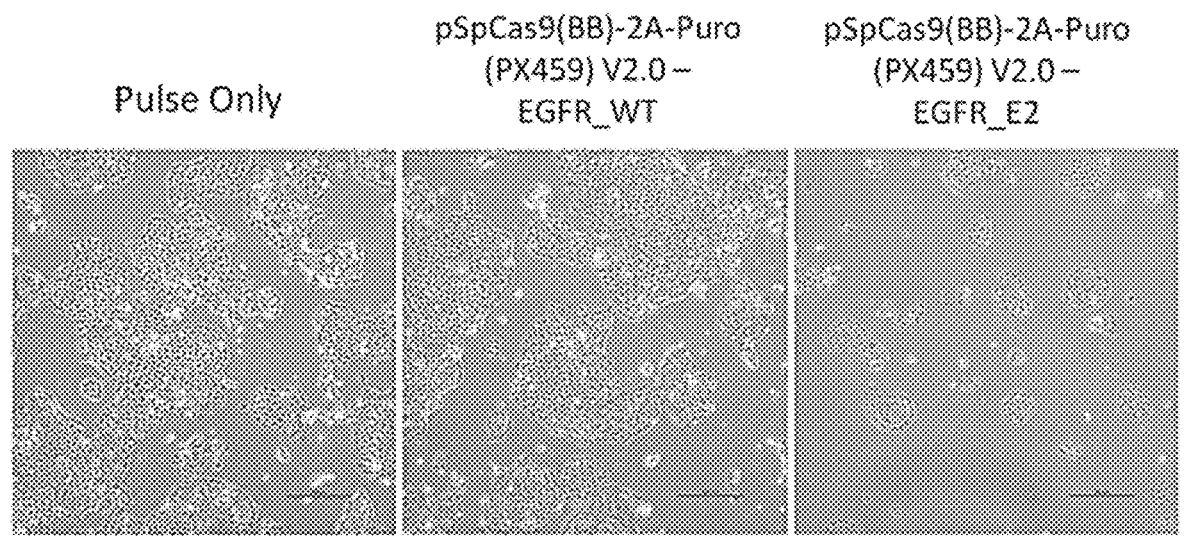
[Fig. 6]
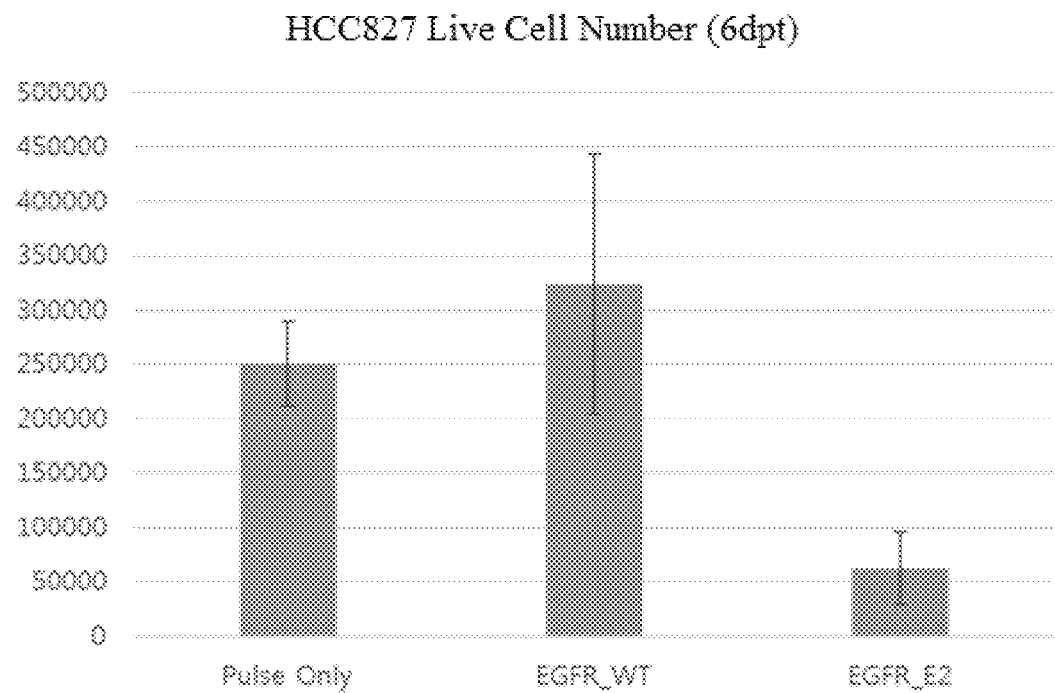

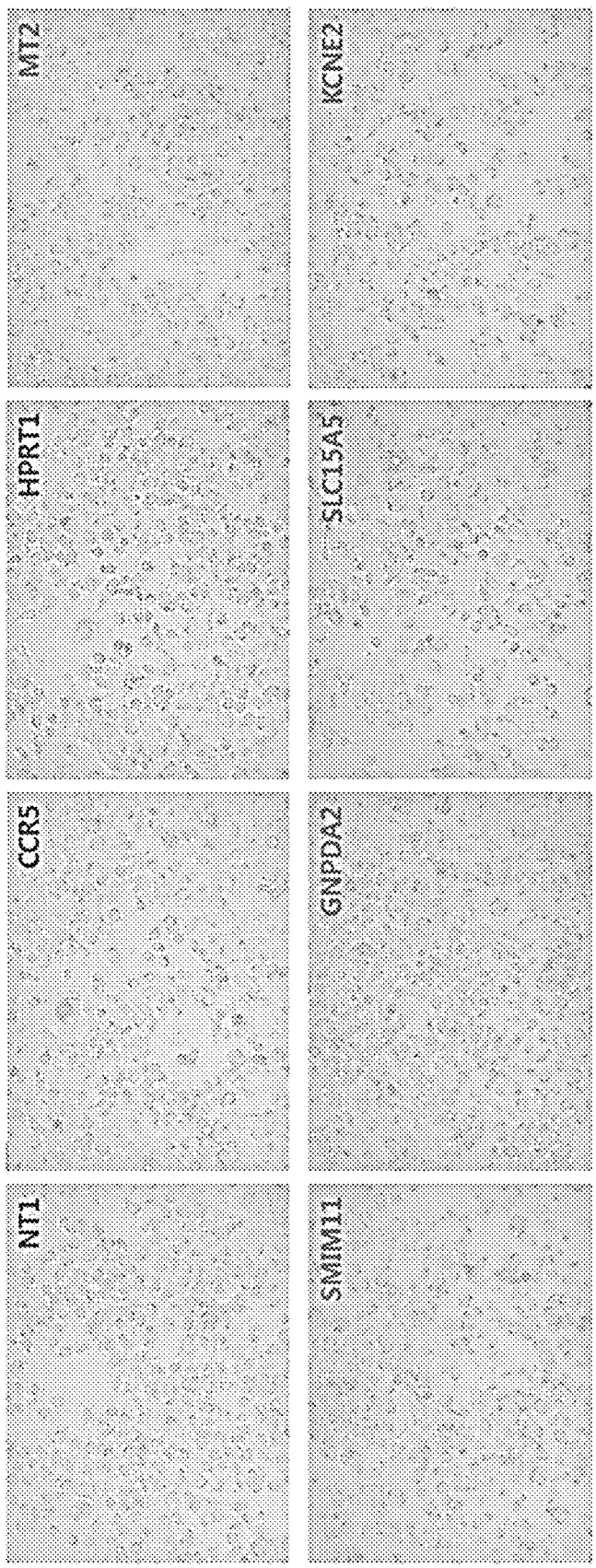
[Fig. 7]

[Fig. 8]
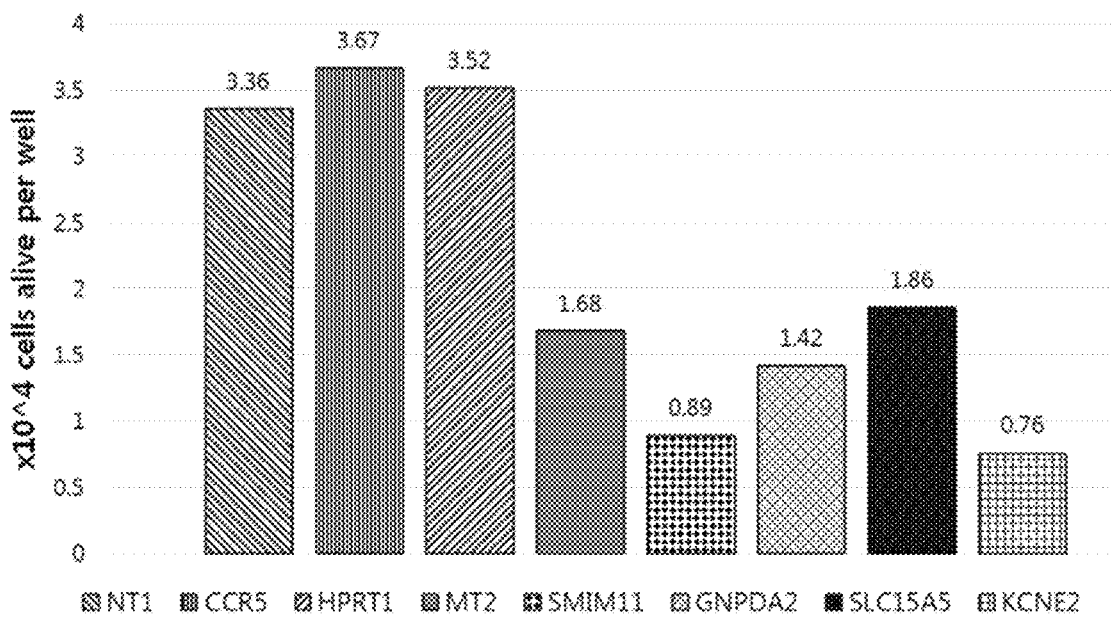
[Fig. 9]
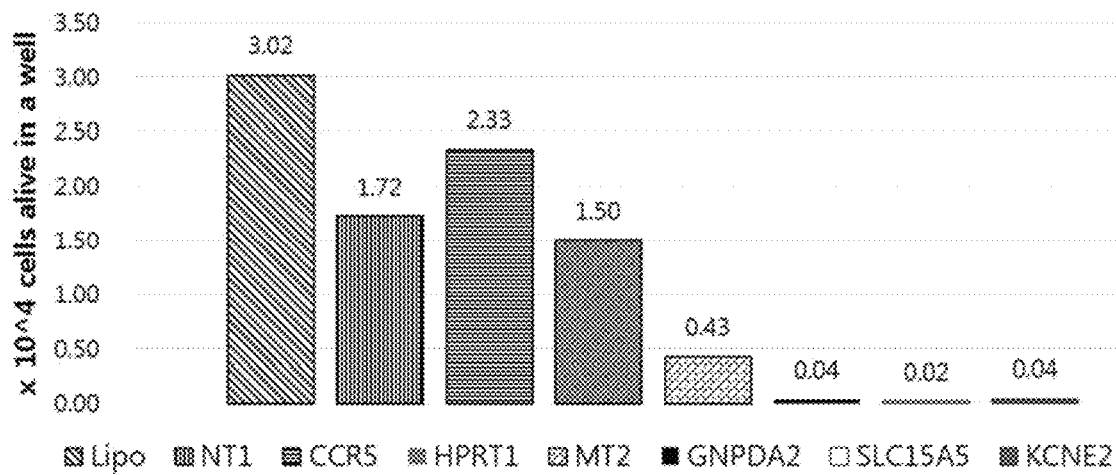

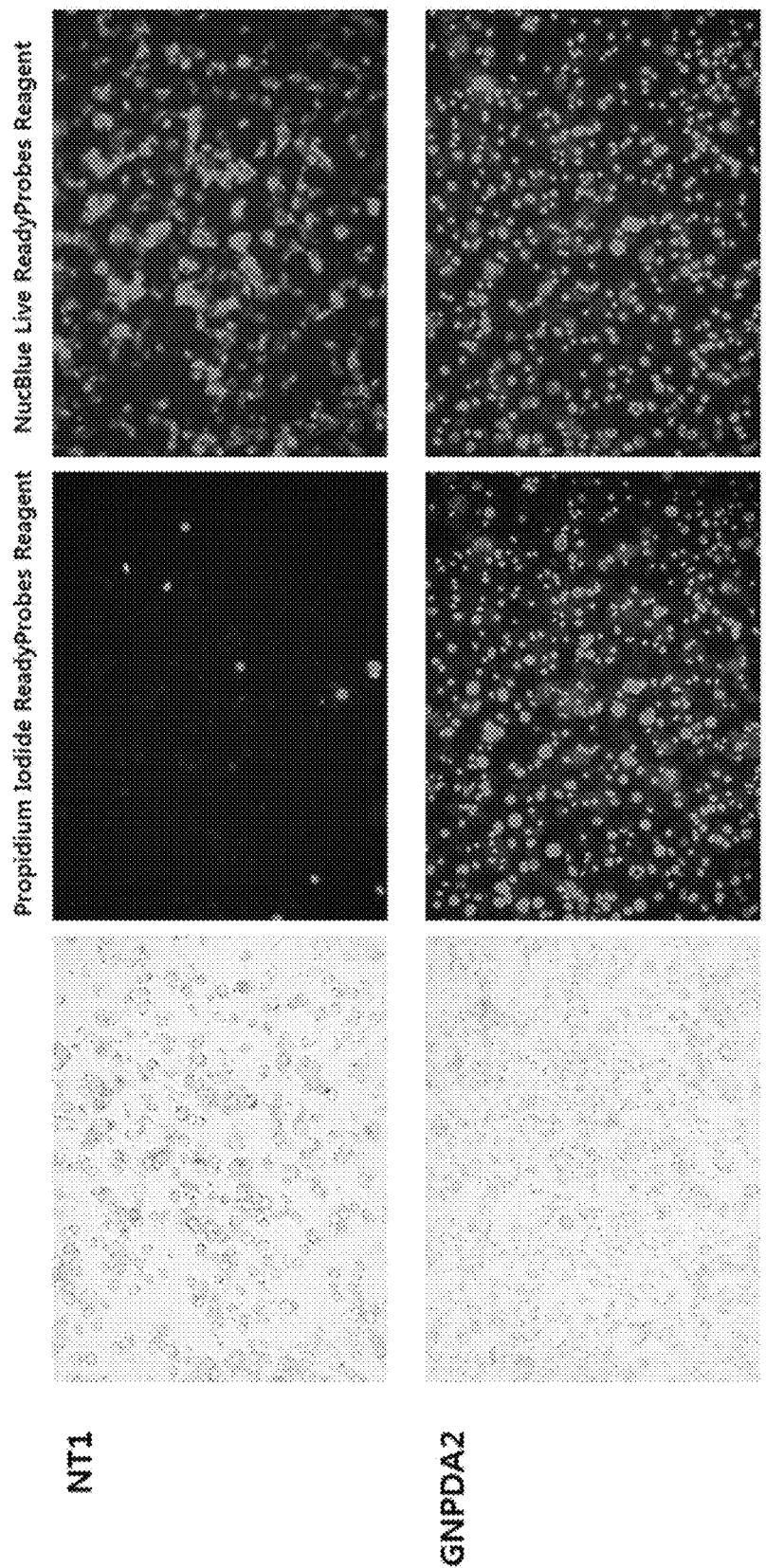
[Fig. 10]

[Fig. 11]
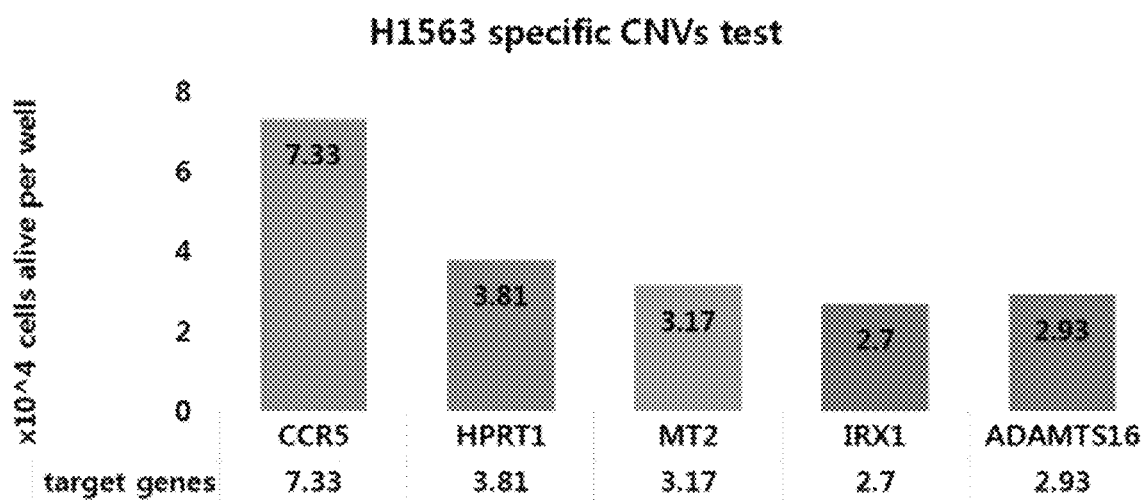

[Fig. 12]
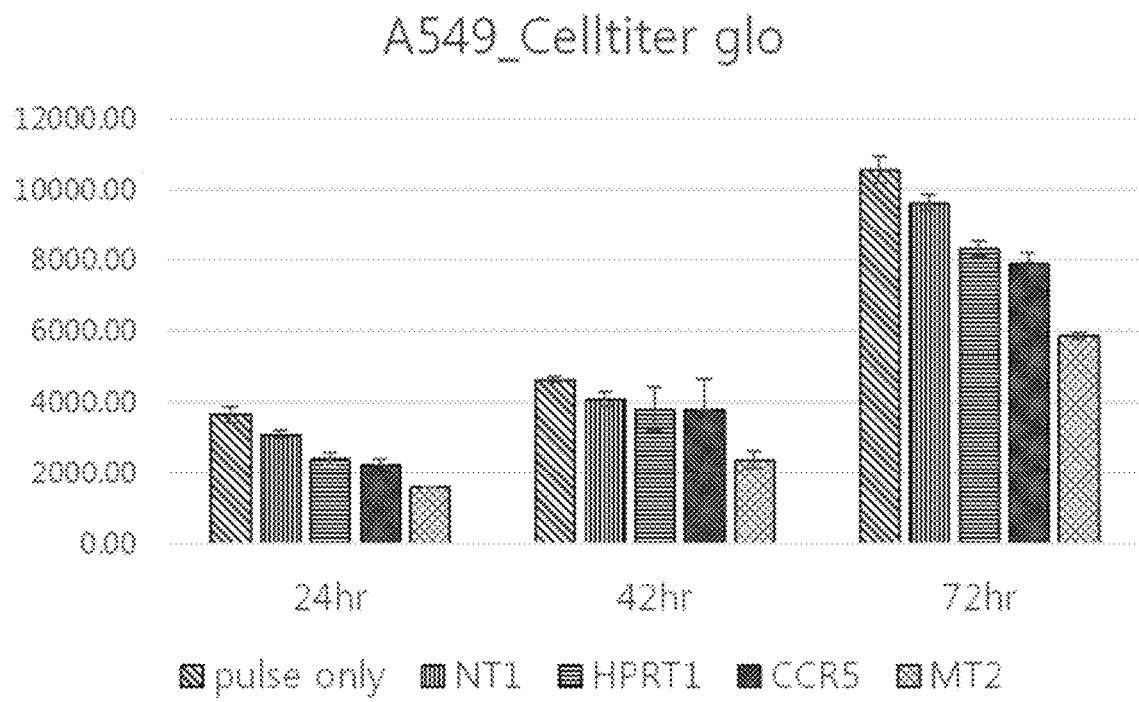

[Fig. 13]
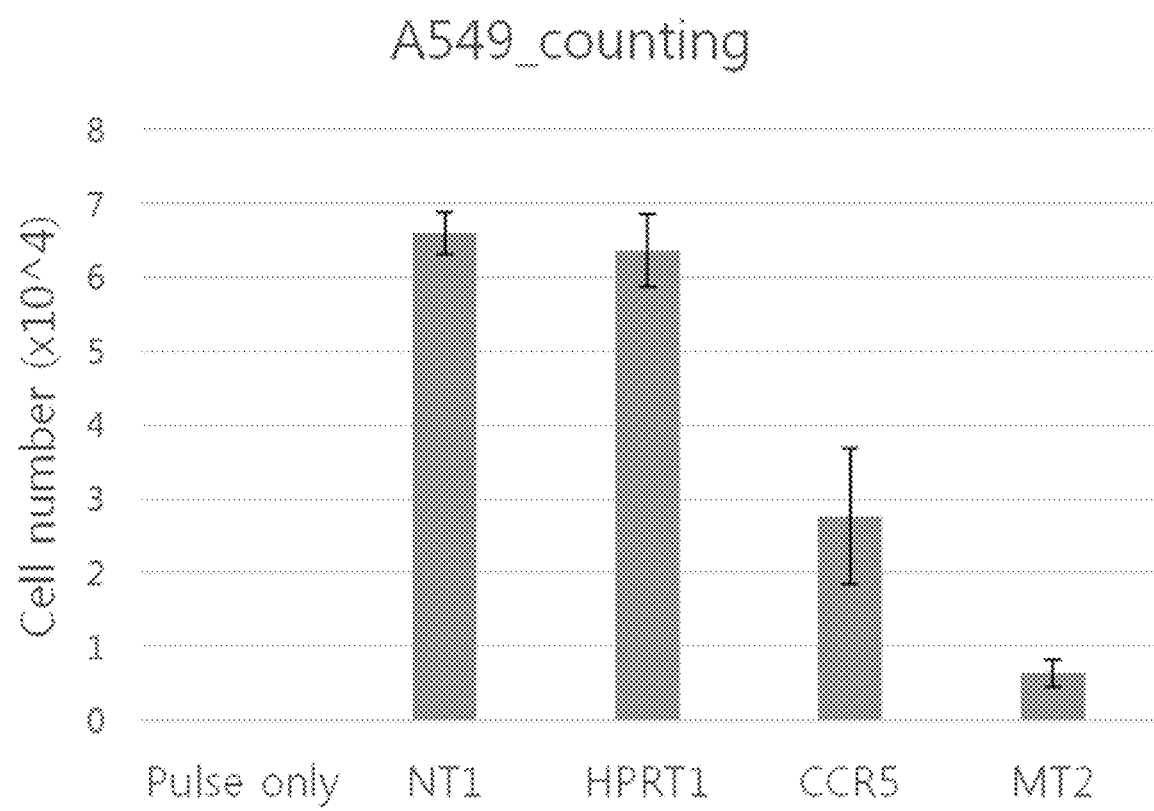

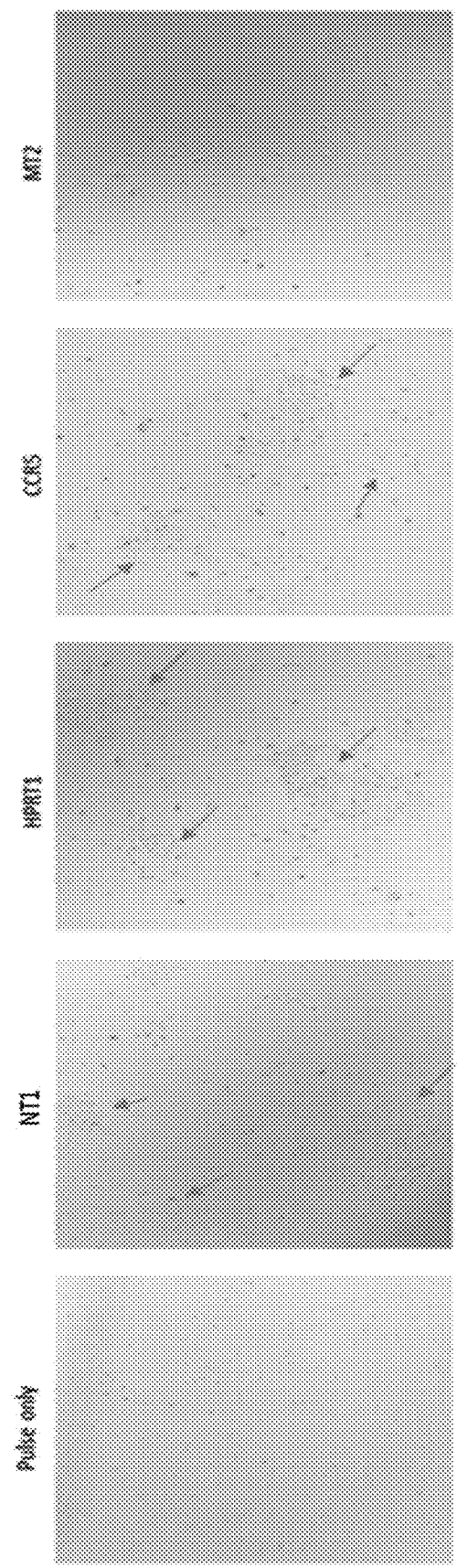
[Fig. 14]

[Fig. 15]
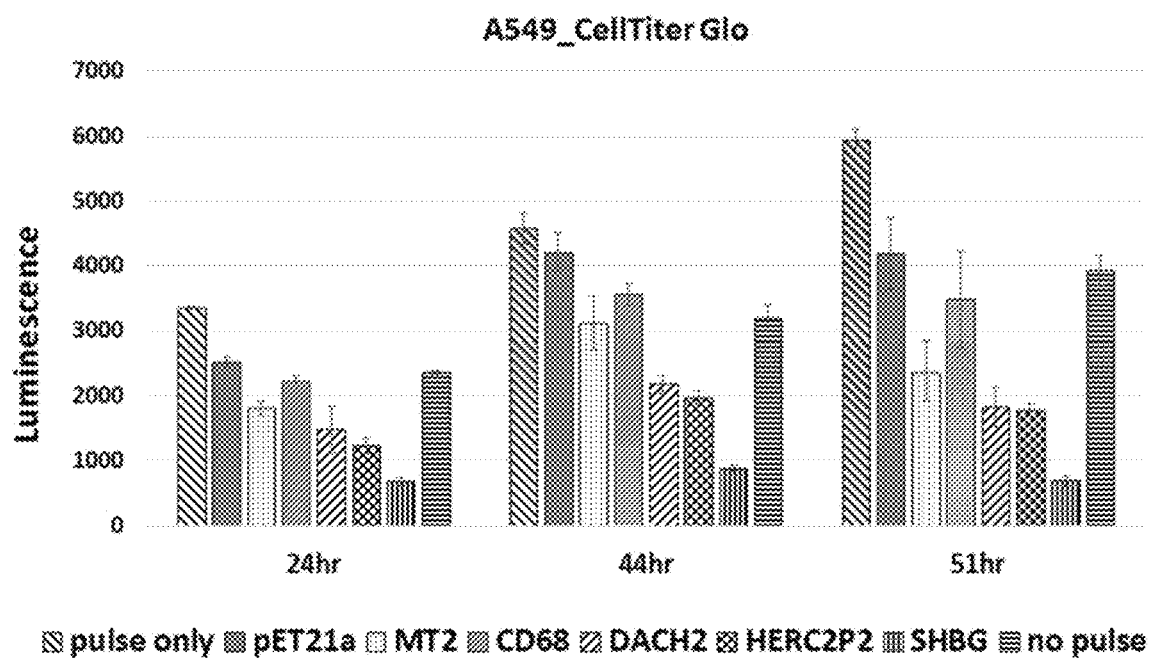

[Fig. 16]
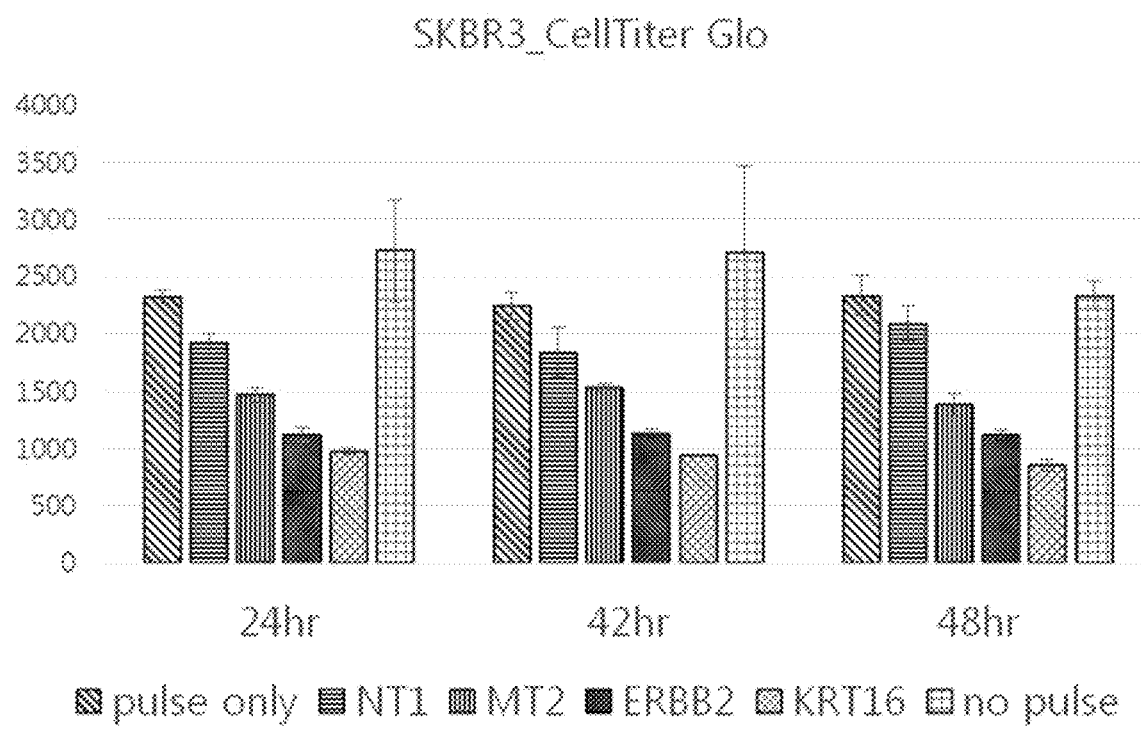

[Fig. 17]
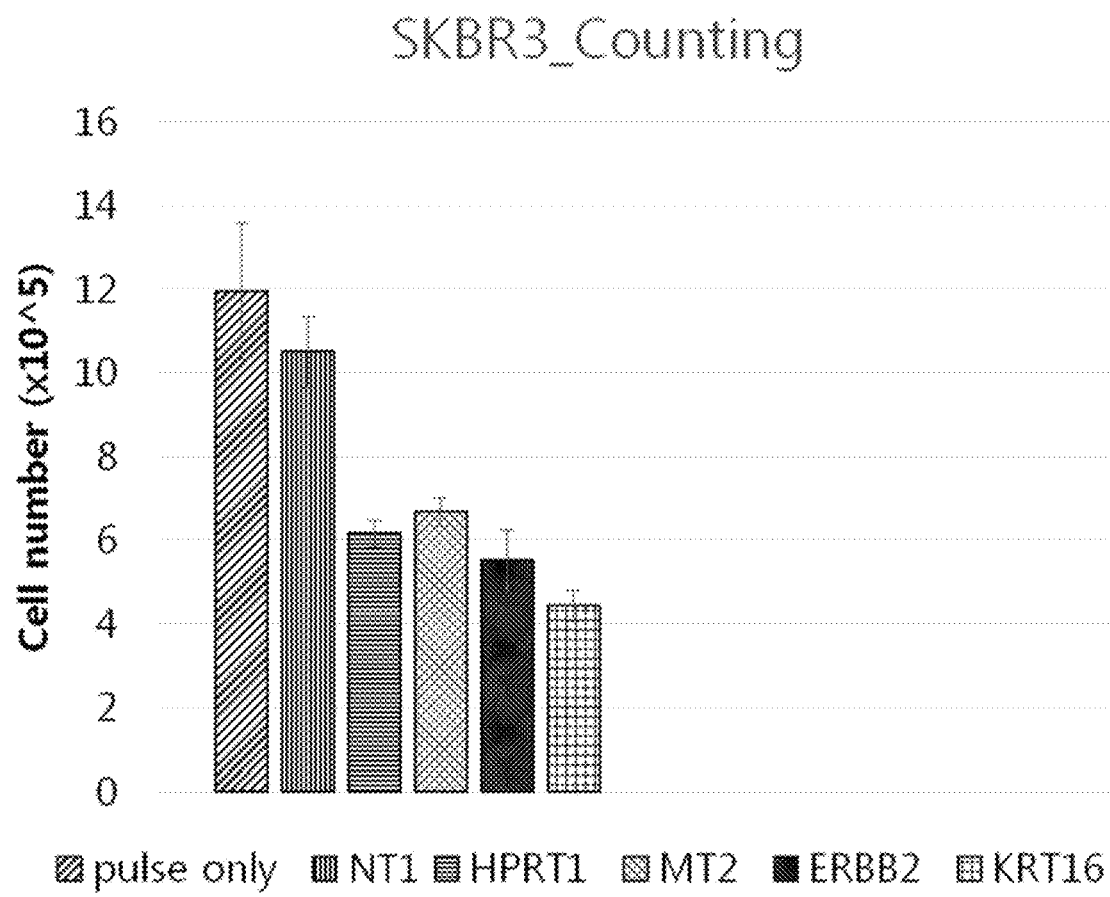

[Fig. 18]
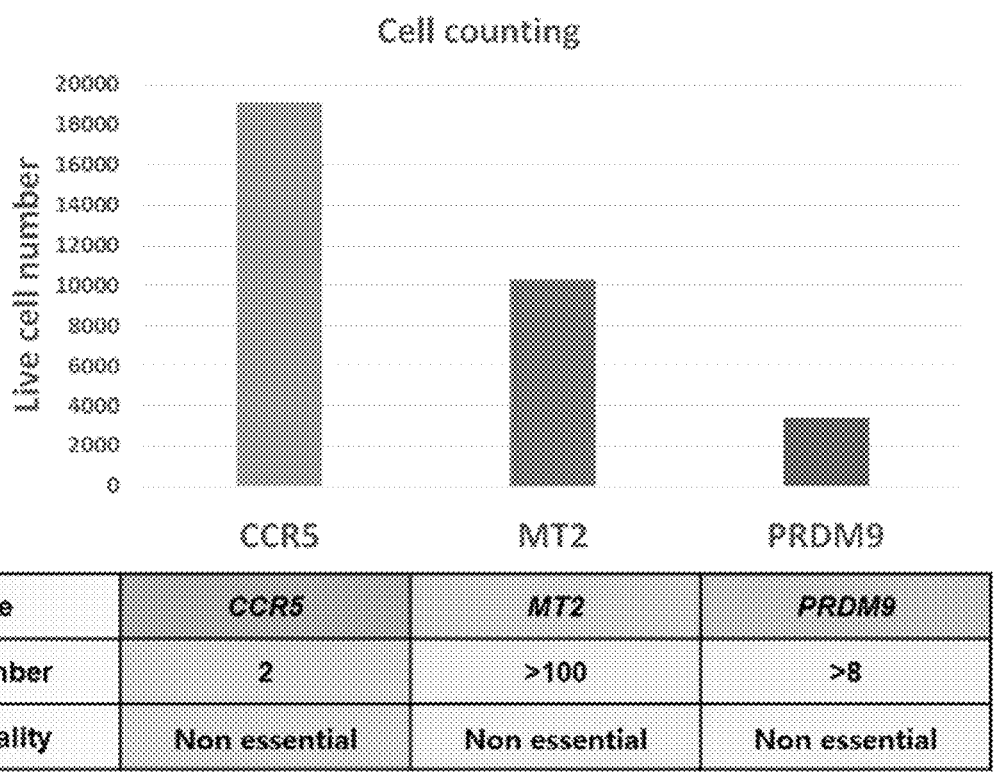

[Fig. 19]
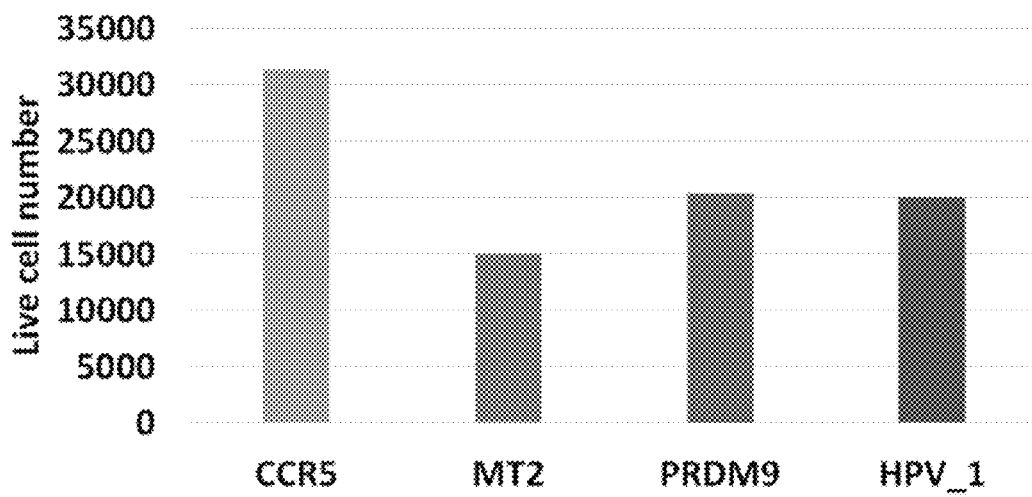

[Fig. 20a]
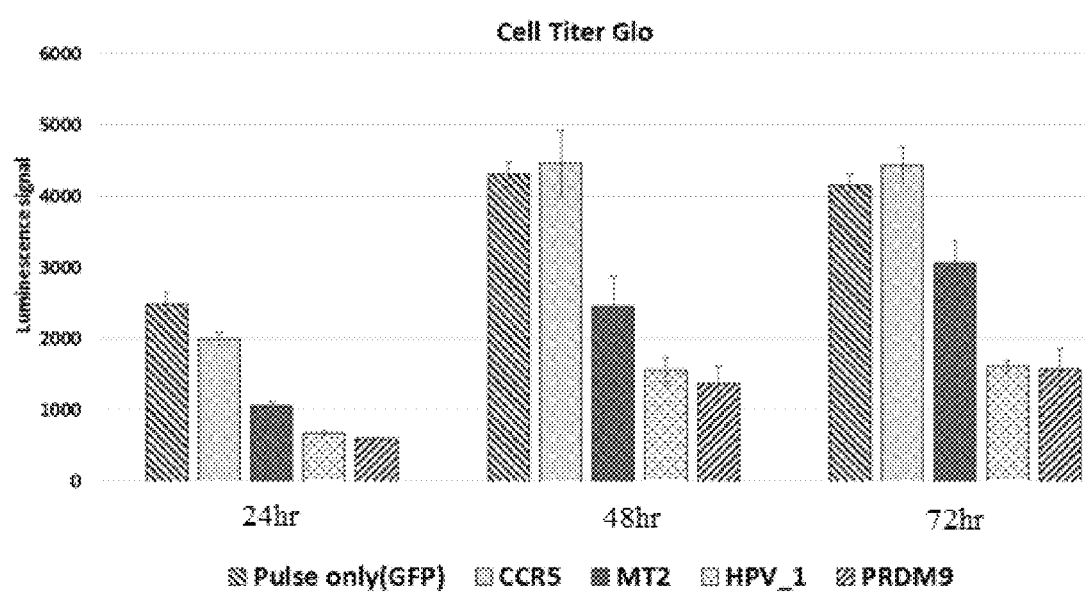

[Fig. 20b]
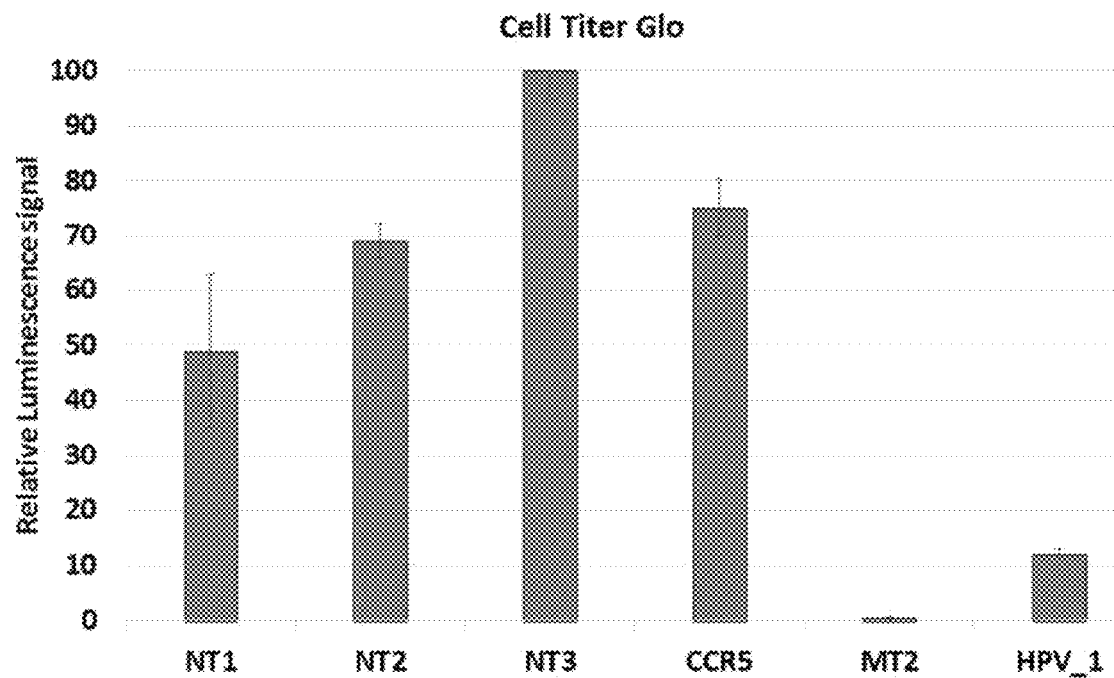

[Fig. 21]
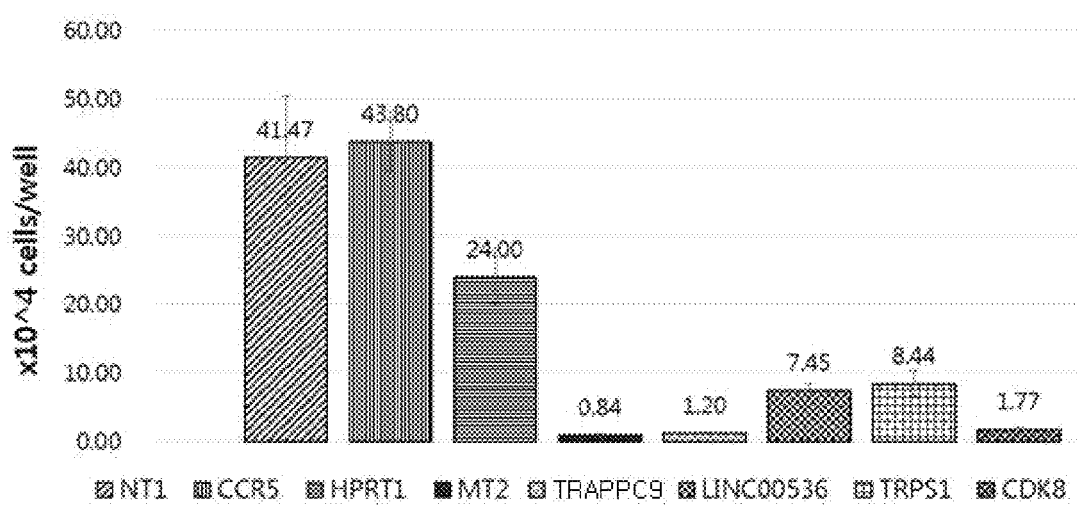

[Fig. 22]
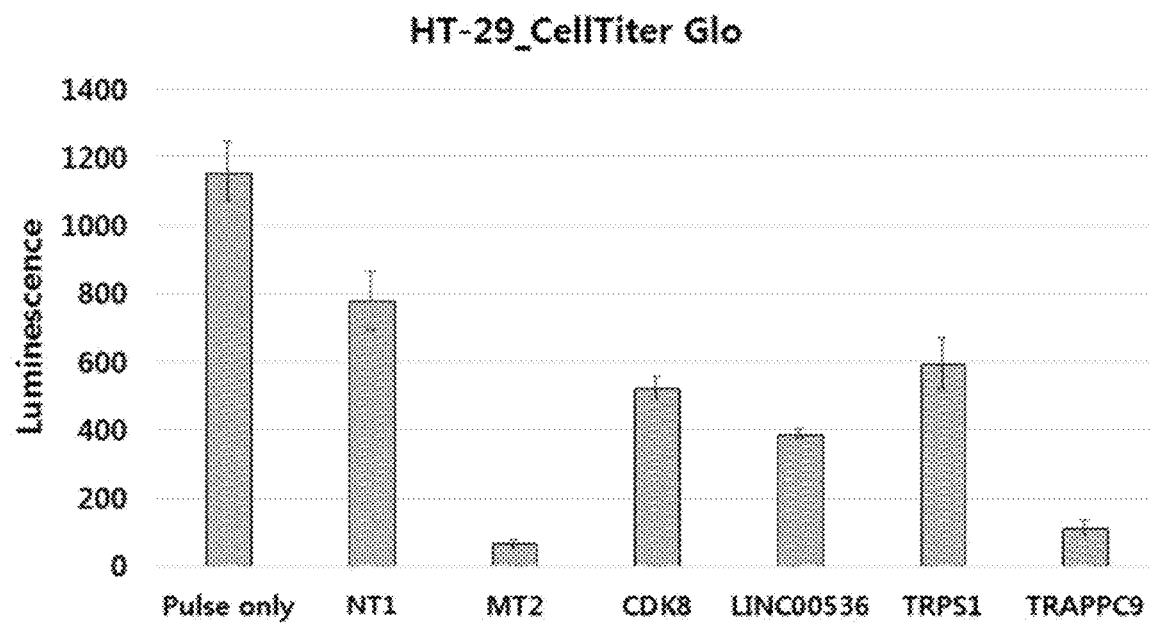

[Fig. 23]
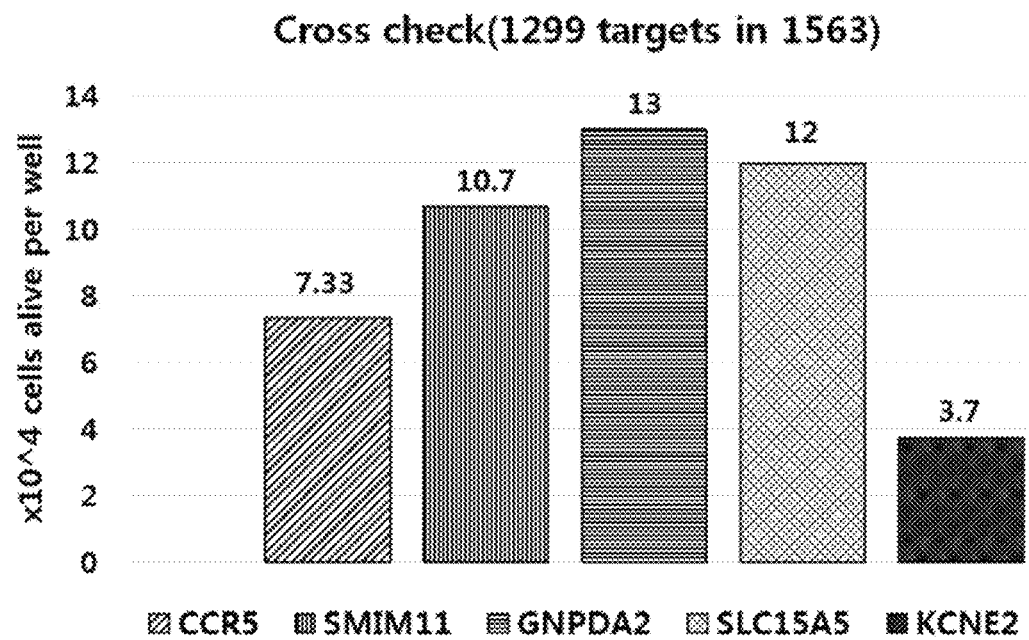

[Fig. 24]
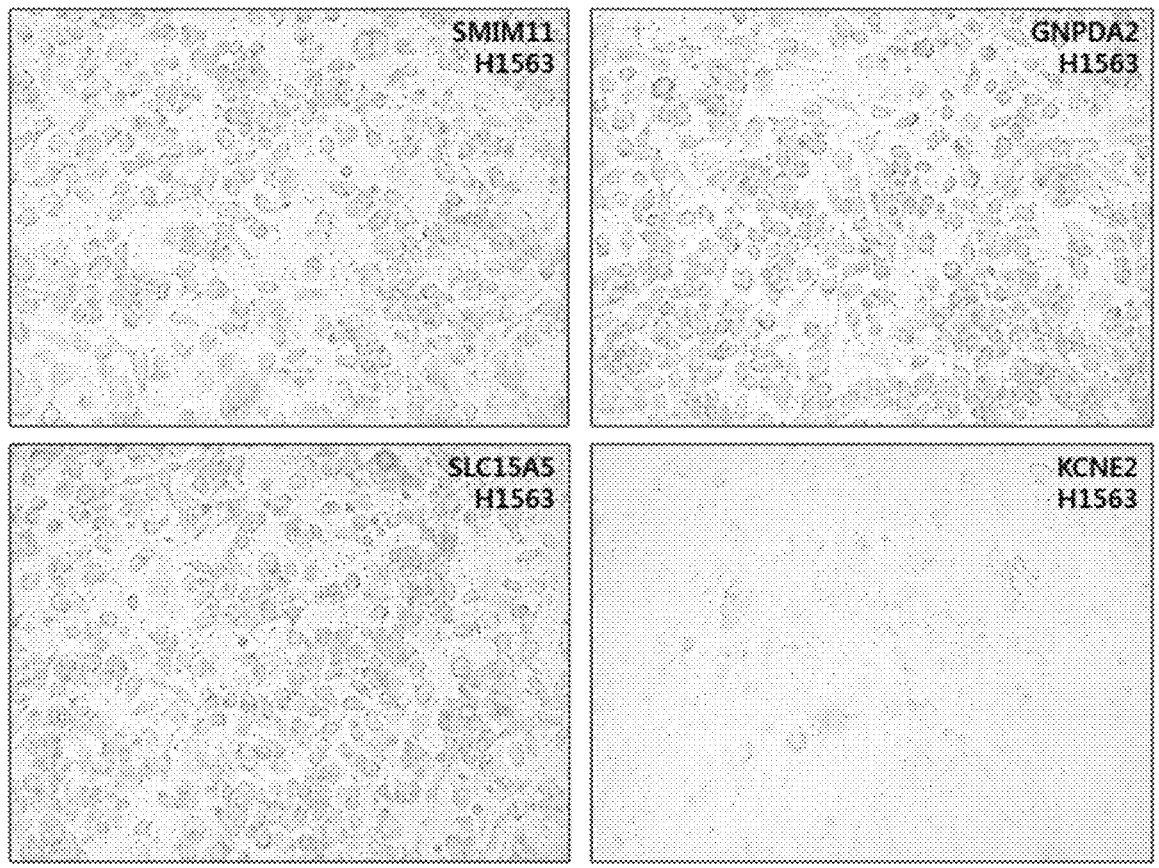

[Fig. 25]
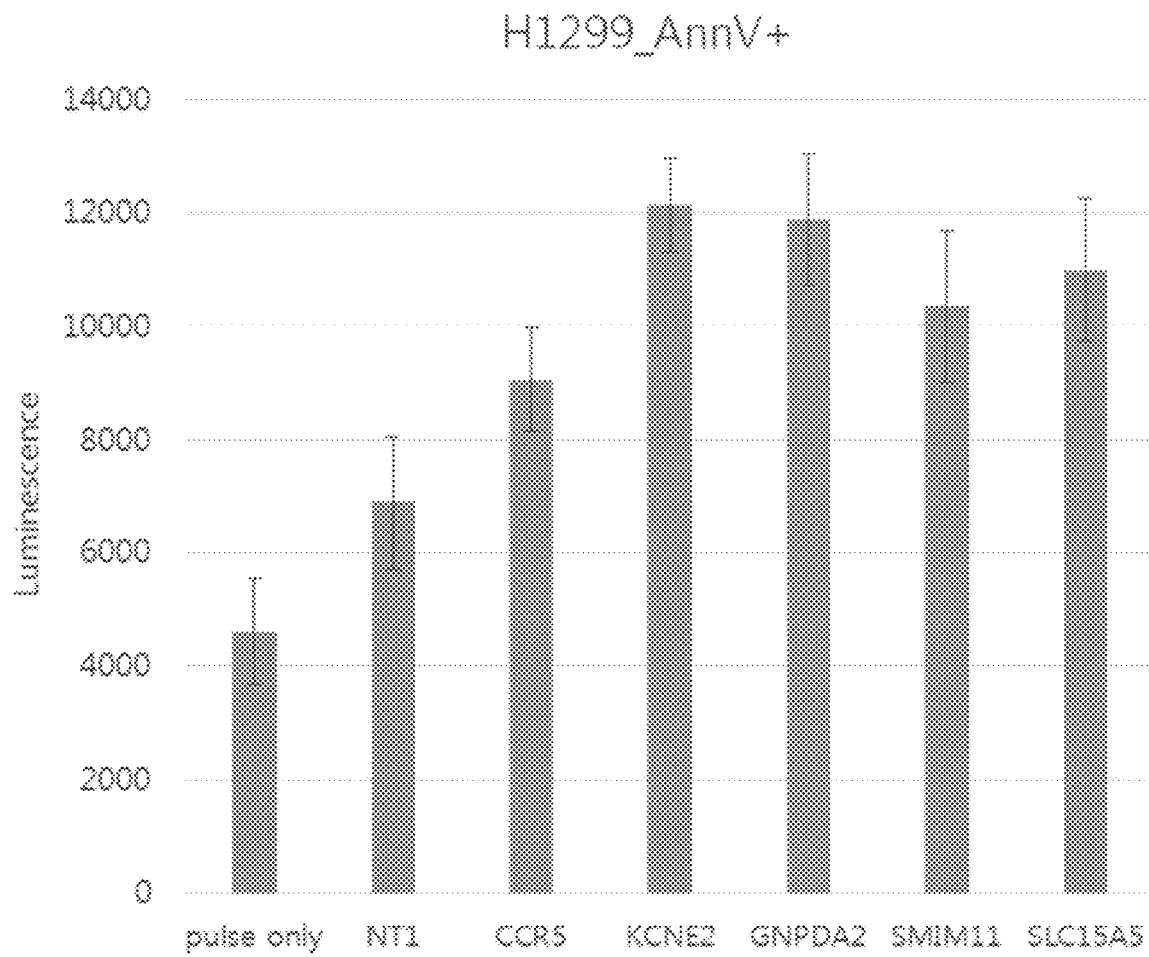

[Fig. 26]
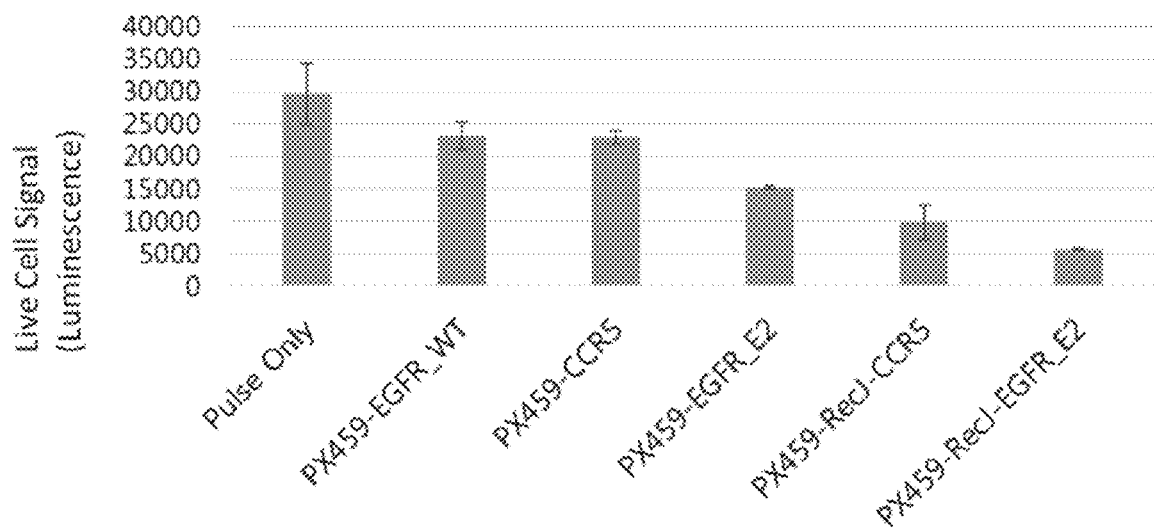

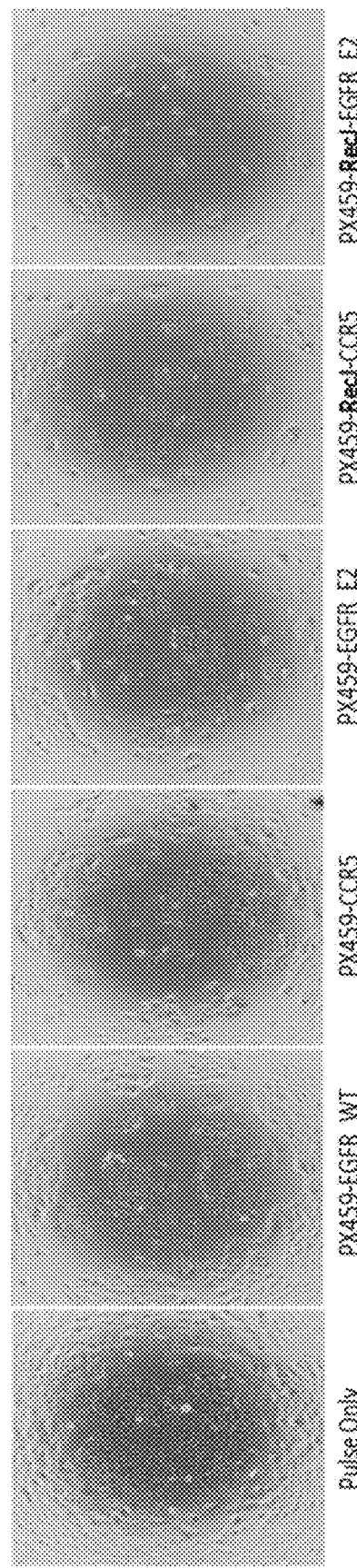
[Fig. 27]

[Fig. 28]
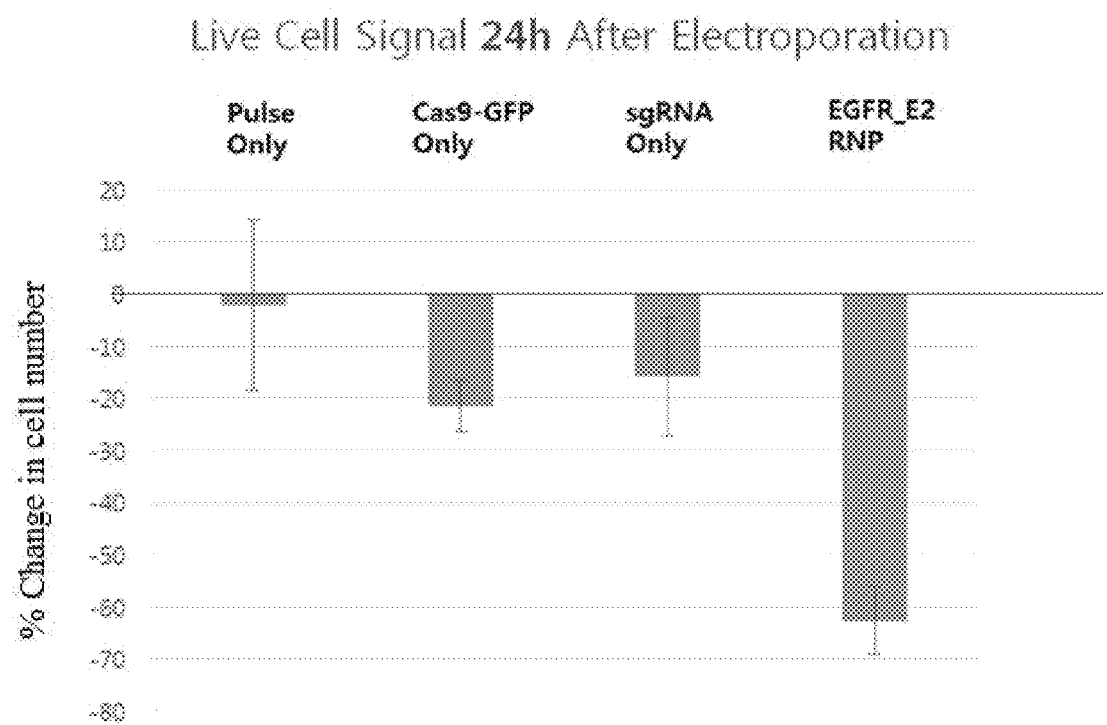

[Fig. 29]

[Fig. 30]
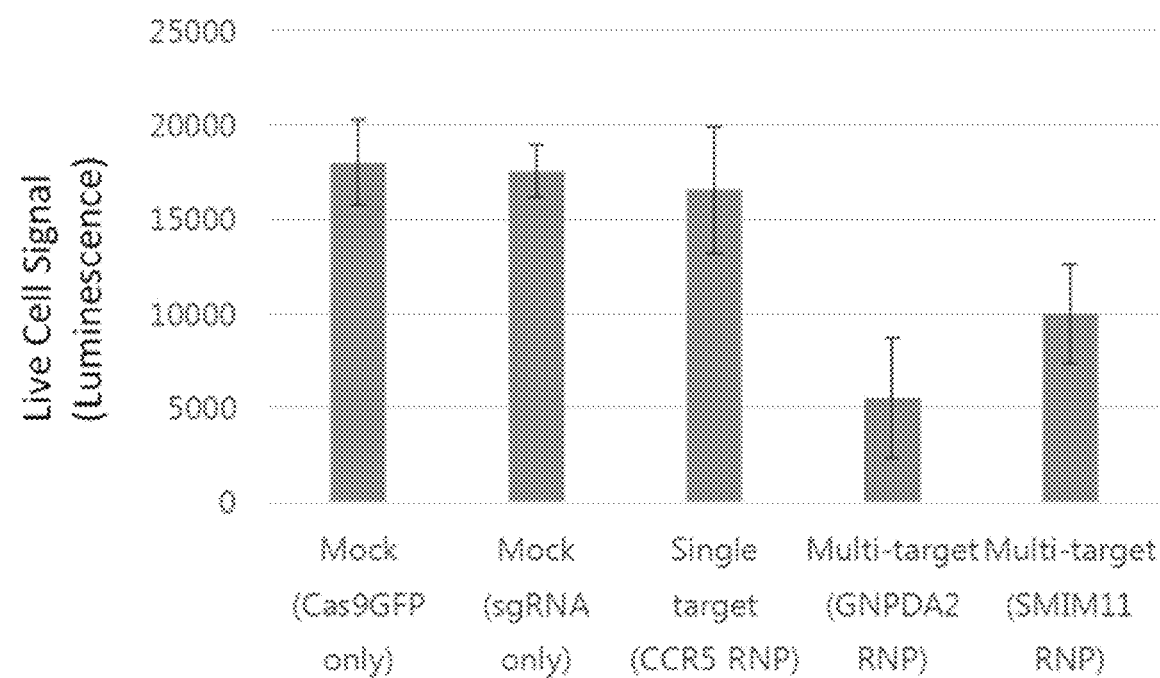

[Fig. 31]
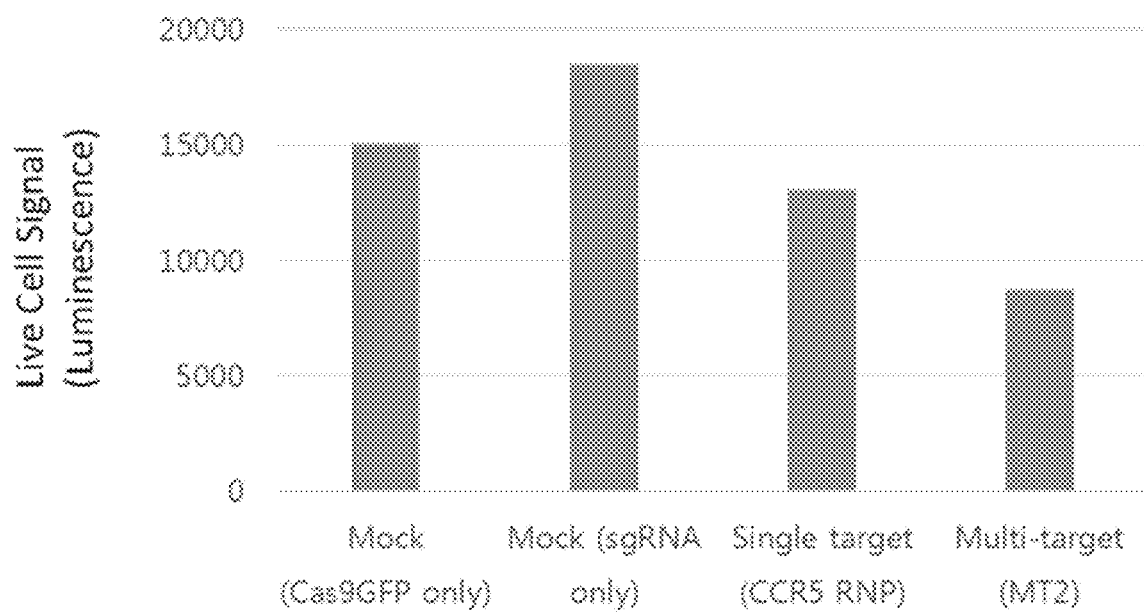

[Fig. 32]
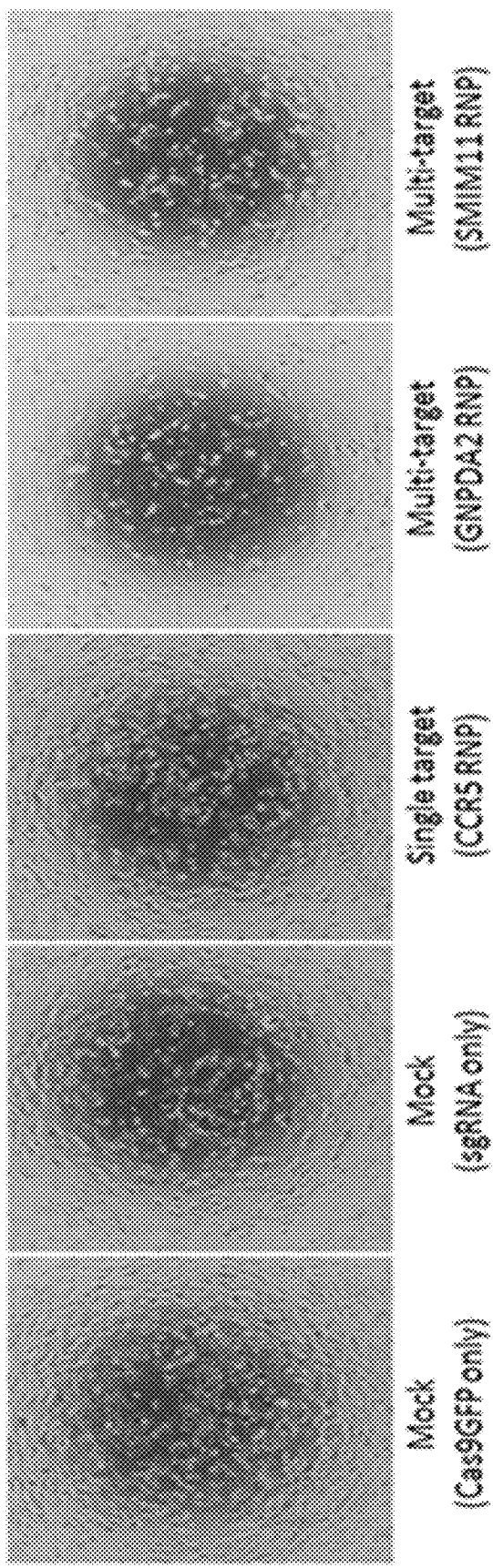

[Fig. 33]
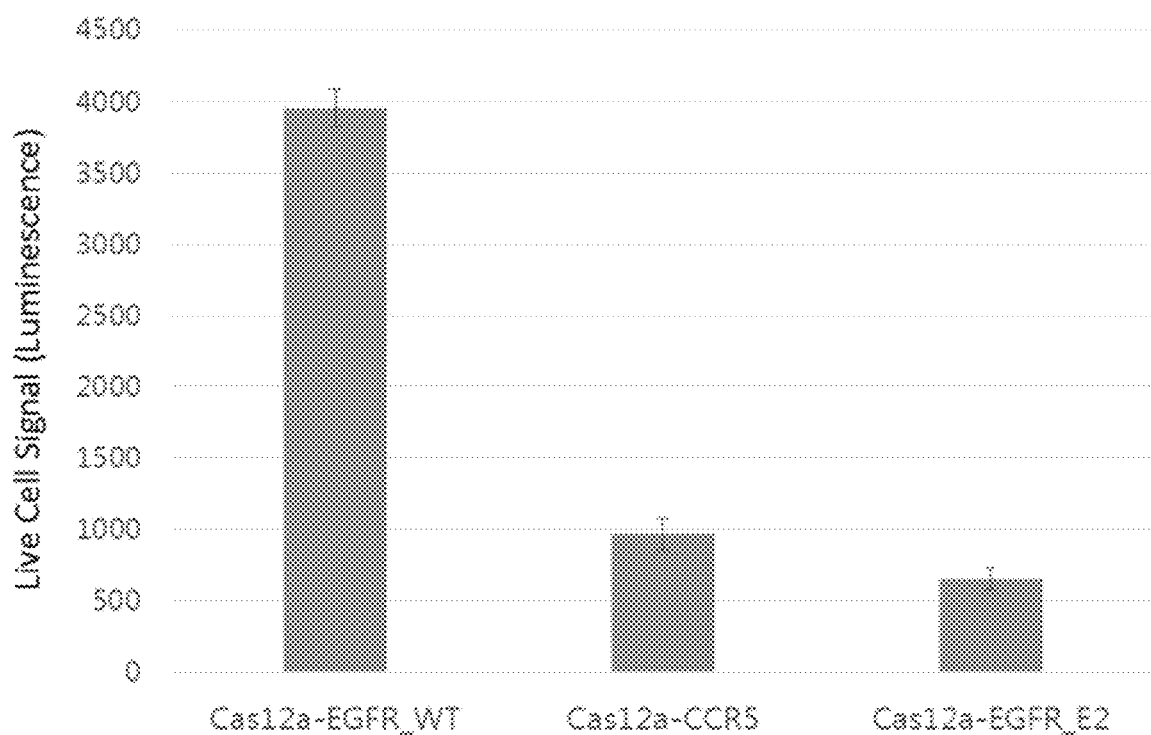
[Fig. 34]
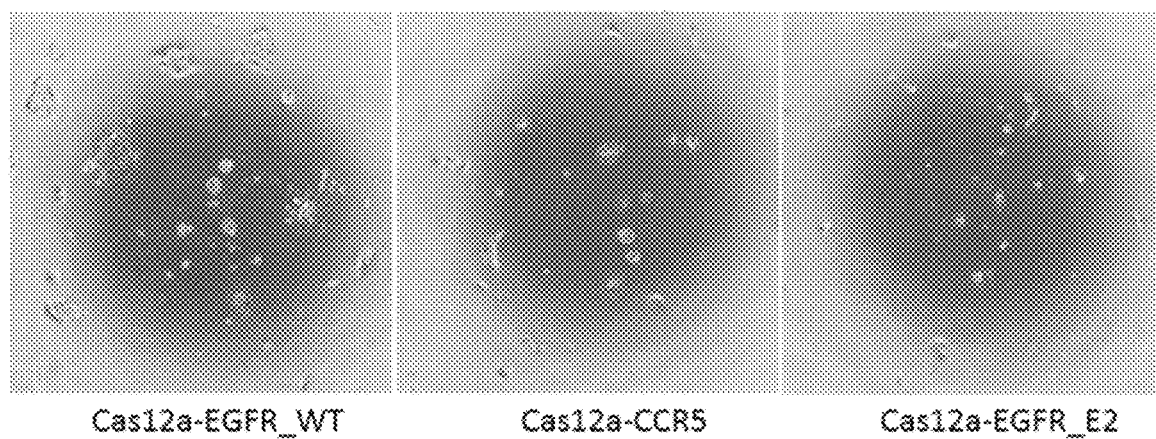

PHARMACEUTICAL COMPOSITION FOR TREATING CANCER, CONTAINING GUIDE RNA AND ENDONUCLEASE AS ACTIVE INGREDIENTS

CROSS REFERENCE TO RELATED APPLICATIONS

This application is a national stage application of PCT/KR2019/003585 filed Mar. 27, 2019, which claims priority from Korean Patent Application No. 10-2018-0035298 filed Mar. 27, 2018.

TECHNICAL FIELD

Embodiments of the present disclosure relate to an anticancer composition comprising a guide RNA and an endonuclease.

BACKGROUND ART

Despite significant breakthroughs in cancer therapy technology, cancer is still the most threatening disease to humans. Cancer can be triggered by a variety of carcinogens and is a disease that can be caused by variations on chromosomal structures or DNA base sequences. One of the most striking features of cancer is constant cell proliferation. Currently, the most widely used anticancer therapy is radiotherapy that efficiently kills cells, or a treatment using a compound or an antibody that targets a specific cancer cell. However, the first-line therapy, including chemotherapy/radiotherapy, may cause serious side effects and pains to the patient by also killing normal proliferating cells in the body, such as hair and immune cells. Therefore, development of an anticancer agent capable of selectively killing only cancer cells in the body is required.

In response to such needs, researches on targeted anticancer agents are actively under way. Targeted anticancer agents are cancer drugs that treat cancer by controlling specific proteins or pathways involved in cancer development. A target specific to cancer cells can be identified by comparing the total protein levels of cancer cells with those of normal cells. In other words, a protein that is specifically present in cancer cells or richer in cancer cells may be a potential target. An example of a target protein is human epidermal growth factor receptor 2 protein (HER-2). In order to treat HER-2 overexpressing breast cancer and stomach cancer, several targeted therapeutic agents have been developed using antibodies against HER-2, including trastuzumab (Herceptin®). Another approach is to target mutant proteins that cause cancer progression. For example, cell proliferation signaling proteins BRCA1 and BRAF exist in modified forms in many breast cancers and melanomas, respectively. Many targeted therapeutic agents have been developed targeting these types of mutations, and the targeted therapeutic agents thus developed have been approved for the treatment of patients with surgically inoperable or metastatic cancers.

Recently developed targeted therapeutic agents and immunotherapeutic agents were based on biomarker proteins specifically expressed in cancer cells. However, the strength of interaction between biomarker proteins specifically present in cancer cells and anticancer agents is not specific and may sometimes lead to adverse side effects. In addition, although targeted therapeutic agents and immunotherapeutic agents are less toxic than the conventional chemotherapeutic agents, many adverse side effects are still reported.

Therefore, in the field of anticancer therapy, the development of an anticancer agent that specifically targets cancer cells in the body is still required. In particular, the development of anticancer agents based on DNA sequence differences, which are the most distinctive features that differentiate cancer cells, is a long-cherished wish of mankind.

DISCLOSURE OF INVENTION

Technical Problem

Structural abnormalities of chromosomes existing in cancer cells or base sequences in cancer cells different from those of normal cells can be important criteria for distinguishing cancer cells from normal cells. Thus, such differences in chromosomes or base sequences may be important targets for cancer treatment. Accordingly, an object of the embodiments is to provide a pharmaceutical composition for treating a cancer, which exhibits an anticancer effect by targeting a sequence specifically present in cancer cells.

Solution to Problem

In order to achieve the above object, an embodiment provides a composition for killing tumor cells comprising a polynucleotide complementarily binding to a nucleic acid specifically present in cancer cells and a nuclease as active ingredients.

Also, an embodiment provides a pharmaceutical composition for the treatment of a cancer comprising the above composition.

In addition, an embodiment provides a composition for killing tumor cells comprising a vector containing a polynucleotide complementarily binding to a nucleic acid specifically present in cancer cells and a polynucleotide encoding an endonuclease and an exonuclease, as an active ingredient.

Further, an embodiment provides a method of the treatment of a cancer comprising administering the composition of the present invention to a subject having the cancer.

Advantageous Effects of Invention

The pharmaceutical composition according to the embodiment is a drug based on high specificity between DNA and RNA which can be customized for each patient and each cancer since it can specifically target and kill cancer cells. In particular, only cancer cells of a patient can be efficiently killed by selectively targeting genes having single nucleotide polymorphisms (SNP) and/or copy number variations (CNV) only existing in cancer cells. In addition, since the target genes do not exist in normal cells, only the cancer cells can be efficiently removed. Therefore, the according to the embodiment is superior to the conventional anticancer agent in terms of safety. Especially, when a fusion protein wherein CRISPR-associated protein is combined with an exonuclease such as RecJ is used, more excellent anticancer agents can be provided.

BRIEF DESCRIPTION OF DRAWINGS

FIG. 1 is a schematic diagram illustrating a process in which the nonspecific exonuclease function of a CRISPR-associated protein is activated by crRNA-guided target site binding to, thereby degrade the target nucleic acid of a cancer cell.

FIG. 2 is a schematic diagram showing that the composition according to an embodiment comprising a crRNA, a CRISPR-associated protein, and/or an exonuclease (hereinafter, referred to as CRISPR PLUS system), is specifically activated in cancer cells and acts as an anticancer agent.

FIG. 3 illustrates that CRISPR/Cas12a protein according to an embodiment has a nonspecific exonuclease activity depending on its sequence-specific endonuclease activity.

FIG. 4 shows the viability of cells measured on 24, 48, and 72 hours after the transfection of human cancer cell lines HEK293 (FIG. 4a) and HeLa (FIG. 4b) with CRISPR/Cas12a (Cpf1) nuclease, a crRNA, or an RNP complex which is a conjugate of the two molecules.

FIG. 5 shows apoptosis induced by a guide RNA specifically binding to an EGFR mutant and Cas9, in pulse only, EGFR_WT, and an experimental group of HCC827 cell line having the EGFR mutant.

FIG. 6 shows a graph comparing the number of live cells in pulse only, EGFR_WT, and the experimental group (EGFR_E2) of HCC827 cell line having the EGFR mutant tested in FIG. 5.

FIG. 7 shows the apoptosis of lung cancer cells induced by guide RNAs complementary to the target genes CCR5, HPRT1, MT2, SMIM11, GNPDA2, SLC15A5, and KCNE2 in lung cancer cell line H1299. In this experiment, lipofection was performed to introduce a nucleic acid encoding a guide RNA and Cas9. NT1 means a guide RNA containing no sequence matching complementary to those in the lung cancer cell and was used as a negative control. In particular, it was confirmed that the guide RNAs complementarily binding to MT2, SMIM11, GNPDA2, SLC15A5, and KCNE2 can efficiently kill the lung cancer cells.

FIG. 8 shows the number of live cells measured to confirm the apoptosis result shown in FIG. 7.

FIG. 9 shows a graph demonstrating that the apoptosis of lung cancer cells is induced by guide RNAs complementary to the target genes CCR5, HPRT1, MT2, GNPDA2, SLC15A5, and KCNE2 in lung cancer cell line H1299. Lipo is a control group was included, wherein only lipofectamine treatment was performed without the introduction of DNA.

FIG. 10 shows the microscopic images of live cells of the NT1 control and the GNPDA2 experimental group obtained using NucBlue Live ReadyProbes Reagent and Propidium Iodide ReadyProbes Reagent. NucBlue Live ReadyProbes Reagent is a blue fluorescent dye that stains both live and dead cells. Propidium Iodide ReadyProbes Reagent is a red fluorescent dye that only stains dead cells.

FIG. 11 shows the number of live cells measured to confirm that the apoptosis of lung cancer cells is induced by guide RNAs complementary to the target genes CCR5, HPRT1, MT2, IRX1, and ADAMTS16 in lung cancer cell line H1563.

FIG. 12 shows the number of live cells over time measured using luminescence to confirm the apoptosis of lung cancer cells induced by guide RNAs complementary to the target genes HPRT1, CCR5, and MT2 in lung cancer cell line A549.

FIG. 13 shows the number of live cells measured to confirm the apoptosis of lung cancer cells induced by guide RNAs complementary to the target genes HPRT1, CCR5, and MT2 in lung cancer cell line A549.

FIG. 14 shows a microscopic observation of the results of FIG. 13.

FIG. 15 shows the number of live cells over time measured using luminescence to confirm the apoptosis of lung cancer cells induced by guide RNAs complementary to the target genes MT2, CD68, DACH2, HERC2P2, and SHBG in lung cancer cell line A549.

FIG. 16 shows the number of live cells over time measured using the luminescence to confirm the apoptosis of breast cancer cells induced by guide RNAs complementary to the target genes MT2, ERBB2, and KRT16 in breast cancer cell line SKBR3.

FIG. 17 shows the number of live cells over time measured to confirm the apoptosis of breast cancer cells induced by guide RNAs complementary to the target genes MT2, ERBB2, and KRT16 in breast cancer cell line SKBR3.

FIG. 18 shows the number of live cells over time measured to confirm the apoptosis of cervical cancer cells induced by guide RNAs complementary to the target genes CCR5, MT2, and PRDM9 in cervical cancer cell line HeLa. CNV of each gene was 2 for CCR5, at least 100 for MT2, and at least 8 for PRDM9.

FIG. 19 shows the number of live cells over time measured to confirm the apoptosis of cervical cancer cells induced by guide RNAs complementary to the target genes CCR5, MT2, PRDM9, and HPV_1 in cervical cancer cell line HeLa. CNV of each gene was 2 for CCR5, at least 100 for MT2, at least 8 for PRDM9, and 30 for HPV_1.

FIG. 20a shows the number of live cells over time measured using luminescence to confirm the apoptosis of cervical cancer cells induced by guide RNAs complementary to the target genes CCR5, MT2, HPV_1, and PRDM9 in cervical cancer cell line HeLa.

FIG. 20b shows the number of live cells measured using luminescence to confirm the apoptosis of cervical cancer cells induced by guide RNAs complementary to the target genes CCR5, MT2, and HPV_1 in cervical cancer cell line HeLa. The NT sequences NT1, NT2, and NT3 targeting the regions not present in the human genome were included as negative control groups.

FIG. 21 shows the number of live cells measured to confirm the apoptosis of colorectal cancer cells induced by guide RNAs complementary to the target genes CCR5, HPRT1, MT2, TRAPPC9, LINC00536, TRPS1, and CDK8 in colorectal cancer cell line HT-29.

FIG. 22 shows the number of live cells measured using luminescence to confirm the apoptosis of colorectal cancer cells induced by guide RNAs complementary to the target genes MT2, CDK8, LINC00536, TRPS1, and TRAPPC9 in colorectal cancer cell line HT-29.

FIG. 23 shows the number of live cells measured to confirm the apoptosis of lung cancer cells induced by guide RNAs complementary to the target genes SMIM11, GNPDA2, SLS15A5, and KCNE2 in colorectal cancer cell line H1563. This experiment was carried out for the purpose of confirming whether the guide RNAs complementary to the target genes effective in the lung cancer cell line H1299 are also effective in other lung cancer cell line H1563.

FIG. 24 provides a microscopic observation of the results of FIG. 23.

FIG. 25 shows a graph demonstrating that the apoptosis of lung cancer cells is induced by guide RNAs complementary to the target genes CCR5, KCNE2, GNPDA2, SMIM11, and SLS15A5. This experiment was carried out in order to confirm the effect of CNV in lung cancer cell line H1299. Since AnnV reagent was added, high luminescence was detected in dead cells.

FIG. 26 shows the cancer cell killing effect of a fusion protein of Cas9, which is a CRISPR-associated protein having endonuclease function, and RecJ, which has exonuclease activity, by employing guide RNAs complementary to the EGFR mutant and CCR5 in the lung cancer cell line HCC827, Cas9, and Cas9-RecJ (SEQ ID NO: 87). As a result, it was confirmed that the ability of killing lung cancer cells was significantly increased in the fusion protein containing the exonuclease.

FIG. 27 displays a microscopic observation of the results of FIG. 26.

FIG. 28 shows the result of an experiment for confirming the effects depending on delivery systems, wherein it was examined whether an RNP (ribonucleoprotein), in which a guide RNA and endonuclease protein Cas9 are combined, have apoptotic effect. Specifically, it was confirmed that the RNP, in which a guide RNA complementarily binding to EGFR mutant in the lung cancer cell line HCC827 are combined with Cas9, efficiently killed the lung cancer cells. On the other hand, the Cas9 protein and the guide RNA used as negative control groups did not kill the cells.

FIG. 29 shows the result of an experiment for confirming the effects depending on delivery systems. In this experiment, it was examined whether an RNP could efficiently induce apoptosis. An sgRNA was used as a control group and an RNP consisting of a guide RNA complementary to MT2 and Cas9 was used as an experimental group. The cell line was H1563, a lung cancer cell line.

FIG. 30 shows the result of an experiment for confirming the effect depending on delivery systems. In this experiment, it was examined whether an RNP could efficiently induce apoptosis. An sgRNA and Cas9 protein were used as control groups and RNPs each consisting of Cas9 and a guide RNA complementary to any one of CCR5, GNPDA2, and SMIM11 were used as experimental groups. The cell line was H1299, a lung cancer cell line.

FIG. 31 shows the result of an experiment for confirming the effects depending on the delivery systems. In this experiment, it was examined whether an RNP could efficiently induce apoptosis. An sgRNA and Cas9 protein were used as control groups and RNPs each consisting of Cas9 and a guide RNA complementary to CCR5 or MT2, were used as experimental groups. The cell line was H1299, a lung cancer cell line.

FIG. 32 provides a microscopic observation of the results of FIG. 30.

FIG. 33 demonstrates the induction of apoptosis using guide RNAs complementary to the target genes CCR5 and EGFR_E2, and Cas12a. The cell line was HCC827, a lung cancer cell line.

FIG. 34 displays a microscopic observation of the results of FIG. 33.

BEST MODE FOR CARRYING OUT THE INVENTION

An embodiment of the present disclosure provides a composition for killing tumor cells comprising a polynucleotide complementarily binding to a nucleic acid specifically present in cancer cells and a nuclease as active ingredients.

The polynucleotide according to an embodiment may be a crRNA or a gRNA. The crRNA refers to a CRISPR RNA. Also, the gRNA refers to a guide RNA. The crRNA and the gRNA may be single strand RNAs. In addition, the crRNA can bind to a tracrRNA to activate a CRISPR-associated protein, and the crRNA may be used in combination with the tracrRNA. The crRNA may have a sequence complementary to a gene sequence that is specifically present in a target cancer cell. In addition, the gRNA may bind to a gene sequence that is specifically present in a target cancer cell, thereby causing the CRISPR-associated protein to exhibit activity. The crRNA or gRNA may be an RNA composed of 15 to 40 nucleotides. The polynucleotide may be composed of 18 to 30 or 20 to 25 nucleotides. For example, the crRNA or gRNA may be composed of 20 nucleotides. In addition, the crRNA or gRNA may contain additional sequences at the 3' end to make a CRISPR-associated protein, such as Cas9, active. In one embodiment, the gRNA may be an RNA which is produced by the DNA represented by any one of SEQ ID NOs: 87 to 129.

The term "nuclease" as used herein, may mean an endonuclease. The nuclease may be a CRISPR-associated protein. The term "CRISPR-associated protein" as used herein means an enzyme capable of recognizing and cleaving a double-stranded or single-stranded nucleic acid such as DNA and RNA (dsDNA/RNA and ssDNA/RNA). Specifically, they can recognize and cleave a double-stranded or single-stranded nucleic acid bound to a crRNA or a guide RNA.

In an embodiment of the present disclosure, the nuclease of the present invention may be an endonuclease whose function is activated by recognizing the binding of the crRNA to the target site. In addition, as the endonuclease function is activated, it may have an exonuclease activity capable of nonspecifically cleaving double-stranded and/or single-stranded DNA and/or RNA. Also, a CRISPR-associated protein such as Cas12a, once activated, may exhibit nonspecific exonuclease activity. It can nonspecifically cleave DNA and RNA.

Accordingly, an exemplary composition of the present disclosure can specifically kill cancer cells by a nonspecific nuclease that is activated by the binding of crRNA or gRNA to a specific target site present in the cancer cells. As described above, the composition according to an embodiment is capable of specifically killing only cancer cells and thus may be used as an anticancer agent.

For example, the CRISPR-associated protein may be any one nuclease selected from the group consisting of Cas1, Cas1B, Cas2, Cas3, Cas4, Cas5, Cas6, Cas7, Cas8, Cas9, Cas10, Cas12a, Cas12b, Cas12c, Cas12d, Cas12e, Cas12g, Cas12h, Cas12i, Cas13a, Cas13b, Cas13c, Cas13d, Cas14, Csy1, Csy2, Csy3, Cse1, Cse2, Csc1, Csc2, Csa5, Csn2, CsMT2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. Preferably the CRISPR-associated protein may be a nuclease of Cas9, Cas12a (Cpf1), or Cas13a (C2c2).

As an example of the CRISPR-associated protein, the Cas9 protein may have the amino acid sequence of SEQ ID NO: 20. The Cas9 protein may be encoded by a nucleic acid having the sequence of SEQ ID NO: 19. In addition, the Cpf1 protein may have the amino acid sequence of SEQ ID NO: 22. The Cpf1 protein may be encoded by a nucleic acid having the sequence of SEQ ID NO: 21. In addition, the C2c2 protein may have the amino acid sequence of SEQ ID NO: 24. The C2c2 protein may be encoded by a nucleic acid having the sequence of SEQ ID NO: 23.

As used herein, the term "a nucleic acid specifically present in cancer cells" refers to a nucleic acid that exists only in cancer cells, which differentiates cancer cells from normal cells. That is, it may mean a sequence different from that in a normal cell, and the sequence may be different in terms of at least one nucleic acid. Further, a part of a gene may be substituted or deleted. Also, it may have a sequence wherein a particular sequence is repeated. In this case, the repeated sequence may be a sequence existing in the cell, or may be an externally inserted sequence.

For example, the nucleic acid that is specifically present in cancer cells may be characterized by single nucleotide polymorphism (SNP), copy number variation (CNV), structural variation (SV), gene insertion, or gene deletion.

Specifically, the sequence specifically present in cancer cells may be an SNP present in cancer cells. A target DNA having the above sequence present in cancer cells and a crRNA or a guide RNA having a sequence complementary to the target DNA can specifically bind to each other. Thus, the nucleic acid specifically present in cancer cells can give specificity to the composition for killing tumor cells. In particular, as a nucleic acid specifically present in cancer cells, specific SNPs existing only in cancer cells may be identified by the genome sequence analysis of various cancer tissues, and crRNA or gRNA may be prepared using the specific SNPs. Therefore, since this exhibits cancer cell-specific toxicity, it may make it possible to develop a patient-customized anti-cancer therapeutic agent.

In addition, the sequence specifically present in cancer cells may contain a copy number variation (CNV) present in cancer cells. CNV means a variation in which sections of the genome are repeated. The number of repetitive genes may vary according to cancer types or individuals. Conventionally, CNV refers to a nucleic acid fragment showing differences in the number of repeated sequences by deletion, amplification, or the like as compared to the human reference genome, unlike usual genes existing in a copy number of 2. For example, a gene having CNV of 2 in normal cells, but having CNV of 4 or more in cancer cells may give specificity to a composition for killing tumor cells. CNV may be at least 4, 8, 10, 12, 14, 16, 18, 20, 24, 30, 40, 50, 60, 70, 80, 90 or 100. Specifically, when the copy number is 7 or more, it may be determined as CNV. Specific examples of the copy numbers of the genes for each cancer cell line are shown in Table 1 below.

TABLE 1

| Type | Cell line | Gene name | gRNA | Copy number |
| --- | --- | --- | --- | --- |
| Lung | HCC827 | EGFR | SEQ ID NO: 88 | >16 |
| | | VSTMT2A | SEQ ID NO: 89 | >13 |
| | | KIF5A | SEQ ID NO: 90 | >14 |
| | H1563 | IRX1 | SEQ ID NO: 91 | >8 |
| | | ADAMTS16 | SEQ ID NO: 92 | >7 |
| | H1299 | GNPDA2 | SEQ ID NO: 93 | >12 |
| | | KCNE2 | SEQ ID NO: 94 | >40 |
| | | SLC15A5 | SEQ ID NO: 95 | >12 |
| | | SMIM11 | SEQ ID NO: 96 | >40 |
| | A549 | DACH2 | SEQ ID NO: 97 | >18 |
| | | HERC2P2 | SEQ ID NO: 98 | >8 |
| | | CD68 | SEQ ID NO: 99 | >10 |
| | | SHBG | SEQ ID NO: 100 | >9 |
| Breast | SKBR3 | ERBB2 | SEQ ID NO: 101-108 | >33 |
| | | KRT16 | SEQ ID NO: 109, 110 | >8 |
| Colon | HT-29 | LINC00536 | SEQ ID NO: 111 | >9 |
| | | TRPS1 | SEQ ID NO: 112 | >8 |
| | | CDK8 | SEQ ID NO: 113 | >18 |
| | | TRAPPC9 | SEQ ID NO: 114 | >13 |
| | | HERC2P2 | SEQ ID NO: 98 | >8 |
| Pancreas | Capan2 | SIRPB1 | SEQ ID NO: 115 | >24 |
| | | MRC1 | SEQ ID NO: 116 | >18 |
| | | ATP11A | SEQ ID NO: 117 | >8 |
| | | POTEB | SEQ ID NO: 118 | >7 |
| | | HERC2P2 | SEQ ID NO: 98 | >7 |
| Cervix | HeLa | PRDM9 | SEQ ID NO: 119 | >8 |
| | | CDKN2B | SEQ ID NO: 120 | >10 |
| | | HPV | SEQ ID NO: 121-124 | 30 |

TABLE 1-continued

| Type | Cell line | Gene name | gRNA | Copy number |
| --- | --- | --- | --- | --- |
| ETC | | LINE2(mt2) | SEQ ID NO: 125 | >100 |
| | | CCR5 | SEQ ID NO: 126 | 2 |
| | | HPRT1 | SEQ ID NO: 127 | 2 |
| | | NT | SEQ ID NO: 128-130 | 0 |

The CNV is one of the most important variant types associated with human diseases such as cancer, intellectual disability, epilepsy, schizophrenia, childhood obesity, and the like. Most cancer cell lines have CNV, and a target sequence present in the CNV and a guide RNA having a sequence complementary thereto bind specifically to each other. Thus, the CNV specifically present in cancer cells can give specificity to the anticancer agent of the present disclosure. In particular, the higher the number of CNV, the greater the number of genes cleaved by a CRISPR-associated protein, resulting in a significant damage to the cancer cell nucleus.

In particular, the data of CNV specifically present in cancer cells may be easily obtained by techniques such as microarray and fluorescence in situ hybridization (FISH), and may be used to produce crRNA or gRNA. When cancer cells are treated with crRNA or gRNA targeting a specific sequence in the CNV of the cancer cells and a CRISPR-associated protein, cancer-cell specific apoptosis may be induced. Therefore, since this exhibits cancer cell-specific toxicity, it may make it possible to develop a patient-customized anti-cancer therapeutic agent.

In one embodiment of the present disclosure, the expected copy number (N) of CNV may be calculated from the copy number value (V) using the following equation: $N=2\times 2^V$.

In one embodiment of the present disclosure, it was confirmed that only cancer cells could be effectively killed when a polynucleotide complementarily binding to a gene having a specifically high CNV in cancer cells was used together with a CRISPR-associated protein or a CRISPR PLUS protein wherein a CRISPR-associated protein is fused with an exonuclease protein. In addition, it was confirmed that cancer cells can be killed more effectively upon using a gene having a high CNV selected among gene mutations specifically present in cancer cells.

In addition, sequences specifically present in cancer cells may be structural variations (SVs) present in cancer cells, and the SVs may be inversion, translocation, short nucleotide repeat expansion, and the like.

The inversion is a mutation in which a part of the gene is inverted and is one of the mutation types associated with diseases such as hemophilia and lung cancer. The translocation is a mutation in which a part of the chromosome falls off and binds to another chromosome. The short nucleotide repeat expansion is a mutation in which the same sequence is continuously repeated and over-amplified.

Most cancer cell lines have SVs such as gene inversion, translocation, and short nucleotide repeat expansion, and the junction sequence between the terminal of the sequence with SV and the terminal of the normal cell line sequence exists only in the corresponding cancer cell line. The SV junction sequence present in the cancer cell and a guide RNA having a sequence complementary thereto bind specifically to each other. Thus, the SV junction sequence specifically present in cancer cells can give specificity to the anticancer agent of the present invention.

In particular, unlike CNV, the SV junction sequence is not present in normal cells and, accordingly, it is specific to cancer cells. Therefore, when cancer cells are treated with a polynucleotide complementarily binding to an SV junction sequence existing in cancer cells and a CRISPR-associated protein, cancer cell-specific apoptosis may be induced. Therefore, since this exhibits specific toxicity only to particular cancer cells, it may make it possible to develop a patient-customized anti-cancer therapeutic agent.

In addition, sequences that are specifically present in cancer cells may be generated by the insertion or deletion of a gene. A guide RNA having a sequence complementary to the sequence mutated by insertion or deletion can effectively kill cancer cells. Therefore, the insertion or deletion of a gene specifically present in cancer cells can give specificity to the anticancer agent of present invention.

In particular, the insertion and deletion mutant sequences are specific to cancer cells as they are not present in normal cells like the SV junction sequence, and when the insertion or deletion mutant sequence present in cancer cells is treated with a CRISPR-associated protein, apoptosis may be induced specifically. However, when the insertion and deletion mutant sequences are targeted, a PAM (protospacer adjacent motif) sequence which can be recognized by a gene near the Indel (insertion and deletion) may be required.

In addition, the inserted gene may be a nucleic acid sequence existing in the cell, but may be an externally introduced gene sequence. In particular, in the case of cancer cells caused by viral infection or the like, viral genes can be inserted into the cells. In an embodiment of the present disclosure, the viral nucleic acid sequence can be used as a nucleic acid specifically present in cancer cells. In particular, the cancer having such insertion mutation is not common, but the inserted viral sequence is specific to cancer cells because it is not present in normal cells. In addition, when the viral sequence is integrated in multiple copies, CNV is high, which can certainly induce the apoptosis of cancer cells. An example of such cancers may be cervical cancer caused by papillomavirus. An example of such gRNA targeting externally introduced gene may be a gRNA produced by the DNA of any one of SEQ ID NOs: 121 to 124.

In addition, 5'-NGG-3' sequence, which is a PAM (protospacer associated motif) sequence, may be considered together to select a gene specific to cancer cells and a polynucleotide sequence complementary to the gene. For example, when the 5'-NGG-3' sequence is present near the cancer cell-specific sequence, 20 nucleotides in the 3' direction may be designated as a target. In selecting the target gene, a gene having a clear sequence information such as insertion of a gene, deletion of a gene, and a junction region, and a gene having a high copy number of CNV may be preferentially selected. In order to select the target sequence, it may be confirmed whether or not G or C exists at the 5' and 3' ends of the sequence, whether or not the GC content (%) of the entire sequence is within 40 to 60%, and whether the third-the fourth base portion in the 3' direction of PAM, which is the sequence for cleavage of an endonuclease, CRISPR-associated protein, is A or T. The binding affinity of sgRNA may be increased when G or C is present at the 5'- and 3'-ends of the sequence and when the GC content (%) of the entire sequence is within 40 to 60%. In particular, when the third-the fourth base portion in the 3' direction of PAM, which is the site where *Streptococcus pyogenes* Cas9 (Sp-Cas9) cleaves the sequence, is A or T, the cleavage efficiency of SpCas9 may be enhanced.

Examples of the above cancer may be any one selected from the group consisting of bladder cancer, bone cancer, blood cancer, breast cancer, melanoma, thyroid cancer, parathyroid cancer, bone marrow cancer, rectal cancer, throat cancer, larynx cancer, lung cancer, esophageal cancer, pancreatic cancer, gastric cancer, tongue cancer, skin cancer, brain tumor, uterine cancer, head or neck cancer, gallbladder cancer, oral cancer, colon cancer, perianal cancer, central nervous system tumor, liver cancer, and colorectal cancer. In particular, it may be gastric cancer, colorectal cancer, liver cancer, lung cancer, or breast cancer, which are known as the five major cancers in Korea.

The nucleic acid specifically present in the above cancers may be a mutant of any one gene selected from the group consisting of p53, PTEN, APC, MSH2, HBV, HCV, and EGFR, but is not limited thereto. Specifically, for gastric cancer, it may be a mutant of p53 or PTEN, known as tumor suppressor genes. In the case of colorectal cancer, it may be a mutant of APC or MSH2 gene. In addition, liver cancer is mainly caused by the infection of HBV and HCV viruses, so nucleic acids of HBV or HCV can be targeted. In addition, in lung cancer, mutation of the EGFR gene may be targeted and, in the case of breast cancer, the mutation of the BRCA1/2 gene may be a main target.

As described above, mutant genes and viral genes closely related to the development of cancers may be selected as nucleic acid sequences specifically existing in cancer cells and may be used for the production of a crRNA or a gRNA. At this time, any SNP of DNA that is specifically present in cancer cells may be used. Examples of the nucleic acid sequences that are specifically present in cancer cells may be the sequences described in Table 2 below, but are not limited thereto.

TABLE 2

| Gene | Kind of Cancer | Normal cell | Cancer cell | Protein Modification |
|---|---|---|---|---|
| BRCA1 Exon 7 | Ovarian cancer/ breast | 608: CAAAGTATGGGCTACA GAAACCGTGCCAAAAG (SEQ ID NO: 26) | 608: CAAAGTATGGGCTTCAG AAACCGTGCCAAAAG (SEQ ID NO: 27) | p.Tyr130 → Phe |
| BRCA1 Exon 10 | cancer | 1615: TGGGAAAACCTATCGG AAGAAGGCAAGCCTCC (SEQ ID NO: 28) | 1615: TGGGAAAACCTATCGG TAGAAGGCAAGCCTCC (SEQ ID NO: 29) | p.Lys467 → non-sense |
| BRCA1 Exon 11 | | 3845: GGGGCCAAGAAA- TTAGAGTCCTCAGAAGAG (SEQ ID NO: 30) | 3845: GGGGCCAAGAAAATTA GAGTCCTCAGAAGAG (SEQ ID NO: 31) | p.Leu1209 → Ile |
| BRCA1 Exon 11 | | 4260: ATGATGAAGAAAGAG GAACGGGCTTGGAAGA (SEQ ID NO: 32) | 4260: ATGATGAAGAAAG- GAACGGGCTTGGAAGA (SEQ ID NO: 33) | p.Gly1348 → Asn |
| BRCA1 Exon 11 | | 3657: CATCTCAGGTTTGTTC TGAGACACCTGATGACC (SEQ ID NO: 34) | 3657: CATCTCAGGTTTGTTC T-AGACACCTGATGACC (SEQ ID NO: 35) | p.Glu1148 → Arg |

TABLE 2-continued

| Gene | Kind of Cancer | Normal cell | Cancer cell | Protein Modification |
|---|---|---|---|---|
| BRCA1 Exon 15 | | 7466: ATATACAGGATATGCG AATTAAGAAGAAACAAA (SEQ ID NO: 36) | 7466: ATATACAGGATATGTG AATTAAGAAGAAACAAA (SEQ ID NO: 37) | p.Arg2494 → Thr |
| TP53 | Gastric cancer | 125: TAGGAGGCCGAGCTCT GTTGCTTCGAACTCCA (SEQ ID NO: 38) | 125: TAGGAGGCCGAGCTCT- TTGCTTCGAACTCCA (SEQ ID NO: 39) | p.Leu20 → Cys |
| MSH2 | Colorectal cancer | 126: TGAGGAGGTTTCGACAT GGCGGTGCAGCCGA (SEQ ID NO: 40) | 126: TGAGGAGGTTTCGACCT GGCGGTGCAGCCGA (SEQ ID NO: 41) | p.Met1 → Leu |
| EGFR | Lung cancer | 2137: AAAAAGATCAAAGTG CTGGGCTCCGGTGCGTT (SEQ ID NO: 42) | 2137: AAAAAGATCAAAGTGC TGAGCTCCGGTGCGTT (SEQ ID NO: 43) | p.Gly719 → Ser |
| FGFR3 | Liver cancer | 1771: ATCCTCTCTCTGAAAT CACTGAGCAGGAGAAAG (SEQ ID NO: 44) | 1771: ATCCTCTCTCTGAAATC ACTGCGCAGGAGAAAG (SEQ ID NO: 45) | p.Glu545 → Ala |

At this time, a CRISPR RNA targeting the nucleic acid sequence specifically present in cancer cells may contain one or more crRNA or gRNA sequences. For example, a crRNA or gRNA that can simultaneously target exon 10 or 11 of BRCA1 present in ovarian cancer or breast cancer may be used. In addition, two or more crRNAs or gRNAs targeting BRCA1 exon 11 may be used. Thus, the combination of crRNA or gRNA may be suitably selected depending on the purpose of cancer treatment and the kind of cancer. That is, different gRNAs may be selected and used.

The tumor-killing composition of the present disclosure may further comprise an exonuclease.

As used herein, the term "exonuclease" is an enzyme that cleaves nucleotides from either the 5' or 3' end of a nucleic acid molecule. Thus, the exonuclease may be a 5'→3' nuclease that degrades the nucleic acid in the 5' to 3' direction. In addition, the exonuclease may be a 3'→5' nuclease which degrades the nucleic acid in the 3' to 5' direction.

Specifically, an example of the 5'→3' nuclease may be RecE or RecJ derived from *E. coli*. It may also be T5 derived from bacteriophage T5. In addition, an example of the 3'→5' nuclease may be Exo I derived from eukaryotic cells or prokaryotic cells. It may also be Exo III derived from *E. coli*. It may also be human-derived Trex1 or Trex2. In addition, the nuclease having 5'→3' and 3'→5' bi-directional cleavage activity may be ExoVII or RecBCD derived from *E. coli*. Further, as an example, it may be 5'→3' lambda exonuclease from *E. coli*. It may also be Mungbean derived from *Vigna radiata* that can cut single-stranded DNA.

An exemplary exonuclease may be any one selected from the group consisting of Exoribonuclease T, TREX2, TREX1, RecBCD, Exodeoxyribonuclease I, Exodeoxyribonuclease III, Mungbean exonuclease, RecE, RecJ, T5, Lambda exonuclease, Exonuclease VII small unit, Exonuclease VII large unit, Exo I, Exo III, Exo VII, and Lexo.

Specifically, the exonuclease may be any one selected from the group consisting of Exoribonuclease T (SEQ ID NO: 4), TREX2 (SEQ ID NO: 5), TREX1 (SEQ ID NO: 6), RecBCD_RecB (SEQ ID NO: 7), RecBCD_RecC (SEQ ID NO: 8), RecBCD_RecD (SEQ ID NO: 9), Exodeoxyribonuclease I (SEQ ID NO: 10), Exodeoxyribonuclease III (SEQ ID NO: 11), Mungbean exonuclease (SEQ ID NO: 12), RecJ (SEQ ID NO: 13), RecE (SEQ ID NO: 14), T5 (SEQ ID NO: 15), Lambda exonuclease (SEQ ID NO: 16), Exonuclease VII small unit (SEQ ID NO: 17), and Exonuclease VII large unit (SEQ ID NO: 18).

Another embodiment provides a composition for killing tumor cells, comprising a polynucleotide complementarily binding to a nucleic acid specifically present in cancer cells and a fusion protein consisting of an endonuclease and an exonuclease, as active ingredients.

The terms "a nucleic acid specifically present in cancer cells," "a polynucleotide complementarily binding to a nucleic acid specifically present in cancer cells," "endonuclease," and "exonuclease" are as described above.

For example, a CRISPR/Cas system capable of effectively killing cells with the desired nucleic acid sequence, prepared by combining the exonuclease with the crRNA and the CRISPR-associated protein, was named CRISPR PLUS.

An example of the fusion protein consisting of the endonuclease and the exonuclease may be Cas9-Exoribonuclease T, Cas9-REX2, Cas9-TREX1, Cas9-RecBCD_RecB, Cas9-RecBCD_RecC, Cas9-RecBCD_RecD, Cas9-Exodeoxyribonuclease I, Cas9-Exodeoxyribonuclease III, Cas9-Mungbean, Cas9-RecJ, Cas9-RecE, Cas9-T5, Cas9-Lambda, Cas9-Exonuclease VII small unit, Cas9-Exonuclease VII large unit, Cpf1-Exoribonuclease T, Cpf1-REX2, Cpf1-TREX1, Cpf1-RecBCD_RecB, Cpf1-RecBCD_RecC, Cpf1-RecBCD_RecD, Cpf1-Exodeoxyribonuclease I, Cpf1-Exodeoxyribonuclease III, Cpf1-Mungbean, Cpf1-RecJ, Cpf1-RecE, Cpf1-T5, Cpf1-Lambda, Cpf1-Exonuclease VII small unit, or Cpf1-Exonuclease VII large unit, preferably Cas9-RecJ or Cpf1-RecJ, but is not limited thereto.

In one embodiment of the present disclosure, the use of the CRISPR PLUS protein comprising a fusion protein of an endonuclease and an exonuclease resulted in an increased rate of apoptosis in a small number of CNV, such as CCR5 gene with CNV 2, and a better apoptotic effect was observed than when the endonuclease alone was used.

In an aspect, the endonuclease and the exonuclease may be joined through a linker. The linker may be an albumin linker or a peptide linker. The linker may comprise 1 to 50 amino acids, 3 to 40 amino acids, or 10 to 30 amino acids. In addition, the peptide linker may be a peptide consisting of Gly and Ser residues. Further, the peptide linker may be a peptide consisting of 1 to 10 amino acids selected from the group consisting of leucine (Leu, L), isoleucine (Ile, I), alanine (Ala, A), valine (Val, V), proline (Pro, P), lysine (Lys, K), arginine (Arg, R), asparagine (Asn, N), serine (Ser, S), and glutamine (Gln, Q). In addition, the linker may be a polypeptide consisting of 3 to 15 amino acids composed of glycine (Gly, G) and serine (Ser, S) residues, and may be composed of 6 to 11 amino acids.

In another aspect, there is provided a pharmaceutical composition for treating a cancer comprising the composition for killing a tumor cell described above.

The tumor or cancer is any one selected from the group consisting of bladder cancer, bone cancer, blood cancer, breast cancer, melanoma, thyroid cancer, parathyroid cancer, bone marrow cancer, rectal cancer, throat cancer, larynx cancer, lung cancer, esophageal cancer, pancreatic cancer, gastric cancer, tongue cancer, skin cancer, brain tumor, uterine cancer, head or neck cancer, gallbladder cancer, oral cancer, colon cancer, perianal cancer, central nervous system tumor, liver cancer, and colorectal cancer.

Formulations of the pharmaceutical compositions of the present disclosure may be parenteral. When formulated, a diluent or excipient such as a filler, an extender, a binder, a wetting agent, a disintegrant, or a surfactant is usually used. Particularly, preparations for parenteral administration include sterilized aqueous solutions, non-aqueous solutions, suspensions, emulsions, freeze-dried preparations, and suppositories. As solvents for non-aqueous solutions and suspensions, propylene glycol, polyethylene glycol, vegetable oils such as olive oil, injectable esters such as ethyl oleate, and the like may be used.

The pharmaceutical composition of the present disclosure may be administered parenterally, and may be administered via any one route selected from the group consisting of intratumoral, intravenous, intramuscular, intradermal, subcutaneous, intraperitoneal, intra-arteriolar, intraventricular, intralesional, intrathecal, topical, and a combination thereof.

The dosage of the pharmaceutical composition of the present disclosure varies depending on the body weight, age, sex, health condition, diet, administration time, administration method, excretion rate, and severity of disease of the patient and may be appropriately selected by those skilled in the art. For a desired effect, the pharmaceutical composition of the present invention may be administered at a dose of 0.01 μg/kg to 100 mg/kg, more specifically, 1 μg/kg to 1 mg/kg, per day. The administration may be carried out once a day or divided into several doses. Thus, the dosages are not intended to limit the scope of the invention in any manner.

In another aspect, the present disclosure also provides a composition for killing tumor cells comprising a vector containing a polynucleotide complementarily binding to a nucleic acid specifically present in cancer cells and a polynucleotide encoding an endonuclease, as an active ingredient.

The terms "a nucleic acid specifically present in cancer cells," "endonuclease," and "exonuclease" are as described above. In addition, "a polynucleotide complementarily binding to a nucleic acid specifically present in cancer cells" is DNA. The DNA nucleic acid may produce a crRNA or a gRNA capable of complementarily binding to a nucleic acid sequence that is specifically present in a cancer cell. Here, "crRNA" and "gRNA" are as described above.

In the above composition, i) the polynucleotide complementarily binding to a nucleic acid specifically present in cancer cells, and ii) the polynucleotide encoding an endonuclease may be loaded into a single vector. If necessary, i) the polynucleotide complementarily binding to a nucleic acid specifically present in cancer cells and ii) the polynucleotide encoding an endonuclease may be loaded in separate vectors.

In addition, the composition may additionally comprise a polynucleotide encoding an exonuclease in the vector. Also, i) the polynucleotide complementarily binding to a nucleic acid specifically present in cancer cells, ii) the polynucleotide encoding an endonuclease, and iii) the polynucleotide encoding an exonuclease may be loaded in separate vectors, as necessary.

In an embodiment, the composition may be a composition for killing tumor cells which comprises as an active ingredient a vector containing a polynucleotide complementarily binding to a nucleic acid sequence specifically present in cancer cells and a polynucleotide encoding a fusion protein of a CRISPR-associated protein and an exonuclease. In one embodiment of the present disclosure, a polynucleotide encoding Cas9-RecJ fusion protein, wherein a CRISPR-associated protein (endonuclease), Cas9, is fused with an exonuclease, RecJ, was used as loaded in a vector.

The vector may be a viral vector or a plasmid vector, but is not limited thereto. A vector containing the polynucleotide complementarily binding to a nucleic acid specifically present in cancer cells, the polynucleotide encoding a CRISPR-associated protein, and/or the polynucleotide encoding an exonuclease may be prepared by a cloning method known in the art, and the method is not particularly limited.

In addition, an embodiment provides a method of treating a cancer comprising administering the above-described composition for killing tumor cells to a subject.

At this time, the polynucleotide complementarily binding to a nucleic acid specifically present in cancer cells and the nuclease protein may be combined into the form of RNP and administered to a subject having a cancer. In addition, an exonuclease may be added to the RNP and administered to the subject having a cancer The pharmaceutical composition of the present disclosure may be administered to mammals such as livestock, human, and the like in various routes. All modes of administration may be expected and, for example, the administration is via any one route selected from the group consisting of intratumoral, intravenous, intramuscular, intradermal, subcutaneous, intraperitoneal, intra-arteriolar, intraventricular, intralesional, intrathecal, topical, and a combination thereof.

MODE FOR THE INVENTION

Hereinafter, the present invention will be described in detail by referring to Examples. However, the following examples are intended to illustrate the present invention, and the scope of the invention is not limited thereto only.

Preparation Example 1: Preparation of crRNA for Cas9

The exact nucleotide sequence of a target gene was obtained through gene sequencing. After identifying the protospacer adjacent motif (PAM, 5'-NGG-3') in the exon of the target gene, its upstream 20-mer sequence was determined as the protospacer sequence. At least three kinds of protospacers were designed because the editing efficiency in cells differs depending on the position of the target sequence.

Oligonucleotides (oligomers) were synthesized by binding 5'-TAGG-3' to the 5' portion of the 20-mer sequence and binding 5'-AAAC-3' to the 3' portion of a complementary sequence. The two synthesized oligomers were adjusted to 100 μM and each 2 μl was taken and diluted in 46 μl of purified water.

Annealing was carried out using a thermocycler, and the reaction mixture was treated at 95° C. for 5 minutes, cooled to 55° C. at a rate of 4° C./sec and then treated for 10 minutes. About 5 to 10 μg of pUC19 vector containing T7 promoter (SEQ ID NO: 1: TAATACGACTCACTATAGG) for in vitro transcription and crRNA scaffold sequence (SEQ ID NO: 2: GTTTTAGAGCTAGAAATAGCAAGT-TAAAATAAGGCTAGTCCGTTATCAACTT GAAAAAGTGGCACCGAGTCGGTGC) was digested with BsaI restriction enzyme overnight and then purified. Its sequence was represented by (SEQ ID NO: 3)
5'-TAATACGACTCACTATAGGTGAGACCGcAGGTCTCGGT

TTTAGAGCTAGAAATAGCAAGTTAAAATAAGGCTAGTCCGT

TATCAACTTGAAAAAGTGGCACCGAGTCGGTGC-3'

Thereafter, ligation was performed on the vector treated with the restriction enzyme (100 to 200 ng/μl). 6 μl of 5 annealing mixture, 2 μl of the vector, 1 μl of T4 DNA ligase 10× buffer (Promega C126B), and 1 μl of T4 DNA ligase (Promega M180A) were placed in an 1.5 ml Eppendorf tube, mixed by tapping, and incubated overnight at 4° C. E. coli DH5α was transformed with the ligation mixture. Cloning was confirmed by the following sequence through Sanger sequencing using the M13 primer:

(SEQ ID NO: 1)
5'-TAATACGACTCACTATAGG-20 mer protospacer sequence-
(SEQ ID NO: 2)
GTTTTAGAGCTAGAAATAGCAAGTTAAAATAAGGCTAGTC

CGTTATCAACTTGAAAAAGTGGCACCGAGTCGGTGC-3'.

Using the thus prepared DNA sequence, the region including T7 promoter, protospacer, and crRNA scaffold was amplified by polymerase chain reaction (PCR), confirmed by agarose gel electrophoresis, and then purified. About 800 ng of the 10 outcomes were reacted in 50 μl reaction volume for about 4 to 8 hours using MEGAshortscript™ T7 Kit (Invitrogen, AM1354) to transcribe the crRNA in vitro.

The transcription product was purified using MEGAclear™ Kit (Invitrogen, AM1908) and the concentration of the purified crRNA was measured with a spectrophotometer. Generally, about 1 to 2 μg/μl or more of crRNA was obtained. At this time, attention was paid to prevent RNase contamination. The purified crRNA was diluted and dispensed at the required concentration and volume, and then stored at −80° C., while care was taken to avoid temperature changes and shocks.

Preparation Example 2: Preparation of crRNA for Cpf1 (Cas12a)

The exact nucleotide sequence of a target gene was obtained through gene sequencing. After determining the target site, a protospacer adjacent motif (PAM, 5'-TTTN-3') sequence was found in the exon portion and downstream 24-mer sequence thereof was determined as a protospacer sequence. At this time, the site where the protospacer sequence had about 50% of guanine-cytosine content was determined as a target. At least three kinds of protospacers were designed because the editing efficiency in cells differs depending on the position of the target sequence.

Oligomers were synthesized for the sequence containing T7 promoter for in vitro transcription and crRNA, and its complementary sequence, respectively:

(SEQ ID NO: 25)
5'-AATTCTAATACGACTCACTATAGGAATTTCTACTGTTG

TAGAT-24 mer protospacer sequence-3'.

A mixture of final volume of 20 μl containing 2 μg each of the synthesized oligomers was prepared. At this time, purified water without nuclease was used.

Annealing was carried out using a thermocycler, and the reaction mixture was treated at 95° C. for 5 minutes, cooled to 55° C. at a rate of 4° C./sec and then treated for 10 minutes. 4 μl (800 ng) of the 5 outcomes were reacted in 50 μl reaction volume for about 4 to 8 hours using MEGAshortscript™ T7 Kit (Invitrogen, AM1354) to transcribe the crRNA in vitro. The resulting crRNA was purified by ethanol precipitation, and its concentration was determined with a spectrophotometer. Generally, about 1 to 2 μg/μl or more of crRNA was obtained, and attention was paid to prevent RNase contamination. The purified crRNA was diluted and dispensed at the required concentration and volume, and then stored at −80° C., while care was taken to avoid temperature changes and shocks.

Preparation Example 3: Preparation of Substrate DNA

A dsDNA of about 1 to 1.5 kbp was amplified from a template containing the target gene using a polymerase chain reaction so that the nucleotide sequence targeted by the protospacer of Cas9 or Cpf1 was located in the middle region. Herein, the protospacer refers to a target nucleotide sequence in DNA of a host cell to which a gRNA can complementarily bind.

After inserting the dsDNA into pUC19 or pGEM vector through cloning, sequencing was performed using M13 primer to confirm the protospacer sequence. Substrate DNA was amplified by polymerase chain reaction using M13 primer, purified, and stored at −20° C. at a concentration of 100 ng/μl.

Example 1: Confirmation of the Activation of Nonspecific Nuclease Function of CRISPR/Cas Protein by crRNA It was confirmed that the genome editing function of the CRISPR/Cas proteins, including CRISPR/Cas12a, was activated by crRNA-guided target sequence binding, thereby activating the nonspecific nucleases function that degrade DNA or RNA molecules. A schematic diagram thereof is shown in FIG. 1.

Example 2: Recognition of Cancer Cell Specific SNP and Apoptosis of Cancer Cells by CRISPR PLUS Depending on the tissues from which a cancer is derived and the type of the cancer, cancer cells have their own chromosomal mutations including gene mutations or single nucleotide polymorphisms (SNPs) in specific genomic regions that do not exist in normal cells. These cancer-specific SNPs were used as cancer cell-specific markers of the present invention. Cancer cell-specific SNPs were used for the synthesis of crRNAs containing sequences complementary to the SNPs and were recognized by the CRISPR PLUS protein containing an CRISPR-associated protein containing the crRNA and an exonuclease. Sequence-specific binding between SNP and crRNA in the genome of cancer cells activated the genomic editing function of CRISPR PLUS protein, resulting in the breakage of target DNA/RNA. The above activation then activated the intrinsic nonspecific nuclease function of CRISPR PLUS, which irreversibly destroys the ds and ss DNA/RNA molecules in cancer cells, leading to apoptosis. These results are shown in FIG. 2 as a schematic diagram.

Example 3: Confirmation of the Endonuclease Function of SpyCas9 (SEQ ID NO: 46) (In Vitro)

NEBuffer™ 3.1 was diluted in nuclease-free purified water to final 1× concentration, and 120 nM of nuclease and 120 nM of crRNA were added thereto, followed by induction of RNP complex formation. After mixing, the mixture was incubated at room temperature for about 15 minutes. About 200 ng of substrate DNA was added thereto, and the mixture was tapped and reacted at 37° C. In order to confirm the reaction to the substrate DNA without the target sequence, DNA that cannot be targeted was added at this step. The final volume of the reaction mixture was adjusted to 20 µl. After the reaction, the gel loading dye solution was added and mixed well. After making a 2% agarose gel (Agarose, Sepro, GenDEPOT, A0224-050), 12 µl of the stained reactant was electrophoresed with a 1 kb DNA marker (Thermo Scientific, SM0311). Subsequently, the substrate DNA band cleaved by the activity of the nucleases was observed.

As a result, it was confirmed that the DNA was not cleaved when only the substrate DNA having no target sequence was reacted. However, it was confirmed that, when the target DNA was put together, all the DNA was cleaved.

Example 4: Confirmation of the Nonspecific Exonuclease Function of Cpf1 (In Vitro)

NEBuffer™ 1.1 was diluted in nuclease-free purified water to final 1× concentration, and 120 nM of CRISPR/Cas12a and 120 nM of crRNA$^{DHCR7}$ were added thereto, followed by induction of RNP complex formation. To 230 nM of RNP complex, 200 ng of substrate DNA was carefully added and the mixture was tapped and reacted at 37° C. At this time, the substrate DNA was prepared by incubating a specific or a nonspecific DNA substrate alone or a mixture of a specific DNA and a nonspecific DNA in NEBuffer 1.1 buffer for 1.5 hours or 24 hours at 37° C. The final volume of the reaction mixture was adjusted to 20 µl.

After the reaction for the desired time, a gel-loading dye was added and mixed well. After making a 2% agarose gel (Agarose, Sepro, GenDEPOT, A0224-050), 12 µl of the stained reactant was electrophoresed with a 1 kb DNA marker (Thermo Scientific, SM0311). The substrate DNA bands cleaved by the activities of nucleases were observed. The results are shown in FIG. 3.

In order to demonstrate the sequence-nonspecific exonuclease activity possessed by the CRISPR nuclease, in vitro DNA cleavage experiments were carried out using CRISPR nuclease and specific and nonspecific DNA substrates, and the results revealed that the CRISPR nuclease has a nonspecific exonuclease activity depending on the sequence-specific endonuclease activity.

Specifically, CRISPR/Cas12a, a crRNA targeting human DHCR7 gene, and a specific DNA substrate (DNA #1, 1.5 kb) with crRNA-targeted sequence, or a nonspecific DNA substrate (DNA #2, 0.5 kb) without crRNA-targeted sequence were incubated for 1.5 or 24 hours to induce DNA cleavages, which were confirmed on an agarose gel (see FIG. 3). Here, the sequences of the crRNA complementarily biding to DHCR7, dsDNA1 (1,431 bp), and dsDNA2 (544 bp) are represented by SEQ ID NO: 132, SEQ ID NO: 133, and SEQ ID NO: 134, respectively.

When the specific DNA substrate was incubated with the nuclease and the crRNA for 1.5 hours, the substrate was sequence-specifically cleaved to a fragment of about 0.7 kb (upper panel, lane 3). However, it was confirmed that the substrate was not cleaved without crRNA (upper panel, lane 4). When the incubation was carried out with nonspecific DNA under the same conditions, DNA cleavage did not occur regardless of the presence of the crRNA (upper panel, lanes 5 and 6).

When the specific DNA substrate and the nonspecific DNA substrate were simultaneously treated with nucleases, only the specific DNA substrate was cleaved as expected (top panel, lanes 7 and 8). In addition, when the incubation time for the specific DNA substrate, the nuclease and the crRNA was increased to 24 hours, it was observed that the specific DNA substrate and its fragments disappeared (lower panel, lane 3). This means that the DNA was cleaved by the exonuclease activity of the CRISPR nuclease.

When the same experiment was carried out in the absence of crRNA, the DNA did not disappeared (lower panel, lane 4), indicating that exonuclease activity was dependent on sequence-specific enzyme activity of CRISPR/Cas12a. In addition, such fact was also demonstrated from the result that DNA was retained without disappearance when non-specific DNA was treated with nucleases and crRNA for 24 hours (lower panel, lanes 5 and 6).

In addition, when specific and nonspecific DNA substrates were simultaneously treated with nuclease and crRNA for 24 hours, both specific and nonspecific DNA substrates were degraded and disappeared (lower panel, lane 7), which was observed only in the presence of crRNA (lower panel, lane 8). This implies that the exonuclease function of CRISPR/Cas12a induced by the activation of sequence-specific endonuclease function works in a sequence-nonspecific manner.

Thus, these experimental results imply that CRISPR/Cas12a has nonspecific exonuclease activity dependent on sequence-specific enzyme activity.

Example 5: Cytotoxicity Analysis

Human cancer-derived cells, HeLa cells, were cultured using DMEM/10% FBS growth medium at 37° C. in a 5% $CO_2$ incubator. One day before transfection, $2.5 \times 10^4$ cells were suspended in 100 µl of medium and plated in a 96-well plate. Blank (background control) wells were loaded with 100 µl of medium only. The next day, transfection with a complex (RNP) of CRISPR/Cas nuclease and crRNA was performed under the conditions as shown in Table 3 below. One of the crRNAs had sequence specificity to human DHCR7 gene and the other had sequence specificity to DWARFS gene of rice.

TABLE 3

| Conditions | 1 | 2 | 3 | 4 | 5 | 6 | 7 |
|---|---|---|---|---|---|---|---|
| Lipofectamine | X | O | O | O | O | O | O |
| CRISPR/Cas nuclease (CRISPR/Cas12a) | X | O | X | O (1.2 nM) | O (1.2 nM) | O (2.4 nM) | O (2.4 nM) |
| Targeting crRNA | X | X | O | O (1.2 nM) | X | O (2.4 nM) | X |
| Non-targeting crRNA | X | X | X | X | O (1.2 nM) | X | O (2.4 nM) |

For each well, 5 µl of Opti-MEM media, 2.4 nM of CRISPR/Cas, and 2.4 nM of crRNA were mixed in a 1.5 ml tube, followed by incubation at room temperature for 10 minutes. 0.17 µl of Lipofectamine Cas Plus Reagent was added to the same tube and incubated at room temperature for 5 minutes. Another tube was prepared during the incubation of the above tube. 5 µl of Opti-MEM and 0.3 µl of Lipofectamine CRISPRMAX Reagent were mixed in the tube and incubated at room temperature for 5 minutes. The contents of the two tubes were mixed and incubated at room temperature for 10 minutes. The resulting tube solution was added dropwise to each well where the cells grew. The cells were then incubated at 37° C. in a 5% CO$_2$ incubator.

After 24, 48 and 72 hours, 10 µl of WST-1 (Cell Proliferation Reagent, Roche 0501594401) was added to each well on a clean bench. Then, the plate was placed in a 5% CO$_2$ incubator at a temperature of 37° C. and color changes were observed (light red→dark red). Ten minutes later, the absorbances of the background and sample were measured at 420 to 480 nm and 690 nm using a FLUOSTAR™ Omega ELISA reader (BMG Labtech). The cytotoxicity of CRISPR/Cas nuclease in targeting and non-targeting crRNAs was analyzed.

Human-derived cancer cells, HEK293 (FIG. 4a) and HeLa (FIG. 4b), were transfected with CRISPR/Cas12a nuclease, crRNA, or a conjugate of the two molecules (RNP complex), respectively, and after 24, 48, and 72 hours, viability of cells was measured by the viability assay using WST-1. As a result, the cells transfected with nuclease or crRNA only showed substantially no change in viability at 24, 48 and 72 hours (see FIG. 4). These results indicate that the nuclease and crRNA itself are not toxic to the cells.

On the other hand, cells transfected with a conjugate having sequence-specific enzyme activity exhibited a remarkable decrease in viability at 72 hours. This result implies that the CRISPR/Cas12a nuclease exhibits toxicity to cells depending on sequence-specific enzyme activity. The cells transfected with the same conjugate showed either no change in viability (HEK293) or slight decrease in viability (HeLa) at 24 and 48 hours. This means that some time is required for the toxicity of the CRISPR/Cas12a nuclease to affect the cells.

In general, it is known that the sequence-specific enzyme activity of CRISPR/Cas nuclease proceeds steadily in the cell from 24 hours to 48 hours. Further, in view that this activity leads to nonspecific nuclease activity exhibiting cytotoxicity, it can be said that the cytotoxicity that appears after 72 hours is not an indirect effect independent of nuclease activity, but is caused by a function associated with sequence-specific enzyme activity of the nuclease. Nevertheless, it was confirmed that the use of the specific crRNA was more cytotoxic than the use of the nonspecific crRNA.

Therefore, the results of this experiment show that the CRISPR/Cas12a nuclease has a function of decreasing the cell viability by exhibiting toxicity to the cells depending on the sequence-specific enzyme activity.

Example 6: Analysis of Cancer Cell-Specific Toxicity

SNPs specifically present in cancer cells were found by analyzing the gene sequences of human-derived lung cancer cells and normal cells, and crRNAs capable of targeting them were synthesized. CRISPR nuclease and crRNA were mixed to make an RNP complex and then, cancer cells and normal cells were transfected therewith. Cancer cell-specific killing effect was analyzed using WST-1-based cell viability assay. The used crRNA was prepared so as to target a sequence (SEQ ID NO: 43) specifically present in EGFR of lung cancer.

One day before transfection, 2.5×10$^4$ cells were suspended in 100 µl of medium and plated in a 96-well plate. Blank (background control) wells were loaded with 100 µl of medium only. The next day, transfection with a complex (RNP) of CRISPR/Cas nuclease and crRNA was performed under the conditions as shown in Table 4 below.

TABLE 4

| Conditions | 1 | 2 | 3 | 4 | 5 | 6 | 7 | 8 | 9 |
|---|---|---|---|---|---|---|---|---|---|
| Lipofectamine | X | O | O | O | O | O | O | O | O |
| CRISPR/Cas nuclease | X | X | O | X | X | O (1.2 nM) | O (1.2 nM) | O (2.4 nM) | O (2.4 nM) |
| Targeting crRNA | X | X | X | O | X | O (1.2 nM) | X | O (2.4 nM) | X |
| Non-targeting crRNA | X | X | X | X | O | X | O (1.2 nM) | X | O (2.4 nM) |

For each well, 5 µl of Opti-MEM media, 2.4 nM of CRISPR/Cas, and 2.4 nM of crRNA were mixed in a 1.5 ml tube, followed by incubation at room temperature for 10 minutes. 0.17 µl of Lipofectamine Cas Plus Reagent was added to the same tube and incubated at room temperature for 5 minutes. Another tube was prepared during the incubation of the above tube. 5 µl of Opti-MEM and 0.3 µl of Lipofectamine CRISPRMAX™ Reagent were mixed in the tube and incubated at room temperature for 5 minutes. The contents of the two tubes were mixed and incubated at room temperature for 10 minutes. The resulting tube solution was added dropwise to each well where the cells grew. The cells were then incubated at 37° C. in a 5% CO$_2$ incubator.

After 24, 48 and 72 hours, 10 µl of WST-1 (Cell Proliferation Reagent, Roche 0501594401) was added to each well on a clean bench. Then, the plate was placed in a 5% CO$_2$ incubator at a temperature of 37° C. and color changes were observed (light red→dark red). Ten minutes later, the absorbances of the background and sample were measured at 420 to 480 nm and 690 nm using a FLUOSTAR™ Omega ELISA reader. The cytotoxicity of CRISPR/Cas nuclease in targeting and non-targeting crRNAs was analyzed.

As a result, it was confirmed that lung cancer cells were specifically killed only in the group treated with the targeting crRNA.

Example 7: Confirmation of Apoptotic Effect by EGFR Mutant Sequence-Specific Guide RNA In this example, it has been demonstrated that it is possible to cause multi-cleavage in the genome of HCC827 lung cancer cells using Cas9 protein expression vector (PX459, Addgene plasmid #62988), thereby inducing apoptosis. Electroporation was used to transfer the vector into the cells. To induce multi-cleavage of the genome, a guide RNA targeting the E2 mutant sequence of EGFR gene in HCC827 cell was used. The E2 mutant sequence of the EGFR gene is known to exist in more than 18 multi-copies.

HCC827 cells were cultured in a 75T flask containing RPMI-1640 (10% fetal bovine serum) medium to a confluence of about 50%, trypsinized, washed with PBS, and finally resuspended in Neon Electroporation Buffer R. After loading 150,000 cells and 500 ng of vector into a 10 μl Neon pipet tip, electroporation was carried out under the conditions of 1,300 V, 20 ms, and 2 pulses. Then, the cells were allowed to recover in RPMI-1640 (10% fetal bovine serum) medium, harvested 6 days later, and counted. The results are shown in FIGS. 5 and 6.

As shown in FIGS. 5 and 6, it was confirmed that the number of cells in the EGFR_E2 experimental group (pSpCas9(BB)-2A-Puro(PX459)V2.0-EGFR_E2) was significantly reduced compared with the EGFR_WT experimental group (pSpCas9(BB)-2A-Puro(PX459)V2.0-EGFR_WT) in which there was no target sequence, as compared with the electric pulse group. Specifically, 83% apoptosis was induced in the EGFR_E2 experimental group. From these results, it was confirmed that addition of Cas9 protein and cytogenetic sequence-specific multi-target guide RNA to cancer cells induced apoptosis of the cancer cells.

Example 8: Confirmation of Apoptotic Effects Depending on Target Positions in Lung Cancer Cell 111299

Example 8.1: Introduction of gRNA and CRISPR-Associated Protein Through Lipofection Lung cancer cells H1299 were plated in a 24-well plate at $1.5\times10^5$ cells/well. After 24 hours, DNAs of the kinds shown in Table 5 below (CCR5, HPRT1, MT2, SMIM11, GNPDA2, SLC15A5, and KCNE2) were introduced into each well. For the introduction, Lipofectamine 3000 reagent was used according to the manufacturer's manual and each 500 ng of DNA was used.

TABLE 5

| Conditions | NT1 | CCR5 | HPRT1 | MT2 | SMIM11 | GNPDA2 | SLC15A5 | KCNE2 |
|---|---|---|---|---|---|---|---|---|
| Cas9 | 500 ng | 500 ng | 500 ng | 500 ng | 500 ng | 500 ng | 500 ng | 500 ng |

After 72 hours from the time of DNA introduction, i.e., transfection, the culture solution of each well was removed by suction, and the cells were washed once with 500 μl of 1×PBS. Then, Trypsin-EDTA was applied to the wells to detach all the cells. The cells were stained with trypan blue dye, and the number of live cells was counted. The results are shown in FIGS. 7 and 8.

As shown in FIG. 8, NT (non-target), which is known to have no target sequence to cleave in H1299, and CCR5 and HPRT1 having a pair of target sites showed similar apoptotic effects. On the other hand, MT2, which is known to cut more than 100 sites, showed an apoptotic effect by reducing the amount of live cells to about 50% as compared to them. In addition, SMIM11 (about 74%), GNPDA2 (about 58%), SLC15A5 (about 45%), and KCNE2 (about 77%), which are the target sites of lung cancer cell lines, showed apoptotic effect as high as MT2. Among them, SMIM11 and KCNE2 exhibited better apoptotic effect than MT2. The copy number and essentiality of each experimental group are shown in Table 6 below, and the morphology of the cells in each experimental group was observed under a microscope and is shown in FIG. 7.

TABLE 6

| Conditions | NT1 | CCR5 | HPRT1 | MT2 | SMIM11 | GNPDA2 | SLC15A5 | KCNE2 |
|---|---|---|---|---|---|---|---|---|
| Copy number | 0 | 2 | 2 | >100 | >40 | >12 | >12 | >40 |
| Essentiality | N/A | Non-essential | House keeping | Non-essential | Non-essential | Oncogene | Oncogene | Non-essential |

Example 8.2: Introduction of gRNA and CRISPR-Associated Protein Using Lipofectamine Lung cancer cells of H1299 were plated in a 24-well plate at $1.5 \times 10^5$ cells/well. After 24 hours, DNAs of the kinds shown in Table 7 below were introduced into each well. For the introduction, Lipofectamine 3000 reagent was used according to the manufacturer's manual and each 500 ng of DNA was used.

TABLE 7

| Conditions | Lipo only | NT1 | CCR5 | HPRT1 | MT2 | GNPDA2 | SLC15A5 | KCNE2 |
|---|---|---|---|---|---|---|---|---|
| Copy number | N/A | 0 | 2 | 2 | >100 | >12 | >12 | >40 |
| Essentiality | N/A | N/A | Non-essential | House-keeping | Non-essential | Oncogene | Oncogene | Non-essential |

After 48 hours from the time of DNA introduction, i.e., transfection, the culture solution of each well was removed by suction, and the cells were washed once with 500 μl of 1×PBS. Then, Trypsin-EDTA was applied to the wells to detach all the cells. The cells were stained with trypan blue dye, and the number of live cells was counted. The results are shown in FIGS. 9 and 10. In this example, an experiment group in which only lipofection was performed without introducing DNA was included.

As shown in FIG. 9, the number of live cells in CCR5 decreased to about 80% as compared to that of lipofection only (Lipo only). Those of NT1 and HPRT1 were about 70% compared to that of CCR5. In MT2, the number of cells was decreased to about 25% compared to that of NT1. In CNV-targeted three kinds (GNPDA2, SLC15A5, and KCNE2), more cells died, and it was not possible to significantly detect live cells by cell counting using trypan blue. Specifically, about 43%, about 23%, about 50%, about 86%, about 99%, about 99%, and about 99% of the apoptosis rate was shown in NT1, CCR5, HPRT1, MT2, GNPDA2, SLC15A5, and KCNE2.

NT1 and GNPDA2 experimental groups were selected as representatives of the experimental group with a large number of live cells and the experimental group with a large number of dead cells, respectively. Thereafter, NUCBLUE LIVE READYPROBES™ Reagent and PROPIDIUM IODIDE READYPROBES™ Reagent were used to image each well under a microscope. The results are shown in FIG. 10. The proportions of live cells were analyzed by fluorescence and the results were similar to those shown in FIG. 9.

Example 9: Confirmation of Apoptotic Effects Depending on Target Positions in Lung Cancer Cell 111563

H1563 cells were plated in a 24-well plate at $1.5 \times 10^5$ cells/well and, after 24 hours, DNAs of the kinds shown in Table 8 below were introduced into each well. For the introduction, LIPOFECTAMINE™ 3000 reagent was used according to the manufacturer's manual and each 500 ng of DNA was used.

After 24 hours from the time of DNA introduction, i.e., transfection, puromycin was added to each well at a concentration of 1 μg/ml and selection was made for 72 hours. Then, the culture solution of each well was removed by suction, and the cells were washed once with 500 μl of 1×PBS. Thereafter, Trypsin-EDTA was applied to the wells to detach all the cells. The cells were stained with trypan blue dye, and the number of live cells was counted. The results are shown in FIG. 11.

As shown in FIG. 11, small amounts of cells remained, about 52% in HPRT1, about 43% in MT2, and about 37% and 40% in the two CNV-targeted kinds (IRX1 and ADAMTS16), respectively, as compared to single target CCR5. From these result, it was confirmed that the apoptotic effect can be enhanced by inducing a large amount of double strand breaker (DSB) as compared to a single target such as CCR5.

Example 10: Confirmation of Apoptotic Effects Depending on Target Positions in Lung Cancer Cell A549

Example 10.1: Confirmation of the Apoptosis of A549 Cells by Multi Targets 500 ng of DNA expressing Cas9 protein and gRNA was introduced into the cells of lung cancer cell line A549 by electroporation (Lonza). A549 cells in culture were washed with 1×PBS, and then treated with trypsin-EDTA to detach them from the bottom. The required number of cells were taken, washed once with 1×PBS, suspended in SF buffer (Lonza), and then mixed with each DNA. The mixture of the cell and the DNA was placed in an electroporator (Lonza) and electric shock was applied. As controls, conditions that target NT1, which is not aligned in the human gene sequence; HPRT1, a house keeping gene of 1 copy; and CCR5, a gene of 1 copy, respectively, and a condition of electric shock only (pulse only) were used.

After introducing DNA by electric shock, the cells were plated in a 24-well plate in two replicates and in a 96-well plate in three replicates. After 24, 42, and 72 hours from DNA introduction, 50 μl of CELLTITER GLO™ reagent was added to each well of the 96-well plate. The plates were placed on a FLUOSTAR™ omega reader and shaken for 2 minutes. After reacting them at room temperature for 10 minutes, luminescence was measured. The above method is a method of determining the amount of live cells that are undergoing metabolic processes based on the amount of ATP in the cell through the degree of luminescence. The results are shown in FIG. 12.

TABLE 8

| Conditions | CCR5 | HPRT1 | MT2 | IRX1 | ADAMTS16 |
|---|---|---|---|---|---|
| Copy number | 2 | 2 | >100 | >8 | >7 |
| Essentiality | Non-essential | House keeping | Non-essential | Non-essential | Non-essential |

As shown in FIGS. 12, 20% to 50% of apoptosis was induced over time in the MT2 condition targeting 100 or more sites, as compared to the three controls (NT1, HPRT1, and CCR5).

24 hours after the introduction of the DNA, 1 µg/ml of puromycin was added to each well of the 24-well plate. At the time of apoptosis of about 90% under the condition of only electric shock, the cell culture medium was changed to allow the cells to recover. After 5 to 7 days of recovery, the cells were detached from each well and stained with trypan blue, and the number of live cells was counted. The results are shown in FIG. 13. On the other hand, the photographs observed with a microscope before the counting of cell number, after DNA introduction and selection using puromycin, are shown in FIG. 14.

As a result, the cells did not survived under conditions of only electric shock without puromycin resistance, which became a control, and when CCR5 was targeted, about 50% apoptosis was observed as compared to the NT1 and HPRT1 conditions. And it was confirmed that about 90% of the cells died under MT2 condition. After the DNA was introduced, the cells were selected with puromycin and then observed under a microscope before counting the number of cells. Similar to the results of cell counting, more than 50% of the cells recovered when targeting HPRT1 and CCR5, which had only one copy, as compared to the NT1 control. On the other hand, under the MT2 condition, about 90% of the cells were killed and only 10% of the cells recovered (Blue arrow: recovered cell colony). Therefore, it was confirmed that apoptosis was induced when multi-DNA breaks were induced in A549 cells using Cas9 protein.

Example 10.2: Confirmation of the Apoptosis of A549 Cells by CNV Target

DNA break was induced with Cas9 protein by targeting a gene having CNV in the cells of lung cancer cell line A549 and the degree of apoptosis was examined. Specifically, 500 ng of DNA expressing Cas9 protein and each CNV-targeting gRNA was introduced into the A549 cells by electroporation (Lonza). A549 cells in culture were washed with 1×PBS, and then treated with trypsin-EDTA to detach them from the bottom. The required number of cells were taken, washed once with 1×PBS, suspended in SF buffer (Lonza), and then mixed with each DNA. The mixture of the cell and the DNA was placed in an electroporator (Lonza) and electric shock was applied. As controls, a condition of introducing pET21a vector capable of expressing a protein in *E. coli*, a condition of electric shock only (pulse only), and a condition of no treatment (no pulse) were added.

After introducing DNA by electric shock, the cells were plated in a 96-well plate in three replicates per condition. After 24, 44, and 51 hours of DNA introduction, 50 µl of CELLTITER GLO™ reagent was added to each well. The plate was placed on a FLUOSTAR OMEGA™ reader and shaken for 2 minutes. After reacting them at room temperature for 10 minutes, luminescence was measured. The results are shown in FIG. 15.

As shown in FIGS. 15, 20% to 50% of apoptosis was induced over time in the MT2 condition targeting 100 or more sites, as compared to the three controls (pulse only, pET21a, and no pulse). In addition, the three CNV targets of CD68, DACH2, and HERC2P2 induced MT2-like apoptosis, and the CNV target of SHBG induced 70% to 80% of apoptosis compared to the control. Accordingly, it was confirmed that apoptosis was induced when the target DNA break was induced using Cas9 protein for the four kinds of CNVs (CD68, DACH2, HERC2P2, and SHBG) in A549 cells.

Example 11: Confirmation of Apoptotic Effects Depending on Target Positions in Breast Cancer Cell SKBR3

Example 11.1: Confirmation of the Apoptosis of SKBR3 Cells by CNV Target 500 ng of DNA expressing Cas9 protein and each CNV-targeting gRNA was introduced into the cells of breast cancer cell line SKBR3 by electroporation (Lonza). SKBR3 cells in culture were washed with 1×PBS, and then treated with trypsin-EDTA to detach them from the bottom. The required number of cells were taken, washed once with 1×PBS, suspended in SF buffer (Lonza), and then mixed with each DNA. The mixture of the cell and the DNA was placed in an electroporator (Lonza) and electric shock was applied. As controls, a condition that target NT1 which is not aligned in the human gene sequence (non-target), a condition of electric shock only (pulse only), and a condition of no treatment (no pulse) were added. After introducing DNA by electric shock, the cells were put into a 24-well plate in two replicates and into a 96-well plate in three replicates.

After 24, 42, and 48 hours of DNA introduction, 50 µl of CELLTITER GLO™ reagent was added to each well of the 96-well plates. The plates were placed on a FLUOSTAR OMEGA™ reader and shaken for 2 minutes. After reacting them at room temperature for 10 minutes, luminescence was measured. The results are shown in FIG. 16.

As shown in FIG. 16, 30% of apoptosis was induced over time in the MT2 condition targeting 100 or more sites, as compared to the three controls (NT1, pulse only, and no pulse). In addition, the two CNV targets of ERBB2 and KRT16 induced 40% to 50% of apoptosis compared to the controls.

Example 11.2: Confirmation of the Apoptosis of SKBR3 Cells by CNV Target 500 ng of DNA expressing Cas9 protein and each CNV-targeting gRNA was introduced into the cells of breast cancer cell line SKBR3 by electroporation (Lonza). SKBR3 cells in culture were washed with 1×PBS, and then treated with trypsin-EDTA to detach them from the bottom. The required number of cells were taken, washed once with 1×PBS, suspended in SF buffer (Lonza), and then mixed with each DNA. The mixture of the cell and the DNA was placed in an electroporator (Lonza) and electric shock was applied. As controls, conditions that target NT1 which is not aligned in the human gene sequence and HPRT1 which is a house keeping gene of 1 copy, were used. After introducing DNA by electric shock, the cells were put into a 24-well plate in two replicates.

48 hours after the introduction of the DNA, the cells were detached from each well of the 24-well plate and stained with trypan blue, and the number of live cells was counted. The results are shown in FIG. 17. As shown in FIG. 17, 40% of apoptosis was induced over time in the MT2 condition targeting 100 or more sites, as compared to the controls, and the two CNV targets of ERBB2 and KRT16 induced 40% to 50% of apoptosis compared to the controls. Accordingly, it was confirmed that apoptosis was induced when the target DNA break was induced using Cas9 protein for the two kinds of CNVs (ERBB2 and KRT16) in SKBR3 cells.

Example 12: Confirmation of Apoptotic Effects Depending on Target Positions in Cervical Cancer Cell HeLa

Example 12.1: Confirmation of Apoptosis by CNV Target and HPV Gene Target 600 ng of a vector expressing Cas9 protein and gRNA was introduced into the cells of cervical cancer cell line HeLa by electroporation. HeLa cells in culture were washed with 1×PBS, and then treated with trypsin-EDTA to detach them from the bottom. The required number of cells were taken, washed once with 1×PBS, suspended in SF buffer (Lonza), and then mixed with each vector. The mixture of the cell and the DNA vector was placed in an electroporator (Lonza) and electric shock was applied. As controls, a condition that target CCR5 which is a non-essential gene of 2 copies and MT2 condition that target more than 100 non-essential genes were used. For experimental groups, experiments were carried out to induce HeLa cell-specific apoptosis by targeting PRDM9, which is known to exist in 8 copies or more, and a human papillomavirus (HPV)-derived gene, which is known to exist in 30 copies or more in HeLa cell.

After introducing DNA by electric shock, the cells were put into a 24-well plate in two replicates. 24 hours thereafter, 0.5 µg/ml of puromycin was added to each well to conduct a selection process killing the cells without the DNA vector. After 3 days of selection, the culture was carried out with changing the culture medium to a puromycin-free one. After 3 to 4 days, the cells were detached from each well and stained with trypan blue, and the number of live cells was counted. The results are shown in FIGS. 18 and 19.

As shown in FIGS. 18 and 19, it was confirmed that about 50% of apoptosis was induced over time by the MT2 condition targeting 100 or more sites as compared to CCR5, which cuts only one site in HeLa cells. In addition, it was confirmed that the CNV target PRDM9 and the HPV gene target HPV_1 induce apoptosis similar to or more than the MT2 condition. Specifically, in FIG. 18, MT2 and PRDM9 exhibited apoptosis rates of about 50% and about 80%, respectively. Also, in FIG. 19, about 50%, about 40%, and about 40% of apoptosis rates were seen in MT2, PRDM9, and HPV_1. Accordingly, it was confirmed that apoptosis was induced when the target DNA break was induced using Cas9 protein for CNV and HPV genes existing only in HeLa cells.

Example 12.2: Confirmation of Apoptosis by CNV Target and HPV Gene Target

The process of introducing the DNA vector into HeLa cells by electric shock was the same as in Example 12.1. After introducing DNA by electric shock, the cells were put into a 96-well plate in two replicates. At 24, 48, and 72 hours thereafter, the amount of ATP in the cells was measured using CELLTITER GLO™ 2.0 to determine the amount of live cells that are undergoing metabolic processes through the degree of luminescence. As controls, a control vector expressing GFP, a condition that target CCR5 which is a non-essential gene of 1 copy, and MT2 condition that target more than 100 non-essential genes were added. For experimental groups, experiments were carried out to induce HeLa cell-specific apoptosis by targeting PRDM9, which is known to exist in 8 copies or more, and a human papillomavirus (HPV)-derived gene, which is known to exist in 30 copies or more in HeLa cell. The results are shown in FIG. 20*a*.

As shown in FIG. 20*a*, the CCR5 target that cuts only one site in HeLa cells and the Pulse only control containing GFP showed a similar luminescence signal. In addition, it was confirmed that about 50% of apoptosis was induced by the MT2 condition as compared to the CCR5 condition. Further, it was confirmed that the CNV target PRDM9 and the HPV gene target HPV_1 induce apoptosis more than the MT2 condition. Specifically, MT2, PRDM9, and HPV_1 exhibited apoptosis rates of about 50%, about 65%, and about 65%, respectively.

Accordingly, it was confirmed that apoptosis was induced when the target DNA break was induced using Cas9 protein for CNV and HPV genes existing only in HeLa cells.

Example 12.3: Confirmation of Apoptosis by HPV Gene Target

The process of introducing the DNA vector into HeLa cells by electric shock was the same as in Example 12.1. To the existing condition that target CCR5 which is a non-essential gene of 1 copy and the MT2 condition that target more than 100 non-essential genes, NT conditions targeting areas that is not present in the human genome were added. NT1 is a condition of expressing a 20-mer non-target sgRNA, and NT2 and NT3 are conditions wherein the length of the spacer of a non-target sgRNA are 10 mer and 5 mer, respectively. For experimental groups, experiments were carried out to induce HeLa cell-specific apoptosis by targeting a human papillomavirus (HPV)-derived gene, which is known to exist in 30 copies or more in HeLa cell. After introducing DNA by electric shock, the cells were put into a 24-well plate in two replicates. 24 hours thereafter, 0.5 µg/ml of puromycin was added to each well to conduct a selection process killing the cells without the DNA vector. After 3 days of selection, the culture was carried out with changing the culture medium to a puromycin-free one. After 10 days, the cells were detached from each well and luminescence signal was measured by CELLTITER GLO™ method. The results are shown in FIG. 20*b*.

As shown in FIG. 20*b*, the CCR5 target that cuts only one site in HeLa cells showed about 75% luminescence signal as compared to the NT3 condition having a 5-mer spacer and about 99.5% apoptosis was induced in MT2 condition as compared to the NT3 condition. In addition, it was confirmed that about 50% of apoptosis was induced by the MT2 condition as compared to the CCR5 condition. In addition, HPV_1, an HPV gene target, was found to kill about 90% of cells as compared to the NT3 condition. Accordingly, it was confirmed through CellTiter Glo method that apoptosis was induced when the target DNA break was induced using Cas9 protein for HPV genes existing only in HeLa cells.

Example 13: Confirmation of Apoptotic Effects Depending on Target Positions in Colorectal Cancer Cell HT-29

Example 13.1: Confirmation of Apoptosis by CNV Target

HT-29 cells were plated in a 24-well plate at $1.5 \times 10^5$ cells/well. After 24 hours, DNAs of the kinds shown in Table 9 below were introduced into each well. For the introduction, LIPOFECTAMINE™ 3000 reagent was used according to the manufacturer's manual and each 500 ng of DNA was used.

TABLE 9

| Conditions | Lipo | GFP | NT1 | CCR5 | HPRT1 | MT2 | TRAPPC9 | LINC00536 | TRPS1 | CDK8 |
|---|---|---|---|---|---|---|---|---|---|---|
| Copy number | N/A | 0 | 2 | 2 | 2 | >100 | >13 | >9 | >8 | >18 |
| Essentiality | N/A | N/A | N/A | Non-essential | House-keeping | Non-essential | Non-essential | Non-essential | Non-essential | Oncogene |

After 24 hours from the time of DNA introduction, i.e., transfection, puromycin was added to each well at a concentration of 1 μg/ml and selection was carried out for 90 hours. Then, the culture solution of each well was removed by suction, and the cells were allowed to recover in normal media (McCOY+10% FBS, 1% P/S) for 12 days. Then, the cells were washed once with 500 μl/well of 1×PBS and Trypsin-EDTA was applied to the wells to detach all the cells. The cells were stained with trypan blue dye, and the number of live cells was counted twice and then averaged. The results are shown in FIG. 21.

As shown in FIG. 21, NT1, which is known to have no target sequence, and CCR5, which has a single target, showed differences within the error range. In the case of HPRT1, about 47% of the cells survived as compared to NT1. MT2, which is positive control that cut over 100 repeat sequences in the entire genome, and four CNV targets (TRAPPC9, LINC00536, TRPS1, and CDK8) exhibited cell survival rates of 2%, 3%, 18%, 20%, and 4.2%, respectively, as compared to NT1. That is, it was confirmed that cancer cells can be effectively killed by using the CNV target.

Example 13.2: Confirmation of the Apoptosis of Colorectal Cancer Cell by CNV Target In order to identify the specific apoptosis of HT-29 (colon cancer cell line) by targeting four genes with CNV (CDK8, LINC00536, TRPS1, and TRAPPC9) and MT2, 500 ng of DNA expressing Cas9 protein and each CNV-targeting gRNA was introduced into the HT-29 cells by electroporation (Lonza). HT-29 cells in culture were washed with 1×PBS, and then treated with trypsin-EDTA to detach them from the bottom. The required number of cells were taken, washed once with 1×PBS, suspended in SF buffer (Lonza), and then mixed with each DNA. The mixture of the cells and the DNA was placed in an electroporator (Lonza) and electric shock was applied. As controls, a condition that target NT1 which is not aligned in the human genome (non-target) and a condition of electric shock only (pulse only) were added. After electric shock, the cells were put into a 96-well plate in four replicates per condition. After 24 hours of DNA introduction, 50 μl of CELLTITER GLO™ reagent was added to each well. The plate was placed on a FLUOSTAR OMEGA™ reader and shaken for 2 minutes. After reacting at room temperature for 10 minutes, luminescence was measured. The results are shown in FIG. 22.

As shown in FIG. 22, compared to the control group, 90% of apoptosis was induced in the MT2 condition targeting 100 or more sites and TRAPPC9 CNV target condition, and 20% to 45% of apoptosis was induced by the three CNV targets of CDK8, LINC00536, and TRPS1.

Example 14: Comparison of Apoptotic Effects of the Target Genes Used in 111299 in Lung Cancer Cell 111563

H1563 cells were plated in a 24-well plate at 1.5×10⁵ cells/well. After 24 hours, DNAs of the kinds shown in Table 10 below were introduced into each well. For the introduction, LIPOFECTAMINE™ 3000 reagent was used according to the manufacturer's manual and each 500 ng of DNA was used.

TABLE 10

| Conditions | CCR5 | SMIM11 | GNPDA2 | SLC15A5 | KCNE2 |
|---|---|---|---|---|---|
| Cut number | 2 | 2 | 2 | 2 | 2 |
| Essentiality | Non-essential | Non-essential | oncogene | oncogene | Non-essential |

After 24 hours from the time of DNA introduction, i.e., transfection, puromycin was added to each well at a concentration of 1 μg/ml and selection was made for 72 hours. Then, the culture solution of each well was removed by suction, the cells were washed once with 500 μl/well of 1×PBS, and Trypsin-EDTA was applied to the wells to detach all the cells. The cells were stained with trypan blue dye, and the number of live cells was counted. The results are shown in FIG. 23. At this time, all of the used DNA targets, except for CCR5, were amplified in H1299 and showed apoptotic effects by cutting more than 12 sites on the genome (see FIGS. 8 and 9). However, since such amplified CNVs do not exist in H1563 cells, all of the targets cut only two target positions, as in the case of CCR5.

As shown in FIG. 23, in the lung cancer cell H1563, these targets did not exhibit apoptotic effect as in H1299 lung cancer cell, but showed rather higher cell survival rates in comparison with CCR5. However, in the case of KCNE2, it was observed to exhibit a high apoptotic effect also in H1563. This was consistent with the apoptotic trend inferred from the microscopic image of FIG. 24. The apoptotic effect of KCNE2 was presumed to have occurred for unknown reasons, and the three CNV targets (SMIM11, GNPDA2, and SLC15A5) of H1299, except for KCNE2, did not induce apoptosis in H1563. Therefore, the cell-specific apoptotic effect of CNV was confirmed.

Example 15: Measurement of Apoptosis of Lung Cancer Cell 111299 by CNV Target

One day before transfection, the cells of lung cancer cell line H1299 were detached with trypsin-EDTA and plated in a white 96-well plate at 1.3×10⁴ cells/well. The next day, 500 ng of DNA expressing Cas9 protein and each CNV-targeting gRNA was introduced into the cells by a method using liposome.

0.3 μl of liposome reagent I and 5 μl of OPTI-MEM™ were mixed (tube 1). 0.2 μl of liposome reagent II, 5 μl of OPTI-MEM™, and 500 ng of DNA of each condition were mixed to prepare tube 2. The contents of the two tubes were mixed and left at room temperature for 15 minutes. The mixture of liposome and DNA was added to the wells of a 96-well plate at 11 μl/well. After 3 hours, AnnV reagent was added to the wells and the degree of luminescence was measured after 24 hours of transfection. The results are shown in FIG. 25. This method is a method of measuring the degree of apoptosis according to the degree of luminescence occurring when AnnV attaches to the PS (phosphatidylserine) site exposed to the outer cell membrane upon apoptosis.

As a result of the experiment, KCNE2, GNPDA2, SMIM11, and SLC15A5 showed about 30% to 40% apoptosis rates. From the above results, when the target DNA break was induced using Cas9 protein in the four CNVs (GNPDA2, KCNE2, SLC15A5, and SMIM11) of H1299 cells, it was confirmed that apoptosis was caused by the exposure of PS to the cell membrane.

Example 16: Confirmation of Apoptotic Effect by EGFR Mutant Sequence-Specific Guide RNA and Apoptotic Effect Using Cas9-RecJ Fusion Protein (CRISPR PLUS)

In this example, it has been demonstrated that it is possible to cause multi-cleavage in the genome of HCC827 lung cancer cells using Cas9 protein expression vector (PX459, Addgene plasmid #62988), thereby inducing apoptosis. Furthermore, it was confirmed that the apoptotic effect can be amplified by expressing the human codon-optimized Rec J protein together with the Cas9 protein by the PX459 vector. Electroporation was used to transfer the vectors into the cells and, to induce multi-cleavage of the genome, a guide RNA targeting the E2 mutant sequence of EGFR gene in HCC827 cell was used.

HCC827 cells were cultured in a 75T flask containing RPMI-1640 (10% fetal bovine serum) medium to a confluence of about 50%, trypsinized, washed with PBS, and finally resuspended in Neon Electroporation Buffer R. After loading 150,000 cells and 500 ng of vector into a 10 μl Neon pipet tip, electroporation was carried out under the conditions of 1,300 V, 20 ms, and 2 pulses. Then, the cells were allowed to recover in RPMI-1640 (10% fetal bovine serum) medium, harvested 4 days later, and counted. The results are shown in FIGS. 26 and 27.

As shown in FIGS. 26 and 27, the number of cells in the EGFR_E2 experimental group was significantly reduced as compared to the EGFR_WT experimental group in which there was no target sequence, when compared to the control group where only electric pulse was applied (pulse only). Specifically, there was no change in cell number in the experimental group wherein CCR5 was targeted by using Cas9, but the experimental group wherein EGFR_E2 was targeted exhibited apoptosis rate of about 33%. In addition, it was observed that, when the Rec J protein was co-expressed, not only the apoptotic effect was amplified by multi-cleavage but also the cell number was decreased even when the single target was cleaved. Specifically, the experimental group wherein CCR5 was targeted by using Cas9-RecJ exhibited apoptosis rate of about 50%, while the experimental group wherein EGFR_E2 was targeted by using Cas9-RecJ showed apoptosis rate of about 80%. Through the above experiments, it was found that when the Cas9 protein and the cell genome sequence-specific multi-target guide RNA were introduced to the cancer cells, apoptosis was induced and the effect could be controlled by CRISPR PLUS protein.

Example 17: Confirmation of Apoptotic Effect by EGFR Mutant Sequence-Specific Guide RNA and Apoptotic Effect Using RNP In this example, it has been demonstrated that it is possible to cause multi-cleavage in the genome of HCC827 lung cancer cells using Cas9/sgRNA ribonucleoprotein (Cas9 RNP), thereby inducing apoptosis. Electroporation was used to transfer the RNPs into the cells and, to induce multi-cleavage of the genome, a guide RNA targeting the E2 mutant sequence of EGFR gene in HCC827 cell was used.

HCC827 cells were cultured in a 75T flask containing RPMI-1640 (10% fetal bovine serum) medium to a confluence of about 50%, trypsinized, washed with PBS, and finally resuspended in Neon Electroporation Buffer R. After loading 150,000 cells and 1.2 μM of RNP into a 10 μl Neon pipet tip, electroporation was carried out under the conditions of 1,300 V, 20 ms, and 2 pulses. Then, the cells were allowed to recover in RPMI-1640 (10% fetal bovine serum) medium, harvested 1 day later, and counted. The results are shown in FIG. 28.

As shown in FIG. 28, the number of cells in the experimental group introducing RNPs targeting the EGFR_E2 sequence was significantly reduced as compared to the control group where only electric pulse was applied (pulse only), or the control groups introduced with the Cas protein or the guide RNA alone. Specifically, the experimental group wherein the RNP targeting the EGFR_E2 sequence was introduced exhibited apoptosis rate of about 33%. Through the above experiments, it was confirmed that when the Cas9 protein and the cell genome sequence-specific multi-target guide RNA were introduced to the cancer cells, apoptosis was induced and the effect could be controlled by Cas9 RNP.

Example 18: Confirmation of Apoptotic Effect by MT2 Sequence-Specific Guide RNA and Apoptotic Effect Using RNP In this example, it has been demonstrated that it is possible to cause multi-cleavage in the genome of H1563 lung cancer cells using Cas9/sgRNA ribonucleoprotein (Cas9 RNP), thereby inducing apoptosis. Electroporation was used to transfer the RNPs into the cells and, to induce multi-cleavage of the genome, a guide RNA targeting MT2, which is capable of targeting more than 100 sites in the human genome, was used.

H1563 cells were cultured in a 75T flask containing RPMI-1640 (10% fetal bovine serum) medium to a confluence of about 50%, trypsinized, washed with PBS, and finally resuspended in Neon Electroporation Buffer R. After loading 150,000 cells and 1.2 μM of RNP into a 10 μl Neon pipet tip, electroporation was carried out under the conditions of 1,200 V, 20 ms, and 2 pulses. Then, the cells were allowed to recover in RPMI-1640 (10% fetal bovine serum) medium, harvested 2 days later, and counted. The results are shown in FIG. 29.

As shown in FIG. 29, it was confirmed that the number of cells in the experimental group introduced with the RNP targeting the MT2 sequence was significantly reduced, as compared to the control group where only electric pulse was applied (pulse only) or the control group introduced with the guide RNA alone. Specifically, the experimental group introduced with the RNP targeting the MT2 sequence exhibited apoptosis rate of about 35%. Through the above experiments, it was confirmed that when the Cas9 protein and the cell genome sequence-specific multi-target guide RNA were introduced to the cancer cells, apoptosis was induced and the effect could be controlled by RNP.

Example 19: Confirmation of Apoptotic Effect by MT2, GNPDA2, and SMIM11 Sequence-Specific Guide RNAs and Apoptotic Effect Using RNP In this example, it has been demonstrated that it is possible to cause multi-cleavage in the genome of H1299 cells, which are lung cancer cells, using Cas9 protein, thereby inducing apoptosis. Among the various cancer cells, H1299 cells with relatively high transfection efficiency were used for the experiment and electroporation was used to transfer the RNPs into the cells.

As guide RNAs for inducing multi-cleavage of the genome, three kinds of guide RNAs targeting the following genes were used: MT2, GNPDA2, and SMIM11. Based on the H1299 cell-specific genomic sequencing information, guide RNAs respectively targeting an oncogene (GNPDA2) present in about 12 copies or more and a non-essential gene (SMIM11) present in about 40 copies or more, among the genes with high copy number variation (CNV), were prepared. All Cas9 protospacer adjacent motifs (PAM, 5'-NGG-3') present in the human genome sequence were analyzed and a guide RNA targeting MT2, which is capable of targeting more than 100 sites, was constructed. In order to confirm transfection, Cas9 protein with GFP at the C-terminus was constructed and used.

H1299 cells were cultured in a 75T flask containing RPMI-1640 (10% fetal bovine serum) medium to a confluence of about 50%, trypsinized, washed with PBS, and finally resuspended in Neon Electroporation Buffer R. After loading 150,000 cells and a RNP complex made of 1.2 µM of Cas9-GFP protein and 1.5 µM guide RNA into a 10 µl Neon pipet tip, electroporation was carried out under the conditions of 1,300 V, 20 ms, and 2 pulses. Then, the cells were allowed to recover in RPMI-1640 (10% fetal bovine serum) medium, and, 2 days later, the number of live cells was determined based on the live cell signal (luminescence) measured using CELLTITER GLO™ 2.0 of Promega and compared to each other. The results are shown in FIGS. 30 to 32.

As shown in FIGS. 30 to 32, no significant apoptosis was observed in the CCR5 target experimental group which was known to have a single target, as compared to the controls introduced with the protein or the guide RNA only. However, significant apoptosis was observed in the MT2, GNPDA2, and SMIM11 experimental groups that were introduced with RNPs causing multi-cleavage. Specifically, the MT2, GNPDA2, and SMIM11 experimental groups introduced with the RNPs exhibited apoptosis rates of about 33%, about 71%, and about 40%, respectively. Through the above experiments, it was confirmed that when the Cas9 protein and the cell genome sequence-specific multi-target guide RNA were introduced to the cancer cells, apoptosis was induced and the effect could be controlled by RNP.

Example 20: Confirmation of Sequence-Specific Apoptotic Effect Using Cas12a Protein and Mutant CNV Sequence-Specific Apoptotic Effect In this example, it has been demonstrated that it is possible to cause double- or multi-cleavage in the genome of HCC827 cells, which are lung cancer cells, using Cas12a protein expression vector, thereby inducing apoptosis. In the present invention, the DNA and amino acid sequences of Cas12a are represented by SEQ ID NOs: 135 and 136. Electroporation was used to transfer the vectors into the cells and a wild-type non-essential gene, CCR5 (SEQ ID NO: 138) or a crRNA (SEQ ID NO: 139) targeting an EGFR_E2 mutant sequence known to be present in HCC827 cells over 18 copies were used.

HCC827 cells were cultured in a 75T flask containing RPMI-1640 (10% fetal bovine serum) medium to a confluence of about 50%, trypsinized, washed with PBS, and finally resuspended in Neon Electroporation Buffer R. After loading 150,000 cells and 500 ng of vector into a 10 µl Neon pipet tip, electroporation was carried out under the conditions of 1,300 V, 20 ms, and 2 pulses. Then, the cells were allowed to recover in RPMI-1640 (10% fetal bovine serum) medium, harvested 6 days later, and the cells were quantified by measuring the luminescence signal. On the other hand, the EGFR_WT sequence (SEQ ID NO: 137) used as a control is a sequence known to be absent in HCC827 cells. The results are shown in FIGS. 33 and 34.

As shown in FIGS. 33 and 34, about 76% of the cells were killed in the experimental group that targets CCR5, and about 83% of the cells were killed in the experimental group that targets EGFR_E2, as compared with the control group. It was confirmed by this experiment that target specific apoptosis can be induced when the cancer cell-specific sequence, regardless of the copy number, is cleaved using Cas12a protein.

The invention claimed is:

1. A method of treating a cancer in a subject in need thereof comprising administering an effective amount of a composition to the subject,
wherein the composition comprises a vector containing (a) an isolated polynucleotide complementarily binding to a nucleic acid specifically present in cancer cells; (b) an isolated polynucleotide encoding an endonuclease; and (c) an isolated polynucleotide encoding an exonuclease, and
wherein the exonuclease is selected from the group consisting of RecBCD, RecE, RecJ, T5, Exo I, Exo III, Exo VII, Lexo, TREX2, Exoribonuclease T, TREXI, Mungbean exonuclease, Lambda, and a combination thereof,
wherein the nucleic acid specifically present in cancer cells is selected from the genes of which copy number variation (CNV) is at least 4,
wherein the endonuclease is a clustered regularly interspaced short palindromic repeat (CRISPR)-associated protein selected from a group consisting of Cas1, Cas1B, Cas2, Cas3, Cas4, Cas5, Cas6, Cas7, Cas8, Cas9, Cas10, Cas12a, Cas12b, Cas12c, Cas12d, Cas12e, Cas12g, Cas12h, Cas12i, Cas13a, Cas13b, Cas13c, Cas13d, Cas14, Csy1, Csy2, Csy3, Cse1, Cse2, Csc1, Csc2, Csa5, Csn2, CsMT2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4, and wherein the endonuclease and the exonuclease are of a fusion protein.

2. The method of claim 1, wherein the administration is via any one route selected from the group consisting of intratumoral, intravenous, intramuscular, intradermal, subcutaneous, intraperitoneal, intra-arteriolar, intraventricular, intralesional, intrathecal, topical, and a combination thereof.

3. The method of claim 1, wherein the nucleic acid specifically present in cancer cells is a single nucleotide polymorphism (SNP), a copy number variation (CNV), a structural variation (SV), a gene insertion, or a gene deletion.

4. The method of claim 3, wherein the structural variation is an inversion, a translocation, or a short nucleotide repeat expansion.

5. The method of claim 1, wherein the nucleic acid specifically present in cancer cells is selected from the genes of which copy number variation (CNV) is at least 7.

6. The method of claim 3, wherein the nucleic acid specifically present in cancer cells is a mutant of any one gene selected from the group consisting of p53, PTEN, APC, MSH2, HBV, HCV, and EGFR.

\* \* \* \* \*

SEQUENCE LISTING

```
<160> NUMBER OF SEQ ID NOS: 139

<210> SEQ ID NO 1
<211> LENGTH: 19
<212> TYPE: DNA
<213> ORGANISM: Artificial Sequence
<220> FEATURE:
<223> OTHER INFORMATION: T7 promoter

<400> SEQUENCE: 1
taatacgact cactatagg                                              19

<210> SEQ ID NO 2
<211> LENGTH: 76
<212> TYPE: DNA
<213> ORGANISM: Artificial Sequence
<220> FEATURE:
<223> OTHER INFORMATION: crRNA scaffold

<400> SEQUENCE: 2
gttttagagc tagaaatagc aagttaaaat aaggctagtc cgttatcaac ttgaaaaagt    60
```

-continued

```
ggcaccgagt cggtgc                                                   76
```

<210> SEQ ID NO 3
<211> LENGTH: 111
<212> TYPE: DNA
<213> ORGANISM: Artificial Sequence
<220> FEATURE:
<223> OTHER INFORMATION: T7 promoter-vector sequence-crRNA scaffold

<400> SEQUENCE: 3

```
taatacgact cactataggt gagaccgagg tctcggtttt agagctagaa atagcaagtt   60
aaaataaggc tagtccgtta tcaacttgaa aaagtggcac cgagtcggtg c           111
```

<210> SEQ ID NO 4
<211> LENGTH: 215
<212> TYPE: PRT
<213> ORGANISM: Artificial Sequence
<220> FEATURE:
<223> OTHER INFORMATION: Exoribonuclease T

<400> SEQUENCE: 4

```
Met Ser Asp Asn Ala Gln Leu Thr Gly Leu Cys Asp Arg Phe Arg Gly
1               5                   10                  15

Phe Tyr Pro Val Val Ile Asp Val Glu Thr Ala Gly Phe Asn Ala Lys
            20                  25                  30

Thr Asp Ala Leu Leu Glu Ile Ala Ala Ile Thr Leu Lys Met Asp Glu
        35                  40                  45

Gln Gly Trp Leu Met Pro Asp Thr Thr Leu His Phe His Val Glu Pro
    50                  55                  60

Phe Val Gly Ala Asn Leu Gln Pro Glu Ala Leu Ala Phe Asn Gly Ile
65                  70                  75                  80

Asp Pro Asn Asp Pro Asp Arg Gly Ala Val Ser Glu Tyr Glu Ala Leu
                85                  90                  95

His Glu Ile Phe Lys Val Val Arg Lys Gly Ile Lys Ala Ser Gly Cys
            100                 105                 110

Asn Arg Ala Ile Met Val Ala His Asn Ala Asn Phe Asp His Ser Phe
        115                 120                 125

Met Met Ala Ala Ala Glu Arg Ala Ser Leu Lys Arg Asn Pro Phe His
    130                 135                 140

Pro Phe Ala Thr Phe Asp Thr Ala Ala Leu Ala Gly Leu Ala Leu Gly
145                 150                 155                 160

Gln Thr Val Leu Ser Lys Ala Cys Gln Thr Ala Gly Met Asp Phe Asp
                165                 170                 175

Ser Thr Gln Ala His Ser Ala Leu Tyr Asp Thr Glu Arg Thr Ala Val
            180                 185                 190

Leu Phe Cys Glu Ile Val Asn Arg Trp Lys Arg Leu Gly Gly Trp Pro
        195                 200                 205

Leu Ser Ala Ala Glu Glu Val
    210                 215
```

<210> SEQ ID NO 5
<211> LENGTH: 236
<212> TYPE: PRT
<213> ORGANISM: Artificial Sequence
<220> FEATURE:
<223> OTHER INFORMATION: TREX2

<400> SEQUENCE: 5

Met Ser Glu Ala Pro Arg Ala Glu Thr Phe Val Phe Leu Asp Leu Glu

```
                 1               5                  10                 15
             Ala Thr Gly Leu Pro Ser Val Glu Pro Glu Ile Ala Glu Leu Ser Leu
                             20                 25                 30

Phe Ala Val His Arg Ser Ser Leu Glu Asn Pro Glu His Asp Glu Ser
                             35                 40                 45

Gly Ala Leu Val Leu Pro Arg Val Leu Asp Lys Leu Thr Leu Cys Met
                             50                 55                 60

Cys Pro Glu Arg Pro Phe Thr Ala Lys Ala Ser Glu Ile Thr Gly Leu
             65                 70                 75                 80

Ser Ser Glu Gly Leu Ala Arg Cys Arg Lys Ala Gly Phe Asp Gly Ala
                             85                 90                 95

Val Val Arg Thr Leu Gln Ala Phe Leu Ser Arg Gln Ala Gly Pro Ile
                            100                105                110

Cys Leu Val Ala His Asn Gly Phe Asp Tyr Asp Phe Pro Leu Leu Cys
                            115                120                125

Ala Glu Leu Arg Arg Leu Gly Ala Arg Leu Pro Arg Asp Thr Val Cys
                            130                135                140

Leu Asp Thr Leu Pro Ala Leu Arg Gly Leu Asp Arg Ala His Ser His
             145                150                155                160

Gly Thr Arg Ala Arg Gly Arg Gln Gly Tyr Ser Leu Gly Ser Leu Phe
                            165                170                175

His Arg Tyr Phe Arg Ala Glu Pro Ser Ala Ala His Ser Ala Glu Gly
                            180                185                190

Asp Val His Thr Leu Leu Leu Ile Phe Leu His Arg Ala Ala Glu Leu
                            195                200                205

Leu Ala Trp Ala Asp Glu Gln Ala Arg Gly Trp Ala His Ile Glu Pro
                            210                215                220

Met Tyr Leu Pro Pro Asp Asp Pro Ser Leu Glu Ala
             225                230                235

<210> SEQ ID NO 6
<211> LENGTH: 304
<212> TYPE: PRT
<213> ORGANISM: Artificial Sequence
<220> FEATURE:
<223> OTHER INFORMATION: TREX1

<400> SEQUENCE: 6

Met Gln Thr Leu Ile Phe Phe Asp Met Glu Ala Thr Gly Leu Pro Phe
1               5                  10                 15

Ser Gln Pro Lys Val Thr Glu Leu Cys Leu Leu Ala Val His Arg Cys
                20                 25                 30

Ala Leu Glu Ser Pro Pro Thr Ser Gln Gly Pro Pro Pro Thr Val Pro
                35                 40                 45

Pro Pro Pro Arg Val Val Asp Lys Leu Ser Leu Cys Val Ala Pro Gly
                50                 55                 60

Lys Ala Cys Ser Pro Ala Ala Ser Glu Ile Thr Gly Leu Ser Thr Ala
65                  70                 75                 80

Val Leu Ala Ala His Gly Arg Gln Cys Phe Asp Asp Asn Leu Ala Asn
                85                 90                 95

Leu Leu Leu Ala Phe Leu Arg Arg Gln Pro Gln Pro Trp Cys Leu Val
                100                105                110

Ala His Asn Gly Asp Arg Tyr Asp Phe Pro Leu Leu Gln Ala Glu Leu
                115                120                125

Ala Met Leu Gly Leu Thr Ser Ala Leu Asp Gly Ala Phe Cys Val Asp
```

```
              130                 135                 140
Ser Ile Thr Ala Leu Lys Ala Leu Glu Arg Ala Ser Ser Pro Ser Glu
145                 150                 155                 160

His Gly Pro Arg Lys Ser Tyr Ser Leu Gly Ser Ile Tyr Thr Arg Leu
                165                 170                 175

Tyr Gly Gln Ser Pro Pro Asp Ser His Thr Ala Glu Gly Asp Val Leu
                180                 185                 190

Ala Leu Leu Ser Ile Cys Gln Trp Arg Pro Gln Ala Leu Leu Arg Trp
                195                 200                 205

Val Asp Ala His Ala Arg Pro Phe Gly Thr Ile Arg Pro Met Tyr Gly
            210                 215                 220

Val Thr Ala Ser Ala Arg Thr Lys Pro Arg Pro Ser Ala Val Thr Thr
225                 230                 235                 240

Thr Ala His Leu Ala Thr Thr Arg Asn Thr Ser Pro Ser Leu Arg Glu
                245                 250                 255

Ser Arg Gly Thr Lys Asp Leu Pro Pro Val Lys Asp Pro Gly Ala Leu
                260                 265                 270

Ser Arg Glu Gly Leu Leu Ala Pro Leu Gly Leu Leu Ala Ile Leu Thr
                275                 280                 285

Leu Ala Val Ala Thr Leu Tyr Gly Leu Ser Leu Ala Thr Pro Gly Asp
    290                 295                 300
```

<210> SEQ ID NO 7
<211> LENGTH: 1180
<212> TYPE: PRT
<213> ORGANISM: Artificial Sequence
<220> FEATURE:
<223> OTHER INFORMATION: RecBCD_RecB

<400> SEQUENCE: 7

```
Met Ser Asp Val Ala Glu Thr Leu Asp Pro Leu Arg Leu Pro Leu Gln
1               5                   10                  15

Gly Glu Arg Leu Ile Glu Ala Ser Ala Gly Thr Gly Lys Thr Phe Thr
                20                  25                  30

Ile Ala Ala Leu Tyr Leu Arg Leu Leu Gly Leu Gly Gly Ser Ala
            35                  40                  45

Ala Phe Pro Arg Pro Leu Thr Val Glu Glu Leu Leu Val Val Thr Phe
    50                  55                  60

Thr Glu Ala Ala Thr Ala Glu Leu Arg Gly Arg Ile Arg Ser Asn Ile
65                  70                  75                  80

His Glu Leu Arg Ile Ala Cys Leu Arg Glu Thr Thr Asp Asn Pro Leu
                85                  90                  95

Tyr Glu Arg Leu Leu Glu Glu Ile Asp Asp Lys Ala Gln Ala Ala Gln
                100                 105                 110

Trp Leu Leu Leu Ala Glu Arg Gln Met Asp Glu Ala Ala Val Phe Thr
            115                 120                 125

Ile His Gly Phe Cys Gln Arg Met Leu Asn Leu Asn Ala Phe Glu Ser
        130                 135                 140

Gly Met Leu Phe Glu Gln Gln Leu Ile Glu Asp Glu Ser Leu Leu Arg
145                 150                 155                 160

Tyr Gln Ala Cys Ala Asp Phe Trp Arg Arg His Cys Tyr Pro Leu Pro
                165                 170                 175

Arg Glu Ile Ala Gln Val Val Phe Glu Thr Trp Lys Gly Pro Gln Ala
                180                 185                 190

Leu Leu Arg Asp Ile Asn Arg Tyr Leu Gln Gly Glu Ala Pro Val Ile
```

```
            195                 200                 205
Lys Ala Pro Pro Asp Asp Glu Thr Leu Ala Ser Arg His Ala Gln
210                 215                 220

Ile Val Ala Arg Ile Asp Thr Val Lys Gln Gln Trp Arg Asp Ala Val
225                 230                 235                 240

Gly Glu Leu Asp Ala Leu Ile Glu Ser Ser Gly Ile Asp Arg Arg Lys
                245                 250                 255

Phe Asn Arg Ser Asn Gln Ala Lys Trp Ile Asp Lys Ile Ser Ala Trp
                260                 265                 270

Ala Glu Glu Glu Thr Asn Ser Tyr Gln Leu Pro Glu Ser Leu Glu Lys
                275                 280                 285

Phe Ser Gln Arg Phe Leu Glu Asp Arg Thr Lys Ala Gly Gly Glu Thr
290                 295                 300

Pro Arg His Pro Leu Phe Glu Ala Ile Asp Gln Leu Leu Ala Glu Pro
305                 310                 315                 320

Leu Ser Ile Arg Asp Leu Val Ile Thr Arg Ala Leu Ala Glu Ile Arg
                325                 330                 335

Glu Thr Val Ala Arg Glu Lys Arg Arg Gly Glu Leu Gly Phe Asp
                340                 345                 350

Asp Met Leu Ser Arg Leu Asp Ser Ala Leu Arg Ser Glu Ser Gly Glu
                355                 360                 365

Val Leu Ala Ala Ala Ile Arg Thr Arg Phe Pro Val Ala Met Ile Asp
370                 375                 380

Glu Phe Gln Asp Thr Asp Pro Gln Gln Tyr Arg Ile Phe Arg Arg Ile
385                 390                 395                 400

Trp His His Gln Pro Glu Thr Ala Leu Leu Leu Ile Gly Asp Pro Lys
                405                 410                 415

Gln Ala Ile Tyr Ala Phe Arg Gly Ala Asp Ile Phe Thr Tyr Met Lys
                420                 425                 430

Ala Arg Ser Glu Val His Ala His Tyr Thr Leu Asp Thr Asn Trp Arg
                435                 440                 445

Ser Ala Pro Gly Met Val Asn Ser Val Asn Lys Leu Phe Ser Gln Thr
450                 455                 460

Asp Asp Ala Phe Met Phe Arg Glu Ile Pro Phe Ile Pro Val Lys Ser
465                 470                 475                 480

Ala Gly Lys Asn Gln Ala Leu Arg Phe Val Phe Lys Gly Glu Thr Gln
                485                 490                 495

Pro Ala Met Lys Met Trp Leu Met Glu Gly Glu Ser Cys Gly Val Gly
                500                 505                 510

Asp Tyr Gln Ser Thr Met Ala Gln Val Cys Ala Ala Gln Ile Arg Asp
                515                 520                 525

Trp Leu Gln Ala Gly Gln Arg Gly Glu Ala Leu Leu Met Asn Gly Asp
530                 535                 540

Asp Ala Arg Pro Val Arg Ala Ser Asp Ile Ser Val Leu Val Arg Ser
545                 550                 555                 560

Arg Gln Glu Ala Ala Gln Val Arg Asp Ala Leu Thr Leu Leu Glu Ile
                565                 570                 575

Pro Ser Val Tyr Leu Ser Asn Arg Asp Ser Val Phe Glu Thr Leu Glu
                580                 585                 590

Ala Gln Glu Met Leu Trp Leu Leu Gln Ala Val Met Thr Pro Glu Arg
                595                 600                 605

Glu Asn Thr Leu Arg Ser Ala Leu Ala Thr Ser Met Met Gly Leu Asn
610                 615                 620
```

-continued

```
Ala Leu Asp Ile Glu Thr Leu Asn Asn Asp Glu His Ala Trp Asp Val
625                 630                 635                 640

Val Val Glu Glu Phe Asp Gly Tyr Arg Gln Ile Trp Arg Lys Arg Gly
            645                 650                 655

Val Met Pro Met Leu Arg Ala Leu Met Ser Ala Arg Asn Ile Ala Glu
            660                 665                 670

Asn Leu Leu Ala Thr Ala Gly Gly Glu Arg Arg Leu Thr Asp Ile Leu
            675                 680                 685

His Ile Ser Glu Leu Leu Gln Glu Ala Gly Thr Gln Leu Glu Ser Glu
            690                 695                 700

His Ala Leu Val Arg Trp Leu Ser Gln His Ile Leu Glu Pro Asp Ser
705                 710                 715                 720

Asn Ala Ser Ser Gln Gln Met Arg Leu Glu Ser Asp Lys His Leu Val
            725                 730                 735

Gln Ile Val Thr Ile His Lys Ser Lys Gly Leu Glu Tyr Pro Leu Val
            740                 745                 750

Trp Leu Pro Phe Ile Thr Asn Phe Arg Val Gln Glu Gln Ala Phe Tyr
            755                 760                 765

His Asp Arg His Ser Phe Glu Ala Val Leu Asp Leu Asn Ala Ala Pro
            770                 775                 780

Glu Ser Val Asp Leu Ala Glu Ala Glu Arg Leu Ala Glu Asp Leu Arg
785                 790                 795                 800

Leu Leu Tyr Val Ala Leu Thr Arg Ser Val Trp His Cys Ser Leu Gly
            805                 810                 815

Val Ala Pro Leu Val Arg Arg Gly Asp Lys Lys Gly Asp Thr Asp
            820                 825                 830

Val His Gln Ser Ala Leu Gly Arg Leu Leu Gln Lys Gly Glu Pro Gln
            835                 840                 845

Asp Ala Ala Gly Leu Arg Thr Cys Ile Glu Ala Leu Cys Asp Asp Asp
850                 855                 860

Ile Ala Trp Gln Thr Ala Gln Thr Gly Asp Asn Gln Pro Trp Gln Val
865                 870                 875                 880

Asn Asp Val Ser Thr Ala Glu Leu Asn Ala Lys Thr Leu Gln Arg Leu
            885                 890                 895

Pro Gly Asp Asn Trp Arg Val Thr Ser Tyr Ser Gly Leu Gln Gln Arg
            900                 905                 910

Gly His Gly Ile Ala Gln Asp Leu Met Pro Arg Leu Asp Val Asp Ala
            915                 920                 925

Ala Gly Val Ala Ser Val Val Glu Glu Pro Thr Leu Thr Pro His Gln
            930                 935                 940

Phe Pro Arg Gly Ala Ser Pro Gly Thr Phe Leu His Ser Leu Phe Glu
945                 950                 955                 960

Asp Leu Asp Phe Thr Gln Pro Val Asp Pro Asn Trp Val Arg Glu Lys
            965                 970                 975

Leu Glu Leu Gly Gly Phe Glu Ser Gln Trp Glu Pro Val Leu Thr Glu
            980                 985                 990

Trp Ile Thr Ala Val Leu Gln Ala Pro Leu Asn Glu Thr Gly Val Ser
            995                 1000                1005

Leu Ser Gln Leu Ser Ala Arg Asn Lys Gln Val Glu Met Glu Phe Tyr
            1010                1015                1020

Leu Pro Ile Ser Glu Pro Leu Ile Ala Ser Gln Leu Asp Thr Leu Ile
1025                1030                1035                1040
```

```
Arg Gln Phe Asp Pro Leu Ser Ala Gly Cys Pro Pro Leu Glu Phe Met
                1045                1050                1055

Gln Val Arg Gly Met Leu Lys Gly Phe Ile Asp Leu Val Phe Arg His
            1060                1065                1070

Glu Gly Arg Tyr Tyr Leu Leu Asp Tyr Lys Ser Asn Trp Leu Gly Glu
        1075                1080                1085

Asp Ser Ser Ala Tyr Thr Gln Gln Ala Met Ala Ala Met Gln Ala
    1090                1095                1100

His Arg Tyr Asp Leu Gln Tyr Gln Leu Tyr Thr Leu Ala Leu His Arg
1105                1110                1115                1120

Tyr Leu Arg His Arg Ile Ala Asp Tyr Asp Tyr Glu His His Phe Gly
                1125                1130                1135

Gly Val Ile Tyr Leu Phe Leu Arg Gly Val Asp Lys Glu His Pro Gln
            1140                1145                1150

Gln Gly Ile Tyr Thr Thr Arg Pro Asn Ala Gly Leu Ile Ala Leu Met
        1155                1160                1165

Asp Glu Met Phe Ala Gly Met Thr Leu Glu Glu Ala
    1170                1175                1180

<210> SEQ ID NO 8
<211> LENGTH: 1122
<212> TYPE: PRT
<213> ORGANISM: Artificial Sequence
<220> FEATURE:
<223> OTHER INFORMATION: RecBCD_RecC

<400> SEQUENCE: 8

Met Leu Arg Val Tyr His Ser Asn Arg Leu Asp Val Leu Glu Ala Leu
1               5                   10                  15

Met Glu Phe Ile Val Glu Arg Glu Arg Leu Asp Asp Pro Phe Glu Pro
            20                  25                  30

Glu Met Ile Leu Val Gln Ser Thr Gly Met Ala Gln Trp Leu Gln Met
        35                  40                  45

Thr Leu Ser Gln Lys Phe Gly Ile Ala Ala Asn Ile Asp Phe Pro Leu
    50                  55                  60

Pro Ala Ser Phe Ile Trp Asp Met Phe Val Arg Val Leu Pro Glu Ile
65                  70                  75                  80

Pro Lys Glu Ser Ala Phe Asn Lys Gln Ser Met Ser Trp Lys Leu Met
                85                  90                  95

Thr Leu Leu Pro Gln Leu Leu Glu Arg Glu Asp Phe Thr Leu Leu Arg
            100                 105                 110

His Tyr Leu Thr Asp Asp Ser Asp Lys Arg Lys Leu Phe Gln Leu Ser
        115                 120                 125

Ser Lys Ala Ala Asp Leu Phe Asp Gln Tyr Leu Val Tyr Arg Pro Asp
    130                 135                 140

Trp Leu Ala Gln Trp Glu Thr Gly His Leu Val Glu Gly Leu Gly Glu
145                 150                 155                 160

Ala Gln Ala Trp Gln Ala Pro Leu Trp Lys Ala Leu Val Glu Tyr Thr
                165                 170                 175

His Gln Leu Gly Gln Pro Arg Trp His Arg Ala Asn Leu Tyr Gln Arg
            180                 185                 190

Phe Ile Glu Thr Leu Glu Ser Ala Thr Thr Cys Pro Pro Gly Leu Pro
        195                 200                 205

Ser Arg Val Phe Ile Cys Gly Ile Ser Ala Leu Pro Pro Val Tyr Leu
    210                 215                 220
```

```
Gln Ala Leu Gln Ala Leu Gly Lys His Ile Glu Ile His Leu Leu Phe
225                 230                 235                 240
Thr Asn Pro Cys Arg Tyr Tyr Trp Gly Asp Ile Lys Asp Pro Ala Tyr
            245                 250                 255
Leu Ala Lys Leu Leu Thr Arg Gln Arg Arg His Ser Phe Glu Asp Arg
        260                 265                 270
Glu Leu Pro Leu Phe Arg Asp Ser Glu Asn Ala Gly Gln Leu Phe Asn
    275                 280                 285
Ser Asp Gly Glu Gln Asp Val Gly Asn Pro Leu Leu Ala Ser Trp Gly
290                 295                 300
Lys Leu Gly Arg Asp Tyr Ile Tyr Leu Leu Ser Asp Leu Glu Ser Ser
305                 310                 315                 320
Gln Glu Leu Asp Ala Phe Val Asp Val Thr Pro Asp Asn Leu Leu His
                325                 330                 335
Asn Ile Gln Ser Asp Ile Leu Glu Leu Glu Asn Arg Ala Val Ala Gly
            340                 345                 350
Val Asn Ile Glu Glu Phe Ser Arg Ser Asp Asn Lys Arg Pro Leu Asp
        355                 360                 365
Pro Leu Asp Ser Ser Ile Thr Phe His Val Cys His Ser Pro Gln Arg
    370                 375                 380
Glu Val Glu Val Leu His Asp Arg Leu Leu Ala Met Leu Glu Glu Asp
385                 390                 395                 400
Pro Thr Leu Thr Pro Arg Asp Ile Ile Val Met Val Ala Asp Ile Asp
                405                 410                 415
Ser Tyr Ser Pro Phe Ile Gln Ala Val Phe Gly Ser Ala Pro Ala Asp
            420                 425                 430
Arg Tyr Leu Pro Tyr Ala Ile Ser Asp Arg Arg Ala Arg Gln Ser His
        435                 440                 445
Pro Val Leu Glu Ala Phe Ile Ser Leu Leu Ser Leu Pro Asp Ser Arg
    450                 455                 460
Phe Val Ser Glu Asp Val Leu Ala Leu Leu Asp Val Pro Val Leu Ala
465                 470                 475                 480
Ala Arg Phe Asp Ile Thr Glu Glu Gly Leu Arg Tyr Leu Arg Gln Trp
                485                 490                 495
Val Asn Glu Ser Gly Ile Arg Trp Gly Ile Asp Asp Asp Asn Val Arg
            500                 505                 510
Glu Leu Glu Leu Pro Ala Thr Gly Gln His Thr Trp Arg Phe Gly Leu
        515                 520                 525
Thr Arg Met Leu Leu Gly Tyr Ala Met Glu Ser Ala Gln Gly Glu Trp
    530                 535                 540
Gln Ser Val Leu Pro Tyr Asp Glu Ser Ser Gly Leu Ile Ala Glu Leu
545                 550                 555                 560
Val Gly His Leu Ala Ser Leu Leu Met Gln Leu Asn Ile Trp Arg Arg
                565                 570                 575
Gly Leu Ala Gln Glu Arg Pro Leu Glu Glu Trp Leu Pro Val Cys Arg
            580                 585                 590
Asp Met Leu Asn Ala Phe Phe Leu Pro Asp Ala Glu Thr Glu Ala Ala
        595                 600                 605
Met Thr Leu Ile Glu Gln Gln Trp Gln Ala Ile Ile Ala Glu Gly Leu
    610                 615                 620
Gly Ala Gln Tyr Gly Asp Ala Val Pro Leu Ser Leu Leu Arg Asp Glu
625                 630                 635                 640
Leu Ala Gln Arg Leu Asp Gln Glu Arg Ile Ser Gln Arg Phe Leu Ala
```

-continued

```
                645                 650                 655
Gly Pro Val Asn Ile Cys Thr Leu Met Pro Met Arg Ser Ile Pro Phe
            660                 665                 670

Lys Val Val Cys Leu Leu Gly Met Asn Asp Gly Val Tyr Pro Arg Gln
            675                 680                 685

Leu Ala Pro Leu Gly Phe Asp Leu Met Ser Gln Lys Pro Lys Arg Gly
            690                 695                 700

Asp Arg Ser Arg Arg Asp Asp Arg Tyr Leu Phe Leu Glu Ala Leu
705                 710                 715                 720

Ile Ser Ala Gln Gln Lys Leu Tyr Ile Ser Tyr Ile Gly Arg Ser Ile
                725                 730                 735

Gln Asp Asn Ser Glu Arg Phe Pro Ser Val Leu Val Gln Glu Leu Ile
            740                 745                 750

Asp Tyr Ile Gly Gln Ser His Tyr Leu Pro Gly Asp Glu Ala Leu Asn
            755                 760                 765

Cys Asp Glu Ser Glu Ala Arg Val Lys Ala His Leu Thr Cys Leu His
            770                 775                 780

Thr Arg Met Pro Phe Asp Pro Gln Asn Tyr Gln Pro Gly Glu Arg Gln
785                 790                 795                 800

Ser Tyr Ala Arg Glu Trp Leu Pro Ala Ala Ser Gln Ala Gly Lys Ala
                805                 810                 815

His Ser Glu Phe Val Gln Pro Leu Pro Phe Thr Leu Pro Glu Thr Val
            820                 825                 830

Pro Leu Glu Thr Leu Gln Arg Phe Trp Ala His Pro Val Arg Ala Phe
            835                 840                 845

Phe Gln Met Arg Leu Gln Val Asn Phe Arg Thr Glu Asp Ser Glu Ile
850                 855                 860

Pro Asp Thr Glu Pro Phe Ile Leu Glu Gly Leu Ser Arg Tyr Gln Ile
865                 870                 875                 880

Asn Gln Gln Leu Leu Asn Ala Leu Val Glu Gln Asp Asp Ala Glu Arg
                885                 890                 895

Leu Phe Arg Arg Phe Arg Ala Ala Gly Asp Leu Pro Tyr Gly Ala Phe
            900                 905                 910

Gly Glu Ile Phe Trp Glu Thr Gln Cys Gln Glu Met Gln Gln Leu Ala
            915                 920                 925

Asp Arg Val Ile Ala Cys Arg Gln Pro Gly Gln Ser Met Glu Ile Asp
            930                 935                 940

Leu Ala Cys Asn Gly Val Gln Ile Thr Gly Trp Leu Pro Gln Val Gln
945                 950                 955                 960

Pro Asp Gly Leu Leu Arg Trp Arg Pro Ser Leu Leu Ser Val Ala Gln
            965                 970                 975

Gly Met Gln Leu Trp Leu Glu His Leu Val Tyr Cys Ala Ser Gly Gly
            980                 985                 990

Asn Gly Glu Ser Arg Leu Phe Leu Arg Lys Asp Gly Glu Trp Arg Phe
            995                 1000                1005

Pro Pro Leu Ala Ala Glu Gln Ala Leu His Tyr Leu Ser Gln Leu Ile
            1010                1015                1020

Glu Gly Tyr Arg Glu Gly Met Ser Ala Pro Leu Leu Val Leu Pro Glu
1025                1030                1035                1040

Ser Gly Gly Ala Trp Leu Lys Thr Cys Tyr Asp Ala Gln Asn Asp Ala
                1045                1050                1055

Met Leu Asp Asp Asp Ser Thr Leu Gln Lys Ala Arg Thr Lys Phe Leu
            1060                1065                1070
```

-continued

Gln Ala Tyr Glu Gly Asn Met Met Val Arg Gly Glu Gly Asp Asp Ile
       1075                1080                1085

Trp Tyr Gln Arg Leu Trp Arg Gln Leu Thr Pro Glu Thr Met Glu Ala
       1090                1095                1100

Ile Val Glu Gln Ser Gln Arg Phe Leu Pro Leu Phe Arg Phe Asn
1105                1110                1115                1120

Gln Ser

<210> SEQ ID NO 9
<211> LENGTH: 608
<212> TYPE: PRT
<213> ORGANISM: Artificial Sequence
<220> FEATURE:
<223> OTHER INFORMATION: RecBCD_RecD

<400> SEQUENCE: 9

Met Lys Leu Gln Lys Gln Leu Leu Glu Ala Val Glu His Lys Gln Leu
1               5                   10                  15

Arg Pro Leu Asp Val Gln Phe Ala Leu Thr Val Ala Gly Asp Glu His
                20                  25                  30

Pro Ala Val Thr Leu Ala Ala Ala Leu Leu Ser His Asp Ala Gly Glu
            35                  40                  45

Gly His Val Cys Leu Pro Leu Ser Arg Leu Glu Asn Asn Glu Ala Ser
        50                  55                  60

His Pro Leu Leu Ala Thr Cys Val Ser Glu Ile Gly Glu Leu Gln Asn
65                  70                  75                  80

Trp Glu Glu Cys Leu Ala Ser Gln Ala Val Ser Arg Gly Asp Glu
                85                  90                  95

Pro Thr Pro Met Ile Leu Cys Gly Asp Arg Leu Tyr Leu Asn Arg Met
                100                 105                 110

Trp Cys Asn Glu Arg Thr Val Ala Arg Phe Phe Asn Glu Val Asn His
            115                 120                 125

Ala Ile Glu Val Asp Glu Ala Leu Leu Ala Gln Thr Leu Asp Lys Leu
        130                 135                 140

Phe Pro Val Ser Asp Glu Ile Asn Trp Gln Lys Val Ala Ala Ala Val
145                 150                 155                 160

Ala Leu Thr Arg Arg Ile Ser Val Ile Ser Gly Gly Pro Gly Thr Gly
                165                 170                 175

Lys Thr Thr Thr Val Ala Lys Leu Leu Ala Ala Leu Ile Gln Met Ala
                180                 185                 190

Asp Gly Glu Arg Cys Arg Ile Arg Leu Ala Ala Pro Thr Gly Lys Ala
            195                 200                 205

Ala Ala Arg Leu Thr Glu Ser Leu Gly Lys Ala Leu Arg Gln Leu Pro
        210                 215                 220

Leu Thr Asp Glu Gln Lys Lys Arg Ile Pro Glu Asp Ala Ser Thr Leu
225                 230                 235                 240

His Arg Leu Leu Gly Ala Gln Pro Gly Ser Gln Arg Leu Arg His His
                245                 250                 255

Ala Gly Asn Pro Leu His Leu Asp Val Leu Val Val Asp Glu Ala Ser
            260                 265                 270

Met Ile Asp Leu Pro Met Met Ser Arg Leu Ile Asp Ala Leu Pro Asp
        275                 280                 285

His Ala Arg Val Ile Phe Leu Gly Asp Arg Asp Gln Leu Ala Ser Val
    290                 295                 300

```
Glu Ala Gly Ala Val Leu Gly Asp Ile Cys Ala Tyr Ala Asn Ala Gly
305                 310                 315                 320

Phe Thr Ala Glu Arg Ala Arg Gln Leu Ser Arg Leu Thr Gly Thr His
            325                 330                 335

Val Pro Ala Gly Thr Gly Thr Glu Ala Ala Ser Leu Arg Asp Ser Leu
            340                 345                 350

Cys Leu Leu Gln Lys Ser Tyr Arg Phe Gly Ser Asp Ser Gly Ile Gly
            355                 360                 365

Gln Leu Ala Ala Ala Ile Asn Arg Gly Asp Lys Thr Ala Val Lys Thr
            370                 375                 380

Val Phe Gln Gln Asp Phe Thr Asp Ile Glu Lys Arg Leu Leu Gln Ser
385                 390                 395                 400

Gly Glu Asp Tyr Ile Ala Met Leu Glu Glu Ala Leu Ala Gly Tyr Gly
                405                 410                 415

Arg Tyr Leu Asp Leu Leu Gln Ala Arg Ala Glu Pro Asp Leu Ile Ile
            420                 425                 430

Gln Ala Phe Asn Glu Tyr Gln Leu Leu Cys Ala Leu Arg Glu Gly Pro
            435                 440                 445

Phe Gly Val Ala Gly Leu Asn Glu Arg Ile Glu Gln Phe Met Gln Gln
450                 455                 460

Lys Arg Lys Ile His Arg His Pro His Ser Arg Trp Tyr Glu Gly Arg
465                 470                 475                 480

Pro Val Met Ile Ala Arg Asn Asp Ser Ala Leu Gly Leu Phe Asn Gly
                485                 490                 495

Asp Ile Gly Ile Ala Leu Asp Arg Gly Gln Gly Thr Arg Val Trp Phe
                500                 505                 510

Ala Met Pro Asp Gly Asn Ile Lys Ser Val Gln Pro Ser Arg Leu Pro
            515                 520                 525

Glu His Glu Thr Thr Trp Ala Met Thr Val His Lys Ser Gln Gly Ser
530                 535                 540

Glu Phe Asp His Ala Ala Leu Ile Leu Pro Ser Gln Arg Thr Pro Val
545                 550                 555                 560

Val Thr Arg Glu Leu Val Tyr Thr Ala Val Thr Arg Ala Arg Arg Arg
                565                 570                 575

Leu Ser Leu Tyr Ala Asp Glu Arg Ile Leu Ser Ala Ala Ile Ala Thr
            580                 585                 590

Arg Thr Glu Arg Arg Ser Gly Leu Ala Ala Leu Phe Ser Ser Arg Glu
            595                 600                 605

<210> SEQ ID NO 10
<211> LENGTH: 475
<212> TYPE: PRT
<213> ORGANISM: Artificial Sequence
<220> FEATURE:
<223> OTHER INFORMATION: Exodeoxyribonuclease I

<400> SEQUENCE: 10

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60
```

```
Leu Ile Thr Gly Ile Thr Pro Gln Glu Ala Arg Ala Lys Gly Glu Asn
 65                  70                  75                  80

Glu Ala Ala Phe Ala Ala Arg Ile His Ser Leu Phe Thr Val Pro Lys
                 85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val
465                 470                 475
```

<210> SEQ ID NO 11
<211> LENGTH: 268
<212> TYPE: PRT
<213> ORGANISM: Artificial Sequence
<220> FEATURE:
<223> OTHER INFORMATION: Exodeoxyribonuclease III

<400> SEQUENCE: 11

```
Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265
```

<210> SEQ ID NO 12
<211> LENGTH: 355
<212> TYPE: PRT
<213> ORGANISM: Artificial Sequence
<220> FEATURE:
<223> OTHER INFORMATION: Mungbean exonuclease

<400> SEQUENCE: 12

```
Met Gln Thr Leu Gln Met Ser Leu Leu Thr Gln Pro Tyr Val Gln Pro
1               5                   10                  15

Arg Phe Pro Cys Lys Arg Tyr Pro Thr Phe Ser Ala Ser Cys Arg Thr
            20                  25                  30

Gln Lys Thr Ala Ile Thr Lys Thr Glu Lys Val Phe Ser Glu Ser
        35                  40                  45
```

-continued

Phe Asp Gln Thr Arg Cys Thr Gln Pro Leu Ser Glu Lys Lys Lys Arg
 50                  55                  60

Val Phe Phe Leu Asp Val Asn Pro Leu Cys Tyr Glu Gly Ser Lys Pro
 65                      70                  75                  80

Ser Leu Arg Ser Phe Gly Arg Trp Leu Ser Leu Phe Leu His Gln Val
                 85                  90                  95

Ser Leu Thr Asp Pro Val Ile Ala Val Ile Asp Gly Glu Gly Gly Ser
            100                 105                 110

Glu His Arg Arg Lys Leu Leu Pro Ser Tyr Lys Ala His Arg Lys Lys
        115                 120                 125

Phe Met Arg His Met Ser Ser Gly His Val Gly Arg Ser His Gln Val
130                 135                 140

Ile Asn Asp Val Leu Gly Lys Cys Asn Val Pro Val Ile Lys Val Ala
145                 150                 155                 160

Gly His Glu Ala Asp Asp Val Val Ala Thr Leu Ala Gly Gln Val Val
                165                 170                 175

Asn Lys Gly Phe Arg Val Val Ile Gly Ser Pro Asp Lys Asp Phe Lys
            180                 185                 190

Gln Leu Ile Ser Glu Asp Val Gln Ile Val Met Pro Leu Pro Glu Leu
        195                 200                 205

Gln Arg Trp Ser Phe Tyr Thr Leu Arg His Tyr Arg Asp Gln Tyr Asn
210                 215                 220

Cys Asp Pro Glu Ser Asp Leu Ser Phe Arg Cys Ile Val Gly Asp Glu
225                 230                 235                 240

Val Asp Gly Val Pro Gly Ile Gln His Leu Val Pro Ser Phe Gly Arg
                245                 250                 255

Lys Thr Ala Met Lys Leu Ile Lys Lys His Gly Ser Leu Glu Thr Leu
            260                 265                 270

Leu Asn Ala Ala Ala Ile Arg Thr Val Gly Arg Pro Tyr Ala Gln Asp
        275                 280                 285

Ala Leu Lys Asn His Ala Asp Tyr Leu Arg Arg Asn Tyr Glu Val Leu
290                 295                 300

Ala Leu Lys Arg Asp Val Asn Ile Gln Leu Tyr Asp Glu Trp Leu Val
305                 310                 315                 320

Lys Arg Asp Asn His Asn Asp Lys Thr Ala Leu Ser Ser Phe Phe Lys
                325                 330                 335

Tyr Leu Gly Glu Ser Lys Glu Leu Ser Tyr Asn Gly Arg Pro Ile Ser
            340                 345                 350

Tyr Asn Gly
        355

<210> SEQ ID NO 13
<211> LENGTH: 577
<212> TYPE: PRT
<213> ORGANISM: Artificial Sequence
<220> FEATURE:
<223> OTHER INFORMATION: RecJ

<400> SEQUENCE: 13

Val Lys Gln Gln Ile Gln Leu Arg Arg Arg Glu Val Asp Glu Thr Ala
 1                   5                  10                  15

Asp Leu Pro Ala Glu Leu Pro Pro Leu Arg Arg Leu Tyr Ala Ser
                 20                  25                  30

Arg Gly Val Arg Ser Ala Gln Glu Leu Glu Arg Ser Val Lys Gly Met
             35                  40                  45

-continued

```
Leu Pro Trp Gln Gln Leu Ser Gly Val Glu Lys Ala Val Glu Ile Leu
     50                  55                  60

Tyr Asn Ala Phe Arg Glu Gly Thr Arg Ile Ile Val Val Gly Asp Phe
 65                  70                  75                  80

Asp Ala Asp Gly Ala Thr Ser Thr Ala Leu Ser Val Leu Ala Met Arg
                 85                  90                  95

Ser Leu Gly Cys Ser Asn Ile Asp Tyr Leu Val Pro Asn Arg Phe Glu
                100                 105                 110

Asp Gly Tyr Gly Leu Ser Pro Glu Val Val Asp Gln Ala His Ala Arg
                115                 120                 125

Gly Ala Gln Leu Ile Val Thr Val Asp Asn Gly Ile Ser Ser His Ala
    130                 135                 140

Gly Val Glu His Ala Arg Ser Leu Gly Ile Pro Val Ile Val Thr Asp
145                 150                 155                 160

His His Leu Pro Gly Asp Thr Leu Pro Ala Ala Glu Ala Ile Ile Asn
                165                 170                 175

Pro Asn Leu Arg Asp Cys Asn Phe Pro Ser Lys Ser Leu Ala Gly Val
                180                 185                 190

Gly Val Ala Phe Tyr Leu Met Leu Ala Leu Arg Thr Phe Leu Arg Asp
    195                 200                 205

Gln Gly Trp Phe Asp Glu Arg Asn Ile Ala Ile Pro Asn Leu Ala Glu
    210                 215                 220

Leu Leu Asp Leu Val Ala Leu Gly Thr Val Ala Asp Val Val Pro Leu
225                 230                 235                 240

Asp Ala Asn Asn Arg Ile Leu Thr Trp Gln Gly Met Ser Arg Ile Arg
                245                 250                 255

Ala Gly Lys Cys Arg Pro Gly Ile Lys Ala Leu Leu Glu Val Ala Asn
                260                 265                 270

Arg Asp Ala Gln Lys Leu Ala Ala Ser Asp Leu Gly Phe Ala Leu Gly
        275                 280                 285

Pro Arg Leu Asn Ala Ala Gly Arg Leu Asp Asp Met Ser Val Gly Val
    290                 295                 300

Ala Leu Leu Leu Cys Asp Asn Ile Gly Glu Ala Arg Val Leu Ala Asn
305                 310                 315                 320

Glu Leu Asp Ala Leu Asn Gln Thr Arg Lys Glu Ile Glu Gln Gly Met
                325                 330                 335

Gln Ile Glu Ala Leu Thr Leu Cys Glu Lys Leu Glu Arg Ser Arg Asp
                340                 345                 350

Thr Leu Pro Gly Gly Leu Ala Met Tyr His Pro Glu Trp His Gln Gly
        355                 360                 365

Val Val Gly Ile Leu Ala Ser Arg Ile Lys Glu Arg Phe His Arg Pro
    370                 375                 380

Val Ile Ala Phe Ala Pro Ala Gly Asp Gly Thr Leu Lys Gly Ser Gly
385                 390                 395                 400

Arg Ser Ile Gln Gly Leu His Met Arg Asp Ala Leu Glu Arg Leu Asp
                405                 410                 415

Thr Leu Tyr Pro Gly Met Met Leu Lys Phe Gly Gly His Ala Met Ala
                420                 425                 430

Ala Gly Leu Ser Leu Glu Glu Asp Lys Phe Lys Leu Phe Gln Gln Arg
        435                 440                 445

Phe Gly Glu Leu Val Thr Glu Trp Leu Asp Pro Ser Leu Leu Gln Gly
    450                 455                 460

Glu Val Val Ser Asp Gly Pro Leu Ser Pro Ala Glu Met Thr Met Glu
```

```
                465                 470                 475                 480
Val Ala Gln Leu Leu Arg Asp Ala Gly Pro Trp Gly Gln Met Phe Pro
                    485                 490                 495

Glu Pro Leu Phe Asp Gly His Phe Arg Leu Leu Gln Gln Arg Leu Val
                500                 505                 510

Gly Glu Arg His Leu Lys Val Met Val Glu Pro Val Gly Gly Pro
            515                 520                 525

Leu Leu Asp Gly Ile Ala Phe Asn Val Asp Thr Ala Leu Trp Pro Asp
        530                 535                 540

Asn Gly Val Arg Glu Val Gln Leu Ala Tyr Lys Leu Asp Ile Asn Glu
545                 550                 555                 560

Phe Arg Gly Asn Arg Ser Leu Gln Ile Ile Asp Asn Ile Trp Pro
                565                 570                 575

Ile
```

<210> SEQ ID NO 14
<211> LENGTH: 866
<212> TYPE: PRT
<213> ORGANISM: Artificial Sequence
<220> FEATURE:
<223> OTHER INFORMATION: RecE

<400> SEQUENCE: 14

```
Met Ser Thr Lys Pro Leu Phe Leu Leu Arg Lys Ala Lys Lys Ser Ser
1               5                   10                  15

Gly Glu Pro Asp Val Val Leu Trp Ala Ser Asn Asp Phe Glu Ser Thr
                20                  25                  30

Cys Ala Thr Leu Asp Tyr Leu Ile Val Lys Ser Gly Lys Lys Leu Ser
            35                  40                  45

Ser Tyr Phe Lys Ala Val Ala Thr Asn Phe Pro Val Val Asn Asp Leu
        50                  55                  60

Pro Ala Glu Gly Glu Ile Asp Phe Thr Trp Ser Glu Arg Tyr Gln Leu
65                  70                  75                  80

Ser Lys Asp Ser Met Thr Trp Glu Leu Lys Pro Gly Ala Ala Pro Asp
                85                  90                  95

Asn Ala His Tyr Gln Gly Asn Thr Asn Val Asn Gly Glu Asp Met Thr
            100                 105                 110

Glu Ile Glu Glu Asn Met Leu Leu Pro Ile Ser Gly Gln Glu Leu Pro
        115                 120                 125

Ile Arg Trp Leu Ala Gln His Gly Ser Glu Lys Pro Val Thr His Val
    130                 135                 140

Ser Arg Asp Gly Leu Gln Ala Leu His Ile Ala Arg Ala Glu Glu Leu
145                 150                 155                 160

Pro Ala Val Thr Ala Leu Ala Val Ser His Lys Thr Ser Leu Leu Asp
                165                 170                 175

Pro Leu Glu Ile Arg Glu Leu His Lys Leu Val Arg Asp Thr Asp Lys
            180                 185                 190

Val Phe Pro Asn Pro Gly Asn Ser Asn Leu Gly Leu Ile Thr Ala Phe
        195                 200                 205

Phe Glu Ala Tyr Leu Asn Ala Asp Tyr Thr Asp Arg Gly Leu Leu Thr
    210                 215                 220

Lys Glu Trp Met Lys Gly Asn Arg Val Ser His Ile Thr Arg Thr Ala
225                 230                 235                 240

Ser Gly Ala Asn Ala Gly Gly Gly Asn Leu Thr Asp Arg Gly Glu Gly
                245                 250                 255
```

```
Phe Val His Asp Leu Thr Ser Leu Ala Arg Asp Val Ala Thr Gly Val
            260                 265                 270

Leu Ala Arg Ser Met Asp Leu Asp Ile Tyr Asn Leu His Pro Ala His
        275                 280                 285

Ala Lys Arg Ile Glu Glu Ile Ala Glu Asn Lys Pro Pro Phe Ser
290                 295                 300

Val Phe Arg Asp Lys Phe Ile Thr Met Pro Gly Gly Leu Asp Tyr Ser
305                 310                 315                 320

Arg Ala Ile Val Val Ala Ser Val Lys Glu Ala Pro Ile Gly Ile Glu
                325                 330                 335

Val Ile Pro Ala His Val Thr Glu Tyr Leu Asn Lys Val Leu Thr Glu
            340                 345                 350

Thr Asp His Ala Asn Pro Asp Pro Glu Ile Val Asp Ile Ala Cys Gly
        355                 360                 365

Arg Ser Ser Ala Pro Met Pro Gln Arg Val Thr Glu Glu Gly Lys Gln
370                 375                 380

Asp Asp Glu Glu Lys Pro Gln Pro Ser Gly Thr Thr Ala Val Glu Gln
385                 390                 395                 400

Gly Glu Ala Glu Thr Met Glu Pro Asp Ala Thr Glu His His Gln Asp
                405                 410                 415

Thr Gln Pro Leu Asp Ala Gln Ser Gln Val Asn Ser Val Asp Ala Lys
        420                 425                 430

Tyr Gln Glu Leu Arg Ala Glu Leu His Glu Ala Arg Lys Asn Ile Pro
        435                 440                 445

Ser Lys Asn Pro Val Asp Asp Lys Leu Leu Ala Ala Ser Arg Gly
450                 455                 460

Glu Phe Val Asp Gly Ile Ser Asp Pro Asn Asp Pro Lys Trp Val Lys
465                 470                 475                 480

Gly Ile Gln Thr Arg Asp Cys Val Tyr Gln Asn Gln Pro Glu Thr Glu
                485                 490                 495

Lys Thr Ser Pro Asp Met Asn Gln Pro Glu Pro Val Val Gln Gln Glu
        500                 505                 510

Pro Glu Ile Ala Cys Asn Ala Cys Gly Gln Thr Gly Gly Asp Asn Cys
        515                 520                 525

Pro Asp Cys Gly Ala Val Met Gly Asp Ala Thr Tyr Gln Glu Thr Phe
530                 535                 540

Asp Glu Glu Ser Gln Val Glu Ala Lys Glu Asn Asp Pro Glu Glu Met
545                 550                 555                 560

Glu Gly Ala Glu His Pro His Asn Glu Asn Ala Gly Ser Asp Pro His
                565                 570                 575

Arg Asp Cys Ser Asp Glu Thr Gly Glu Val Ala Asp Pro Val Ile Val
        580                 585                 590

Glu Asp Ile Glu Pro Gly Ile Tyr Tyr Gly Ile Ser Asn Glu Asn Tyr
        595                 600                 605

His Ala Gly Pro Gly Ile Ser Lys Ser Gln Leu Asp Asp Ile Ala Asp
        610                 615                 620

Thr Pro Ala Leu Tyr Leu Trp Arg Lys Asn Ala Pro Val Asp Thr Thr
625                 630                 635                 640

Lys Thr Lys Thr Leu Asp Leu Gly Thr Ala Phe His Cys Arg Val Leu
                645                 650                 655

Glu Pro Glu Glu Phe Ser Asn Arg Phe Ile Val Ala Pro Glu Phe Asn
        660                 665                 670
```

```
Arg Arg Thr Asn Ala Gly Lys Glu Glu Lys Ala Phe Leu Met Glu
        675                 680                 685

Cys Ala Ser Thr Gly Lys Thr Val Ile Thr Ala Glu Glu Gly Arg Lys
690                 695                 700

Ile Glu Leu Met Tyr Gln Ser Val Met Ala Leu Pro Leu Gly Gln Trp
705                 710                 715                 720

Leu Val Glu Ser Ala Gly His Ala Glu Ser Ser Ile Tyr Trp Glu Asp
                725                 730                 735

Pro Glu Thr Gly Ile Leu Cys Arg Cys Arg Pro Asp Lys Ile Ile Pro
            740                 745                 750

Glu Phe His Trp Ile Met Asp Val Lys Thr Thr Ala Asp Ile Gln Arg
        755                 760                 765

Phe Lys Thr Ala Tyr Tyr Asp Tyr Arg Tyr His Val Gln Asp Ala Phe
    770                 775                 780

Tyr Ser Asp Gly Tyr Glu Ala Gln Phe Gly Val Gln Pro Thr Phe Val
785                 790                 795                 800

Phe Leu Val Ala Ser Thr Thr Ile Glu Cys Gly Arg Tyr Pro Val Glu
                805                 810                 815

Ile Phe Met Met Gly Glu Glu Ala Lys Leu Ala Gly Gln Gln Glu Tyr
            820                 825                 830

His Arg Asn Leu Arg Thr Leu Ser Asp Cys Leu Asn Thr Asp Glu Trp
        835                 840                 845

Pro Ala Ile Lys Thr Leu Ser Leu Pro Arg Trp Ala Lys Glu Tyr Ala
    850                 855                 860

Asn Asp
865

<210> SEQ ID NO 15
<211> LENGTH: 276
<212> TYPE: PRT
<213> ORGANISM: Artificial Sequence
<220> FEATURE:
<223> OTHER INFORMATION: T5

<400> SEQUENCE: 15

Met Ala Ser Arg Arg Asn Leu Met Ile Val Asp Gly Thr Asn Leu Gly
1               5                   10                  15

Phe Arg Phe Lys His Asn Asn Ser Lys Lys Pro Phe Ala Ser Ser Tyr
            20                  25                  30

Val Ser Thr Ile Gln Ser Leu Ala Lys Ser Tyr Ser Ala Arg Thr Thr
        35                  40                  45

Ile Val Leu Gly Asp Lys Gly Lys Ser Val Phe Arg Leu Glu His Leu
    50                  55                  60

Pro Glu Tyr Lys Gly Asn Arg Asp Glu Lys Tyr Ala Gln Arg Thr Glu
65                  70                  75                  80

Glu Glu Lys Ala Leu Asp Glu Gln Phe Phe Glu Tyr Leu Lys Asp Ala
                85                  90                  95

Phe Glu Leu Cys Lys Thr Thr Phe Pro Thr Phe Thr Ile Arg Gly Val
            100                 105                 110

Glu Ala Asp Asp Met Ala Ala Tyr Ile Val Lys Leu Ile Gly His Leu
        115                 120                 125

Tyr Asp His Val Trp Leu Ile Ser Thr Asp Gly Asp Trp Asp Thr Leu
    130                 135                 140

Leu Thr Asp Lys Val Ser Arg Phe Ser Phe Thr Thr Arg Arg Glu Tyr
145                 150                 155                 160
```

```
His Leu Arg Asp Met Tyr Glu His His Asn Val Asp Val Glu Gln
            165                 170                 175

Phe Ile Ser Leu Lys Ala Ile Met Gly Asp Leu Gly Asp Asn Ile Arg
        180                 185                 190

Gly Val Glu Gly Ile Gly Ala Lys Arg Gly Tyr Asn Ile Ile Arg Glu
            195                 200                 205

Phe Gly Asn Val Leu Asp Ile Ile Asp Gln Leu Pro Leu Pro Gly Lys
210                 215                 220

Gln Lys Tyr Ile Gln Asn Leu Asn Ala Ser Glu Leu Leu Phe Arg
225                 230                 235                 240

Asn Leu Ile Leu Val Asp Leu Pro Thr Tyr Cys Val Asp Ala Ile Ala
                245                 250                 255

Ala Val Gly Gln Asp Val Leu Asp Lys Phe Thr Lys Asp Ile Leu Glu
            260                 265                 270

Ile Ala Glu Gln
        275

<210> SEQ ID NO 16
<211> LENGTH: 226
<212> TYPE: PRT
<213> ORGANISM: Artificial Sequence
<220> FEATURE:
<223> OTHER INFORMATION: Lambda exonuclease

<400> SEQUENCE: 16

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225
```

```
<210> SEQ ID NO 17
<211> LENGTH: 80
<212> TYPE: PRT
<213> ORGANISM: Artificial Sequence
<220> FEATURE:
<223> OTHER INFORMATION: Exonuclease VII small unit

<400> SEQUENCE: 17

Met Pro Lys Lys Asn Glu Ala Pro Ala Ser Phe Glu Lys Ala Leu Ser
1               5                   10                  15

Glu Leu Glu Gln Ile Val Thr Arg Leu Glu Ser Gly Asp Leu Pro Leu
            20                  25                  30

Glu Glu Ala Leu Asn Glu Phe Glu Arg Gly Val Gln Leu Ala Arg Gln
        35                  40                  45

Gly Gln Ala Lys Leu Gln Gln Ala Glu Gln Arg Val Gln Ile Leu Leu
    50                  55                  60

Ser Asp Asn Glu Asp Ala Ser Leu Thr Pro Phe Thr Pro Asp Asn Glu
65                  70                  75                  80

<210> SEQ ID NO 18
<211> LENGTH: 456
<212> TYPE: PRT
<213> ORGANISM: Artificial Sequence
<220> FEATURE:
<223> OTHER INFORMATION: Exonuclease VII large unit

<400> SEQUENCE: 18

Met Leu Pro Ser Gln Ser Pro Ala Ile Phe Thr Val Ser Arg Leu Asn
1               5                   10                  15

Gln Thr Val Arg Leu Leu Leu Glu His Glu Met Gly Gln Val Trp Ile
            20                  25                  30

Ser Gly Glu Ile Ser Asn Phe Thr Gln Pro Ala Ser Gly His Trp Tyr
        35                  40                  45

Phe Thr Leu Lys Asp Asp Thr Ala Gln Val Arg Cys Ala Met Phe Arg
    50                  55                  60

Asn Ser Asn Arg Arg Val Thr Phe Arg Pro Gln His Gly Gln Gln Val
65                  70                  75                  80

Leu Val Arg Ala Asn Ile Thr Leu Tyr Glu Pro Arg Gly Asp Tyr Gln
                85                  90                  95

Ile Ile Val Glu Ser Met Gln Pro Ala Gly Glu Gly Leu Leu Gln Gln
            100                 105                 110

Lys Tyr Glu Gln Leu Lys Ala Lys Leu Gln Ala Glu Gly Leu Phe Asp
        115                 120                 125

Gln Gln Tyr Lys Lys Pro Leu Pro Ser Pro Ala His Cys Val Gly Val
    130                 135                 140

Ile Thr Ser Lys Thr Gly Ala Ala Leu His Asp Ile Leu His Val Leu
145                 150                 155                 160

Lys Arg Arg Asp Pro Ser Leu Pro Val Ile Ile Tyr Pro Ala Ala Val
                165                 170                 175

Gln Gly Asp Asp Ala Pro Gly Gln Ile Val Arg Ala Ile Glu Leu Ala
            180                 185                 190

Asn Gln Arg Asn Glu Cys Asp Val Leu Ile Val Gly Arg Gly Gly Gly
        195                 200                 205

Ser Leu Glu Asp Leu Trp Ser Phe Asn Asp Glu Arg Val Ala Arg Ala
    210                 215                 220

Ile Phe Thr Ser Arg Ile Pro Val Val Ser Ala Val Gly His Glu Thr
225                 230                 235                 240
```

Asp Val Thr Ile Ala Asp Phe Val Ala Asp Leu Arg Ala Pro Thr Pro
                245                 250                 255

Ser Ala Ala Ala Glu Val Val Ser Arg Asn Gln Gln Glu Leu Leu Arg
            260                 265                 270

Gln Val Gln Ser Thr Arg Gln Arg Leu Glu Met Ala Met Asp Tyr Tyr
        275                 280                 285

Leu Ala Asn Arg Thr Arg Arg Phe Thr Gln Ile His His Arg Leu Gln
    290                 295                 300

Gln Gln His Pro Gln Leu Arg Leu Ala Arg Gln Gln Thr Met Leu Glu
305                 310                 315                 320

Arg Leu Gln Lys Arg Met Ser Phe Ala Leu Glu Asn Gln Leu Lys Arg
                325                 330                 335

Thr Gly Gln Gln Gln Gln Arg Leu Thr Gln Arg Leu Asn Gln Gln Asn
            340                 345                 350

Pro Gln Pro Lys Ile His Arg Ala Gln Thr Arg Ile Gln Gln Leu Glu
        355                 360                 365

Tyr Arg Leu Ala Glu Thr Leu Arg Ala Gln Leu Ser Ala Thr Arg Glu
    370                 375                 380

Arg Phe Gly Asn Ala Val Thr His Leu Glu Ala Val Ser Pro Leu Ser
385                 390                 395                 400

Thr Leu Ala Arg Gly Tyr Ser Val Thr Thr Ala Thr Asp Gly Asn Val
                405                 410                 415

Leu Lys Lys Val Lys Gln Val Lys Ala Gly Glu Met Leu Thr Thr Arg
            420                 425                 430

Leu Glu Asp Gly Trp Ile Glu Ser Glu Val Lys Asn Ile Gln Pro Val
        435                 440                 445

Lys Lys Ser Arg Lys Lys Val His
    450                 455

<210> SEQ ID NO 19
<211> LENGTH: 4101
<212> TYPE: DNA
<213> ORGANISM: Artificial Sequence
<220> FEATURE:
<223> OTHER INFORMATION: Cas9 nucleotides sequence of Streptococcus
      pyogenes M1 GAS

<400> SEQUENCE: 19
gacaagaagt acagcatcgg cctggacatc ggcaccaact ctgtgggctg ggccgtgatc      60
accgacgagt acaaggtgcc cagcaagaaa ttcaaggtgc tgggcaacac cgaccggcac     120
agcatcaaga gaacctgat cggagccctg ctgttcgaca gcggcgaaac agccgaggcc     180
acccggctga agaaccgc cagaagaaga tacaccagac ggaagaaccg gatctgctat     240
ctgcaagaga tcttcagcaa cgagatggcc aaggtggacg acagcttctt ccacagactg     300
gaagagtcct tcctggtgga agaggataag aagcacgagc ggcacccat cttcggcaac     360 atcgtggacg aggtggccta ccacgagaag taccccacca tctaccacct gagaaagaaa     420
ctggtggaca gcaccgacaa ggccgacctg cggctgatct atctggccct ggcccacatg     480
atcaagttcc ggggccactt cctgatcgag ggcgacctga accccgacaa cagcgacgtg     540
gacaagctgt tcatccagct ggtgcagacc tacaaccagc tgttcgagga aaaccccatc     600
aacgccagcg gcgtggacgc caaggccatc ctgtctgcca gactgagcaa gagcagacgg     660
ctggaaaatc tgatcgccca gctgcccggc gagaagaaga tggcctgtt cggaaacctg     720 attgccctga gcctgggcct gaccccaac ttcaagagca acttcgacct ggccgaggat     780

```
gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg ccccctgag cgcctctatg     960 atcaagagat acgacgagca ccaccaggac ctgaccctgc tgaaagctct cgtgcggcag   1020
cagctgcctg agaagtacaa agagattttc ttcgaccaga gcaagaacgg ctacgccggc   1080
tacattgacg gcggagccag ccaggaagag ttctacaagt tcatcaagcc catcctggaa   1140
aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga ttttacccat tcctgaagg acaaccggga aaagatcgag    1320
aagatcctga ccttccgcat ccctactac gtgggccctc tggccagggg aaacagcaga    1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga aaagcccgc cttcctgagc    1620 ggcgagcaga aaaaggccat cgtggacctg ctgttcaaga ccaaccggaa agtgaccgtg   1680
aagcagctga agaggactca cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa aacgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100 ctgacctta aagaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca agcccgagaa catcgtgatc   2280
gaaatggcca gagagaacca gaccacccag aagggacaga gaacagccg cgagagaatg   2340 aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggaccatatc   2520
gtgcctcaga gctttctgaa ggacgactcc atcgacaaca aggtgctgac cagaagcgac   2580
aagaaccggg gcaagagcga caacgtgccc tccgaagagg tcgtgaagaa gatgaagaac   2640
tactggcggc agctgctgaa cgccaagctg attacccaga gaaagttcga caatctgacc   2700
aaggccgaga gggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
ctggtgtccg atttccggaa ggatttccag ttttacaaag tgcgcgagat caacaactac   2940
caccacgccc acgacgccta cctgaacgcc gtcgtgggaa ccgccctgat caaaaagtac   3000
cctaagctgg aaagcgagtt cgtgtacggc gactacaagg tgtacgacgt gcggaagatg   3060
atcgccaaga gcgagcagga aatcggcaag gctaccgcca agtacttctt ctacagcaac   3120
```

-continued

```
atcatgaact tttcaagac cgagattacc ctggccaacg gcgagatccg aagcggcct      3180 ctgatcgaga caaacggcga aaccggggag atcgtgtggg ataagggccg ggattttgcc      3240
accgtgcgga aagtgctgag catgccccaa gtgaatatcg tgaaaaagac cgaggtgcag      3300
acaggcggct tcagcaaaga gtctatcctg cccaagagga cagcgataa gctgatcgcc      3360 agaaagaagg actgggaccc taagaagtac ggcggcttcg acagccccac cgtggcctat      3420
tctgtgctgg tggtggccaa agtggaaaag ggcaagtcca agaaactgaa gagtgtgaaa      3480
gagctgctgg ggatcaccat catggaaaga agcagcttcg agaagaatcc catcgacttt      3540
ctggaagcca agggctacaa agaagtgaaa aaggacctga tcatcaagct gcctaagtac      3600
tccctgttcg agctggaaaa cggccggaag agaatgctgg cctctgccgg cgaactgcag      3660
aagggaaacg aactggccct gccctccaaa tatgtgaact tcctgtacct ggccagccac      3720
tatgagaagc tgaagggctc ccccgaggat aatgagcaga acagctgtt tgtggaacag      3780 cacaagcact acctggacga gatcatcgag cagatcagcg agttctccaa gagagtgatc      3840
ctggccgacg ctaatctgga caaagtgctg tccgcctaca acaagcaccg ggataagccc      3900
atcagagagc aggccgagaa tatcatccac ctgtttaccc tgaccaatct gggagcccct      3960
gccgccttca gtactttga caccaccatc gaccggaaga ggtacaccag caccaaagag      4020
gtgctggacg ccaccctgat ccaccagagc atcaccggcc tgtacgagac acggatcgac      4080
ctgtctcagc tgggaggcga c                                             4101
```

<210> SEQ ID NO 20
<211> LENGTH: 1450
<212> TYPE: PRT
<213> ORGANISM: Artificial Sequence
<220> FEATURE:
<223> OTHER INFORMATION: Cas9 amino acids sequence of Streptococcus
      pyogenes M1 GAS

<400> SEQUENCE: 20

```
Asp Tyr Lys Asp His Asp Gly Asp Tyr Lys Asp His Asp Ile Asp Tyr
1               5                   10                  15

Lys Asp Asp Asp Asp Lys Met Glu Thr Ala Pro Lys Lys Lys Arg Lys
            20                  25                  30

Val Gly Ile His Gly Val Pro Ala Ala Asp Lys Lys Tyr Ser Ile Gly
        35                  40                  45

Leu Asp Ile Gly Thr Asn Ser Val Gly Trp Ala Val Ile Thr Asp Glu
    50                  55                  60

Tyr Lys Val Pro Ser Lys Lys Phe Lys Val Leu Gly Asn Thr Asp Arg
65                  70                  75                  80

His Ser Ile Lys Lys Asn Leu Ile Gly Ala Leu Leu Phe Asp Ser Gly
                85                  90                  95

Glu Thr Ala Glu Ala Thr Arg Leu Lys Arg Thr Ala Arg Arg Arg Tyr
            100                 105                 110

Thr Arg Arg Lys Asn Arg Ile Cys Tyr Leu Gln Glu Ile Phe Ser Asn
        115                 120                 125

Glu Met Glu Thr Ala Lys Val Asp Asp Ser Phe Phe His Arg Leu Glu
    130                 135                 140

Glu Ser Phe Leu Val Glu Glu Asp Lys Lys His Glu Arg His Pro Ile
145                 150                 155                 160

Phe Gly Asn Ile Val Asp Glu Val Ala Tyr His Glu Lys Tyr Pro Thr
                165                 170                 175

Ile Tyr His Leu Arg Lys Lys Leu Val Asp Ser Thr Asp Lys Ala Asp
```

```
                180                185                190
Leu Arg Leu Ile Tyr Leu Ala Leu Ala His Met Glu Thr Ile Lys Phe
            195                200                205
Arg Gly His Phe Leu Ile Glu Gly Asp Leu Asn Pro Asp Asn Ser Asp
            210                215                220
Val Asp Lys Leu Phe Ile Gln Leu Val Gln Thr Tyr Asn Gln Leu Phe
225                230                235                240
Glu Glu Asn Pro Ile Asn Ala Ser Gly Val Asp Ala Lys Ala Ile Leu
                245                250                255
Ser Ala Arg Leu Ser Lys Ser Arg Arg Leu Glu Asn Leu Ile Ala Gln
            260                265                270
Leu Pro Gly Glu Lys Lys Asn Gly Leu Phe Gly Asn Leu Ile Ala Leu
            275                280                285
Ser Leu Gly Leu Thr Pro Asn Phe Lys Ser Asn Phe Asp Leu Ala Glu
            290                295                300
Asp Ala Lys Leu Gln Leu Ser Lys Asp Thr Tyr Asp Asp Asp Leu Asp
305                310                315                320
Asn Leu Leu Ala Gln Ile Gly Asp Gln Tyr Ala Asp Leu Phe Leu Ala
                325                330                335
Ala Lys Asn Leu Ser Asp Ala Ile Leu Leu Ser Asp Ile Leu Arg Val
            340                345                350
Asn Thr Glu Ile Thr Lys Ala Pro Leu Ser Ala Ser Met Glu Thr Ile
            355                360                365
Lys Arg Tyr Asp Glu His His Gln Asp Leu Thr Leu Leu Lys Ala Leu
            370                375                380
Val Arg Gln Gln Leu Pro Glu Lys Tyr Lys Glu Ile Phe Phe Asp Gln
385                390                395                400
Ser Lys Asn Gly Tyr Ala Gly Tyr Ile Asp Gly Gly Ala Ser Gln Glu
                405                410                415
Glu Phe Tyr Lys Phe Ile Lys Pro Ile Leu Glu Lys Met Glu Thr Asp
            420                425                430
Gly Thr Glu Glu Leu Leu Val Lys Leu Asn Arg Glu Asp Leu Leu Arg
            435                440                445
Lys Gln Arg Thr Phe Asp Asn Gly Ser Ile Pro His Gln Ile His Leu
            450                455                460
Gly Glu Leu His Ala Ile Leu Arg Arg Gln Glu Asp Phe Tyr Pro Phe
465                470                475                480
Leu Lys Asp Asn Arg Glu Lys Ile Glu Lys Ile Leu Thr Phe Arg Ile
                485                490                495
Pro Tyr Tyr Val Gly Pro Leu Ala Arg Gly Asn Ser Arg Phe Ala Trp
            500                505                510
Met Glu Thr Thr Arg Lys Ser Glu Thr Ile Thr Pro Trp Asn Phe
            515                520                525
Glu Glu Val Val Asp Lys Gly Ala Ser Ala Gln Ser Phe Ile Glu Arg
            530                535                540
Met Glu Thr Thr Asn Phe Asp Lys Asn Leu Pro Asn Glu Lys Val Leu
545                550                555                560
Pro Lys His Ser Leu Leu Tyr Glu Tyr Phe Thr Val Tyr Asn Glu Leu
                565                570                575
Thr Lys Val Lys Tyr Val Thr Glu Gly Met Glu Thr Arg Lys Pro Ala
            580                585                590
Phe Leu Ser Gly Glu Gln Lys Lys Ala Ile Val Asp Leu Leu Phe Lys
            595                600                605
```

```
Thr Asn Arg Lys Val Thr Val Lys Gln Leu Lys Glu Asp Tyr Phe Lys
    610                 615                 620

Lys Ile Glu Cys Phe Asp Ser Val Glu Ile Ser Gly Val Glu Asp Arg
625                 630                 635                 640

Phe Asn Ala Ser Leu Gly Thr Tyr His Asp Leu Leu Lys Ile Ile Lys
                645                 650                 655

Asp Lys Asp Phe Leu Asp Asn Glu Glu Asn Glu Asp Ile Leu Glu Asp
                660                 665                 670

Ile Val Leu Thr Leu Thr Leu Phe Glu Asp Arg Glu Met Glu Thr Ile
            675                 680                 685

Glu Glu Arg Leu Lys Thr Tyr Ala His Leu Phe Asp Asp Lys Val Met
690                 695                 700

Glu Thr Lys Gln Leu Lys Arg Arg Arg Tyr Thr Gly Trp Gly Arg Leu
705                 710                 715                 720

Ser Arg Lys Leu Ile Asn Gly Ile Arg Asp Lys Gln Ser Gly Lys Thr
                725                 730                 735

Ile Leu Asp Phe Leu Lys Ser Asp Gly Phe Ala Asn Arg Asn Phe Met
                740                 745                 750

Glu Thr Gln Leu Ile His Asp Asp Ser Leu Thr Phe Lys Glu Asp Ile
            755                 760                 765

Gln Lys Ala Gln Val Ser Gly Gln Gly Asp Ser Leu His Glu His Ile
770                 775                 780

Ala Asn Leu Ala Gly Ser Pro Ala Ile Lys Lys Gly Ile Leu Gln Thr
785                 790                 795                 800

Val Lys Val Val Asp Glu Leu Val Lys Val Met Glu Thr Gly Arg His
                805                 810                 815

Lys Pro Glu Asn Ile Val Ile Glu Met Glu Thr Ala Arg Glu Asn Gln
                820                 825                 830

Thr Thr Gln Lys Gly Gln Lys Asn Ser Arg Glu Arg Met Glu Thr Lys
            835                 840                 845

Arg Ile Glu Glu Gly Ile Lys Glu Leu Gly Ser Gln Ile Leu Lys Glu
850                 855                 860

His Pro Val Glu Asn Thr Gln Leu Gln Asn Glu Lys Leu Tyr Leu Tyr
865                 870                 875                 880

Tyr Leu Gln Asn Gly Arg Asp Met Glu Thr Tyr Val Asp Gln Glu Leu
                885                 890                 895

Asp Ile Asn Arg Leu Ser Asp Tyr Asp Val Asp His Ile Val Pro Gln
                900                 905                 910

Ser Phe Leu Lys Asp Asp Ser Ile Asp Asn Lys Val Leu Thr Arg Ser
            915                 920                 925

Asp Lys Asn Arg Gly Lys Ser Asp Asn Val Pro Ser Glu Glu Val Val
930                 935                 940

Lys Lys Met Glu Thr Lys Asn Tyr Trp Arg Gln Leu Leu Asn Ala Lys
945                 950                 955                 960

Leu Ile Thr Gln Arg Lys Phe Asp Asn Leu Thr Lys Ala Glu Arg Gly
                965                 970                 975

Gly Leu Ser Glu Leu Asp Lys Ala Gly Phe Ile Lys Arg Gln Leu Val
            980                 985                 990

Glu Thr Arg Gln Ile Thr Lys His Val Ala Gln Ile Leu Asp Ser Arg
        995                 1000                1005

Met Glu Thr Asn Thr Lys Tyr Asp Glu Asn Asp Lys Leu Ile Arg Glu
    1010                1015                1020
```

```
Val Lys Val Ile Thr Leu Lys Ser Lys Leu Val Ser Asp Phe Arg Lys
1025                1030                1035                1040

Asp Phe Gln Phe Tyr Lys Val Arg Glu Ile Asn Asn Tyr His His Ala
            1045                1050                1055

His Asp Ala Tyr Leu Asn Ala Val Val Gly Thr Ala Leu Ile Lys Lys
        1060                1065                1070

Tyr Pro Lys Leu Glu Ser Glu Phe Val Tyr Gly Asp Tyr Lys Val Tyr
    1075                1080                1085

Asp Val Arg Lys Met Glu Thr Ile Ala Lys Ser Glu Gln Glu Ile Gly
1090                1095                1100

Lys Ala Thr Ala Lys Tyr Phe Phe Tyr Ser Asn Ile Met Glu Thr Asn
1105                1110                1115                1120

Phe Phe Lys Thr Glu Ile Thr Leu Ala Asn Gly Glu Ile Arg Lys Arg
            1125                1130                1135

Pro Leu Ile Glu Thr Asn Gly Glu Thr Gly Glu Ile Val Trp Asp Lys
        1140                1145                1150

Gly Arg Asp Phe Ala Thr Val Arg Lys Val Leu Ser Met Glu Thr Pro
    1155                1160                1165

Gln Val Asn Ile Val Lys Lys Thr Glu Val Gln Thr Gly Gly Phe Ser
1170                1175                1180

Lys Glu Ser Ile Leu Pro Lys Arg Asn Ser Asp Lys Leu Ile Ala Arg
1185                1190                1195                1200

Lys Lys Asp Trp Asp Pro Lys Lys Tyr Gly Gly Phe Asp Ser Pro Thr
            1205                1210                1215

Val Ala Tyr Ser Val Leu Val Val Ala Lys Val Glu Lys Gly Lys Ser
        1220                1225                1230

Lys Lys Leu Lys Ser Val Lys Glu Leu Leu Gly Ile Thr Ile Met Glu
    1235                1240                1245

Thr Glu Arg Ser Ser Phe Glu Lys Asn Pro Ile Asp Phe Leu Glu Ala
1250                1255                1260

Lys Gly Tyr Lys Glu Val Lys Lys Asp Leu Ile Ile Lys Leu Pro Lys
1265                1270                1275                1280

Tyr Ser Leu Phe Glu Leu Glu Asn Gly Arg Lys Arg Met Glu Thr Leu
            1285                1290                1295

Ala Ser Ala Gly Glu Leu Gln Lys Gly Asn Glu Leu Ala Leu Pro Ser
        1300                1305                1310

Lys Tyr Val Asn Phe Leu Tyr Leu Ala Ser His Tyr Glu Lys Leu Lys
    1315                1320                1325

Gly Ser Pro Glu Asp Asn Glu Gln Lys Gln Leu Phe Val Glu Gln His
1330                1335                1340

Lys His Tyr Leu Asp Glu Ile Ile Glu Gln Ile Ser Glu Phe Ser Lys
1345                1350                1355                1360

Arg Val Ile Leu Ala Asp Ala Asn Leu Asp Lys Val Leu Ser Ala Tyr
            1365                1370                1375

Asn Lys His Arg Asp Lys Pro Ile Arg Glu Gln Ala Glu Asn Ile Ile
        1380                1385                1390

His Leu Phe Thr Leu Thr Asn Leu Gly Ala Pro Ala Ala Phe Lys Tyr
    1395                1400                1405

Phe Asp Thr Thr Ile Asp Arg Lys Arg Tyr Thr Ser Thr Lys Glu Val
    1410                1415                1420

Leu Asp Ala Thr Leu Ile His Gln Ser Ile Thr Gly Leu Tyr Glu Thr
1425                1430                1435                1440

Arg Ile Asp Leu Ser Gln Leu Gly Gly Asp
```

1445          1450

<210> SEQ ID NO 21
<211> LENGTH: 3903
<212> TYPE: DNA
<213> ORGANISM: Artificial Sequence
<220> FEATURE:
<223> OTHER INFORMATION: Cpf1 nucleotides sequences, FnCpf1, NCBI
      accession no. CP009633.1

<400> SEQUENCE: 21

| | | | | | |
|---|---|---|---|---|---|
| atgtcaattt | atcaagaatt | tgttaataaa | tatagtttaa | gtaaaactct | aagatttgag | 60 |
| ttaatcccac | agggtaaaac | acttgaaaac | ataaaagcaa | gaggtttgat | tttagatgat | 120 |
| gagaaaagag | ctaaagacta | caaaaaggct | aaacaaataa | ttgataaata | tcatcagttt | 180 |
| tttatagagg | agatattaag | ttcggtttgt | attagcgaag | atttattaca | aaactattct | 240 |
| gatgtttatt | ttaaacttaa | aaagagtgat | gatgataatc | tacaaaaaga | ttttaaaagt | 300 |
| gcaaaagata | cgataaagaa | acaaatatct | gaatatataa | aggactcaga | gaaatttaag | 360 |
| aatttgttta | atcaaaacct | tatcgatgct | aaaaaagggc | aagagtcaga | tttaattcta | 420 |
| tggctaaagc | aatctaagga | taatggtata | gaactatttta | aagccaatag | tgatatcaca | 480 |
| gatatagatg | aggcgttaga | aataatcaaa | tcttttaaag | gttggacaac | ttattttaag | 540 |
| ggttttcatg | aaaatagaaa | aaatgtttat | agtagcaatg | atattcctac | atctattatt | 600 |
| tataggatag | tagatgataa | tttgcctaaa | tttctagaaa | ataaagctaa | gtatgagagt | 660 |
| ttaaaagaca | agctccaga | agctataaac | tatgaacaaa | ttaaaaaaga | tttggcagaa | 720 |
| gagctaacct | ttgatattga | ctacaaaaca | tctgaagtta | tcaaagagt | ttttcactt | 780 |
| gatgaagttt | ttgagatagc | aaactttaat | aattatctaa | atcaaagtgg | tattactaaa | 840 |
| tttaatacta | ttattggtgg | taaatttgta | aatggtgaaa | atacaaagag | aaaaggtata | 900 |
| aatgaatata | taaatctata | ctcacagcaa | ataaatgata | aaacactcaa | aaatataaa | 960 |
| atgagtgttt | tatttaagca | aattttaagt | gatacagaat | ctaaatcttt | tgtaattgat | 1020 |
| aagttagaag | atgatagtga | tgtagttaca | acgatgcaaa | gttttttatga | gcaaatagca | 1080 |
| gcttttaaaa | cagtagaaga | aaaatctatt | aaagaaacac | tatctttatt | atttgatgat | 1140 |
| ttaaaagctc | aaaaacttga | tttgagtaaa | atttattttta | aaatgataaa | atctcttact | 1200 |
| gatctatcac | aacaagtttt | tgatgattat | agtgttattg | gtacagcggt | actagaatat | 1260 |
| ataactcaac | aaatagcacc | taaaaatctt | gataaccccta | gtaagaaaga | gcaagaatta | 1320 |
| atagccaaaa | aaactgaaaa | agcaaaatac | ttatctctag | aaactataaa | gcttgcctta | 1380 |
| gaagaattta | ataagcatag | agatatagat | aaacagtgta | ggtttgaaga | aatacttgca | 1440 |
| aactttgcgg | ctattccgat | gatatttgat | gaaatagctc | aaaacaaaga | caatttggca | 1500 |
| cagatatcta | tcaaatatca | aaatcaaggt | aaaaaagacc | tacttcaagc | tagtgcggaa | 1560 |
| gatgatgtta | agctatcaa | ggatctttta | gatcaaacta | ataatctctt | acataaaacta | 1620 |
| aaaatatttc | atattagtca | gtcagaagat | aaggcaaata | ttttagacaa | ggatgagcat | 1680 |
| ttttatctag | tatttgagga | gtgctacttt | gagctagcga | atatagtgcc | tctttataac | 1740 |
| aaaattagaa | actatataac | tcaaaagcca | tatagtgatg | agaaatttaa | gctcaatttt | 1800 |
| gagaactcga | ctttggctaa | tggttgggat | aaaaataaag | agcctgacaa | tacggcaatt | 1860 |
| ttatttatca | aagatgataa | atattatctg | ggtgtgatga | ataagaaaaa | taacaaaata | 1920 |
| tttgatgata | aagctatcaa | agaaaataaa | ggcgagggtt | ataaaaaaat | tgtttataaa | 1980 |

| | | |
|---|---|---|
| cttttacctg gcgcaaataa aatgttacct aaggttttct tttctgctaa atctataaaa | 2040 | |
| ttttataatc ctagtgaaga tatacttaga ataagaaatc attccacaca tacaaaaaat | 2100 | |
| ggtagtcctc aaaaaggata tgaaaaattt gagtttaata ttgaagattg ccgaaaattt | 2160 | |
| atagatttt ataaacagtc tataagtaag catccggagt ggaaagattt tggatttaga | 2220 | |
| ttttctgata ctcaaagata taattctata gatgaatttt atagagaagt tgaaaatcaa | 2280 | |
| ggctacaaac taacttttga aaatatatca gagagctata ttgatagcgt agttaatcag | 2340 | |
| ggtaaattgt acctattcca atctataat aaagattttt cagcttatag caaagggcga | 2400 | |
| ccaaatctac atactttata ttggaaagcg ctgtttgatg agagaaatct tcaagatgtg | 2460 | |
| gtttataagc taaatggtga ggcagagctt tttatcgta aacaatcaat acctaaaaaa | 2520 | |
| atcactcacc cagctaaaga ggcaatagct aataaaaaca aagataatcc taaaaaagag | 2580 | |
| agtgttttg aatatgattt aatcaaagat aaacgcttta ctgaagataa gttttctttt | 2640 | |
| cactgtccta ttacaatcaa ttttaaatct agtggagcta ataagtttaa tgatgaaatc | 2700 | |
| aatttattgc taaagaaaa agcaaatgat gttcatatat taagtataga tagaggtgaa | 2760 | |
| agacatttag cttactatac tttggtagat ggtaaaggca atatcatcaa acaagatact | 2820 | |
| ttcaacatca ttggtaatga tagaatgaaa acaaactacc atgataagct tgctgcaata | 2880 | |
| gagaaagata gggattcagc taggaaagac tggaaaaaga taataacat caaagagatg | 2940 | |
| aaagagggct atctatctca ggtagttcat gaaatagcta agctagttat agagtataat | 3000 | |
| gctattgtgg tttttgagga tttaaattt ggatttaaaa gagggcgttt caaggtagag | 3060 | |
| aagcaggtct atcaaaagtt agaaaaaatg ctaattgaga aactaaacta tctagttttc | 3120 | |
| aaagataatg agtttgataa aactggggga gtgcttagag cttatcagct aacagcacct | 3180 | |
| tttgagactt ttaaaagat gggtaaacaa acaggtatta tctactatgt accagctggt | 3240 | |
| tttacttcaa aaatttgtcc tgtaactggt tttgtaaatc agttatatcc taagtatgaa | 3300 | |
| agtgtcagca atctcaaga gttctttagt aagtttgaca agatttgtta taaccttgat | 3360 | |
| aagggctatt ttgagtttag ttttgattat aaaaactttg gtgacaaggc tgccaaaggc | 3420 | |
| aagtggacta tagctagctt tgggagtaga ttgattaact ttagaaattc agataaaaat | 3480 | |
| cataattggg atactcgaga gtttatccca actaaagagt tggagaaatt gctaaaagat | 3540 | |
| tattctatcg aatatgggca tggcgaatgt atcaaagcag ctatttgcgg tgagagcgac | 3600 | |
| aaaaagtttt ttgctaagct aactagtgtc ctaaatacta tcttacaaat gcgtaactca | 3660 | |
| aaaacaggta ctgagttaga ttatctaatt tcaccagtag cagatgtaaa tggcaatttc | 3720 | |
| tttgattcgc gacaggcgcc aaaaaatatg cctcaagatg ctgatgccaa tggtgcttat | 3780 | |
| catattgggc taaaggtct gatgctacta ggtaggatca aaataatca agagggcaaa | 3840 | |
| aaactcaatt tggttatcaa aaatgaagag tattttgagt tcgtgcagaa taggaataac | 3900 | |
| taa | 3903 | |

<210> SEQ ID NO 22
<211> LENGTH: 1300
<212> TYPE: PRT
<213> ORGANISM: Artificial Sequence
<220> FEATURE:
<223> OTHER INFORMATION: Cpf1 amino acids sequences, FnCpf1, NCBI
      accession no. CP009633.1

<400> SEQUENCE: 22

Met Ser Ile Tyr Gln Glu Phe Val Asn Lys Tyr Ser Leu Ser Lys Thr
1               5                   10                  15

```
Leu Arg Phe Glu Leu Ile Pro Gln Gly Lys Thr Leu Glu Asn Ile Lys
             20                  25                  30

Ala Arg Gly Leu Ile Leu Asp Glu Lys Arg Ala Lys Asp Tyr Lys
         35                  40                  45

Lys Ala Lys Gln Ile Ile Asp Lys Tyr His Gln Phe Phe Ile Glu Glu
50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                 85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430
```

```
Pro Ser Lys Lys Glu Gln Glu Leu Ile Ala Lys Lys Thr Glu Lys Ala
        435                 440                 445
Lys Tyr Leu Ser Leu Glu Thr Ile Lys Leu Ala Leu Glu Glu Phe Asn
    450                 455                 460
Lys His Arg Asp Ile Asp Lys Gln Cys Arg Phe Glu Glu Ile Leu Ala
465                 470                 475                 480
Asn Phe Ala Ala Ile Pro Met Ile Phe Asp Glu Ile Ala Gln Asn Lys
                485                 490                 495
Asp Asn Leu Ala Gln Ile Ser Ile Lys Tyr Gln Asn Gln Gly Lys Lys
            500                 505                 510
Asp Leu Leu Gln Ala Ser Ala Glu Asp Asp Val Lys Ala Ile Lys Asp
        515                 520                 525
Leu Leu Asp Gln Thr Asn Asn Leu Leu His Lys Leu Lys Ile Phe His
    530                 535                 540
Ile Ser Gln Ser Glu Asp Lys Ala Asn Ile Leu Asp Lys Asp Glu His
545                 550                 555                 560
Phe Tyr Leu Val Phe Glu Glu Cys Tyr Phe Glu Leu Ala Asn Ile Val
                565                 570                 575
Pro Leu Tyr Asn Lys Ile Arg Asn Tyr Ile Thr Gln Lys Pro Tyr Ser
            580                 585                 590
Asp Glu Lys Phe Lys Leu Asn Phe Glu Asn Ser Thr Leu Ala Asn Gly
        595                 600                 605
Trp Asp Lys Asn Lys Glu Pro Asp Asn Thr Ala Ile Leu Phe Ile Lys
    610                 615                 620
Asp Asp Lys Tyr Tyr Leu Gly Val Met Asn Lys Lys Asn Asn Lys Ile
625                 630                 635                 640
Phe Asp Asp Lys Ala Ile Lys Glu Asn Lys Gly Glu Gly Tyr Lys Lys
                645                 650                 655
Ile Val Tyr Lys Leu Leu Pro Gly Ala Asn Lys Met Leu Pro Lys Val
            660                 665                 670
Phe Phe Ser Ala Lys Ser Ile Lys Phe Tyr Asn Pro Ser Glu Asp Ile
        675                 680                 685
Leu Arg Ile Arg Asn His Ser Thr His Thr Lys Asn Gly Ser Pro Gln
    690                 695                 700
Lys Gly Tyr Glu Lys Phe Glu Phe Asn Ile Glu Asp Cys Arg Lys Phe
705                 710                 715                 720
Ile Asp Phe Tyr Lys Gln Ser Ile Ser Lys His Pro Glu Trp Lys Asp
                725                 730                 735
Phe Gly Phe Arg Phe Ser Asp Thr Gln Arg Tyr Asn Ser Ile Asp Glu
            740                 745                 750
Phe Tyr Arg Glu Val Glu Asn Gln Gly Tyr Lys Leu Thr Phe Glu Asn
        755                 760                 765
Ile Ser Glu Ser Tyr Ile Asp Ser Val Val Asn Gln Gly Lys Leu Tyr
    770                 775                 780
Leu Phe Gln Ile Tyr Asn Lys Asp Phe Ser Ala Tyr Ser Lys Gly Arg
785                 790                 795                 800
Pro Asn Leu His Thr Leu Tyr Trp Lys Ala Leu Phe Asp Glu Arg Asn
                805                 810                 815
Leu Gln Asp Val Val Tyr Lys Leu Asn Gly Glu Ala Glu Leu Phe Tyr
            820                 825                 830
Arg Lys Gln Ser Ile Pro Lys Lys Ile Thr His Pro Ala Lys Glu Ala
        835                 840                 845
Ile Ala Asn Lys Asn Lys Asp Asn Pro Lys Lys Glu Ser Val Phe Glu
```

```
                850                 855                 860
Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
                900                 905                 910

Ile Leu Ser Ile Asp Arg Gly Glu Arg His Leu Ala Tyr Tyr Thr Leu
                915                 920                 925

Val Asp Gly Lys Gly Asn Ile Ile Lys Gln Asp Thr Phe Asn Ile Ile
            930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
                965                 970                 975

Ile Lys Glu Met Lys Glu Gly Tyr Leu Ser Gln Val Val His Glu Ile
                980                 985                 990

Ala Lys Leu Val Ile Glu Tyr Asn Ala Ile Val Phe Glu Asp Leu
            995                 1000                1005

Asn Phe Gly Phe Lys Arg Gly Arg Phe Lys Val Glu Lys Gln Val Tyr
            1010                1015                1020

Gln Lys Leu Glu Lys Met Leu Ile Glu Lys Leu Asn Tyr Leu Val Phe
1025                1030                1035                1040

Lys Asp Asn Glu Phe Asp Lys Thr Gly Gly Val Leu Arg Ala Tyr Gln
                1045                1050                1055

Leu Thr Ala Pro Phe Glu Thr Phe Lys Lys Met Gly Lys Gln Thr Gly
                1060                1065                1070

Ile Ile Tyr Tyr Val Pro Ala Gly Phe Thr Ser Lys Ile Cys Pro Val
            1075                1080                1085

Thr Gly Phe Val Asn Gln Leu Tyr Pro Lys Tyr Glu Ser Val Ser Lys
            1090                1095                1100

Ser Gln Glu Phe Phe Ser Lys Phe Asp Lys Ile Cys Tyr Asn Leu Asp
1105                1110                1115                1120

Lys Gly Tyr Phe Glu Phe Ser Phe Asp Tyr Lys Asn Phe Gly Asp Lys
                1125                1130                1135

Ala Ala Lys Gly Lys Trp Thr Ile Ala Ser Phe Gly Ser Arg Leu Ile
                1140                1145                1150

Asn Phe Arg Asn Ser Asp Lys Asn His Asn Trp Asp Thr Arg Glu Val
                1155                1160                1165

Tyr Pro Thr Lys Glu Leu Glu Lys Leu Leu Lys Asp Tyr Ser Ile Glu
            1170                1175                1180

Tyr Gly His Gly Glu Cys Ile Lys Ala Ala Ile Cys Gly Glu Ser Asp
1185                1190                1195                1200

Lys Lys Phe Phe Ala Lys Leu Thr Ser Val Leu Asn Thr Ile Leu Gln
                1205                1210                1215

Met Arg Asn Ser Lys Thr Gly Thr Glu Leu Asp Tyr Leu Ile Ser Pro
                1220                1225                1230

Val Ala Asp Val Asn Gly Asn Phe Phe Asp Ser Arg Gln Ala Pro Lys
            1235                1240                1245

Asn Met Pro Gln Asp Ala Asp Ala Asn Gly Ala Tyr His Ile Gly Leu
            1250                1255                1260

Lys Gly Leu Met Leu Leu Gly Arg Ile Lys Asn Asn Gln Glu Gly Lys
1265                1270                1275                1280
```

Lys Leu Asn Leu Val Ile Lys Asn Glu Glu Tyr Phe Glu Phe Val Gln
            1285                1290                1295

Asn Arg Asn Asn
            1300

<210> SEQ ID NO 23
<211> LENGTH: 3459
<212> TYPE: DNA
<213> ORGANISM: Artificial Sequence
<220> FEATURE:
<223> OTHER INFORMATION: C2C2 nucleotides sequences, Leptotrichia
      wadei's Cas13a

<400> SEQUENCE: 23

```
atgaaagtga ccaaggtcga cggcatcagc cacaagaagt acatcgaaga gggcaagctc    60
gtgaagtcca ccagcgagga aaaccggacc agcgagagac tgagcgagct gctgagcatc   120
cggctggaca tctacatcaa gaccccgac aacgcctccg aggaagagaa ccggatcaga   180
agagagaacc tgaagaagtt ctttagcaac aaggtgctgc acctgaagga cagcgtgctg   240
tatctgaaga accggaaaga aaagaacgcc gtgcaggaca gaactatag cgaagaggac   300 atcagcgagt cgacctgaa aaacaagaac agcttctccg tgctgaagaa gatcctgctg   360
aacgaggacg tgaactctga ggaactggaa atctttcgga aggacgtgga agccaagctg   420
aacaagatca cagcctgaa gtacagcttc gaagagaaca aggccaacta ccagaagatc   480
aacgagaaca acgtggaaaa agtgggcggc aagagcaagc ggaacatcat ctacgactac   540
tacagagaga gcgccaagcg caacgactac atcaacaacg tgcaggaagc cttcgacaag   600
ctgtataaga agaggatat cgagaaactg ttttttcctga tcgagaacag caagaagcac   660
gagaagtaca agatccgcga gtactatcac aagatcatcg gccggaagaa cgacaaagag   720
aacttcgcca agattatcta cgaagagatc cagaacgtga caacatcaa agagctgatt   780 gagaagatcc ccgacatgtc tgagctgaag aaaagccagg tgttctacaa gtactacctg   840
gacaaagagg aactgaacga caagaatatt aagtacgcct ctgccactt cgtggaaatc   900 gagatgtccc agctgctgaa aaactacgtg tacaagcggc tgagcaacat cagcaacgat   960
aagatcaagc ggatcttcga gtaccagaat ctgaaaaagc tgatcgaaaa caaactgctg  1020
aacaagctgg acacctacgt gcggaactgc ggcaagtaca ctactatct gcaagtgggc  1080 gagatcgcca cctccgactt tatcgcccgg aaccggcaga cgaggcctt cctgagaaac  1140 atcatcggcg tgtccagcgt ggcctacttc agcctgagga catcctgga aaccgagaac  1200 gagaacgata tcaccggccg gatgcggggc aagaccgtga gaacaacaa gggcgaagag  1260 aaatacgtgt ccggcgaggt ggacaagatc tacaatgaga acaagcagaa cgaagtgaaa  1320
gaaaatctga gatgttcta cagctacgac ttcaacatgg acaacaagaa cgagatcgag  1380
gacttcttcg ccaacatcga cgaggccatc agcagcatca gacacggcat cgtgcacttc  1440
aacctggaac tggaaggcaa ggacatcttc gccttcaaga atatcgcccc cagcgagatc  1500
tccaagaaga tgtttcagaa cgaaatcaac gaaaagaagc tgaagctgaa aatcttcaag  1560
cagctgaaca gcgccaacgt gttcaactac tacgagaagg atgtgatcat caagtacctg  1620
aagaatacca agttcaactt cgtgaacaaa acatcccct tcgtgcccag cttcaccaag  1680
ctgtacaaca agattgagga cctgcggaat accctgaagt ttttttggag cgtgcccaag  1740
gacaaagaag agaaggacgc ccagatctac ctgctgaaga atatctacta cggcgagttc  1800
ctgaacaagt tcgtgaaaaa ctccaaggtg ttctttaaga tcaccaatga agtgatcaag  1860
```

```
attaacaagc agcggaacca gaaaaccggc cactacaagt atcagaagtt cgagaacatc    1920
gagaaaaccg tgcccgtgga atacctggcc atcatccaga gcagagagat gatcaacaac    1980
caggacaaag aggaaaagaa tacctacatc gactttattc agcagatttt cctgaagggc    2040
ttcatcgact acctgaacaa gaacaatctg aagtatatcg agagcaacaa caacaatgac    2100
aacaacgaca tcttctccaa gatcaagatc aaaaaggata caaagagaa gtacgacaag    2160 atcctgaaga actatgagaa gcacaatcgg aacaagaaa tccctcacga gatcaatgag    2220
ttcgtgcgcg agatcaagct ggggaagatt ctgaagtaca ccgagaatct gaacatgttt    2280
tacctgatcc tgaagctgct gaaccacaaa gagctgacca acctgaaggg cagcctggaa    2340
aagtaccagt ccgccaacaa gaagaaaacc ttcagcgacg agctggaact gatcaacctg    2400
ctgaacctgg acaacaacag agtgaccgag gacttcgagc tggaagccaa cgagatcggc    2460
aagttcctgg acttcaacga aaacaaaatc aaggaccgga agagctgaa aaagttcgac    2520 accaacaaga tctatttcga cggcgagaac atcatcaagc accgggcctt ctacaatatc    2580
aagaaatacg gcatgctgaa tctgctggaa aagatcgccg ataaggccaa gtataagatc    2640
agcctgaaag aactgaaaga gtacagcaac aagaagaatg agattgaaaa gaactacacc    2700
atgcagcaga acctgcaccg gaagtacgcc agacccaaga aggacgaaaa gttcaacgac    2760
gaggactaca agagtatgaa gaaggccatc ggcaacatcc agaagtacac ccacctgaag    2820
aacaaggtgg aattcaatga gctgaacctg ctgcagggcc tgctgctgaa gatcctgcac    2880
cggctcgtgg gctacaccag catctgggag cgggacctga gattccggct gaagggcgag    2940
tttcccgaga ccactacat cgaggaaatt ttcaatttcg acaactccaa gaatgtgaag    3000
tacaaaagcg gccagatcgt ggaaaagtat atcaacttct acaagaact gtacaaggac    3060 aatgtggaaa gcggagcat ctactccgac aagaaagtga agaaactgaa gcaggaaaaa    3120
aaggacctgt acatccggaa ctacattgcc cacttcaact acatccccca cgccgagatt    3180
agcctgctgg aagtgctgga aaacctgcgg aagctgctgt cctacgaccg gaagctgaag    3240
aacgccatca tgaagtccat cgtggacatt ctgaaagaat acggcttcgt ggccaccttc    3300
aagatcggcg ctgacaagaa gatcgaaatc cagaccctgg aatcagagaa gatcgtgcac    3360
ctgaagaatc tgaagaaaaa gaaactgatg accgaccgga cagcgagga actgtgcgaa    3420 ctcgtgaaag tcatgttcga gtacaaggcc ctggaataa                         3459
```

<210> SEQ ID NO 24
<211> LENGTH: 1152
<212> TYPE: PRT
<213> ORGANISM: Artificial Sequence
<220> FEATURE:
<223> OTHER INFORMATION: C2C2 amino acids sequences, Leptotrichia
      wadei's Cas13a

<400> SEQUENCE: 24

```
Met Lys Val Thr Lys Val Asp Gly Ile Ser His Lys Lys Tyr Ile Glu
1               5                   10                  15

Glu Gly Lys Leu Val Lys Ser Thr Ser Glu Glu Asn Arg Thr Ser Glu
            20                  25                  30

Arg Leu Ser Glu Leu Leu Ser Ile Arg Leu Asp Ile Tyr Ile Lys Asn
        35                  40                  45

Pro Asp Asn Ala Ser Glu Glu Glu Asn Arg Ile Arg Arg Glu Asn Leu
    50                  55                  60

Lys Lys Phe Phe Ser Asn Lys Val Leu His Leu Lys Asp Ser Val Leu
```

```
                65                  70                  75                  80
Tyr Leu Lys Asn Arg Lys Glu Lys Asn Ala Val Gln Asp Lys Asn Tyr
                    85                  90                  95
Ser Glu Glu Asp Ile Ser Glu Tyr Asp Leu Lys Asn Lys Asn Ser Phe
                    100                 105                 110
Ser Val Leu Lys Lys Ile Leu Leu Asn Glu Asp Val Asn Ser Glu Glu
                    115                 120                 125
Leu Glu Ile Phe Arg Lys Asp Val Glu Ala Lys Leu Asn Lys Ile Asn
                    130                 135                 140
Ser Leu Lys Tyr Ser Phe Glu Glu Asn Lys Ala Asn Tyr Gln Lys Ile
145                 150                 155                 160
Asn Glu Asn Asn Val Glu Lys Val Gly Gly Lys Ser Lys Arg Asn Ile
                    165                 170                 175
Ile Tyr Asp Tyr Tyr Arg Glu Ser Ala Lys Arg Asn Tyr Ile Asn
                    180                 185                 190
Asn Val Gln Glu Ala Phe Asp Lys Leu Tyr Lys Lys Glu Asp Ile Glu
                    195                 200                 205
Lys Leu Phe Phe Leu Ile Glu Asn Ser Lys Lys His Glu Lys Tyr Lys
                    210                 215                 220
Ile Arg Glu Tyr Tyr His Lys Ile Ile Gly Arg Lys Asn Asp Lys Glu
225                 230                 235                 240
Asn Phe Ala Lys Ile Ile Tyr Glu Glu Ile Gln Asn Val Asn Asn Ile
                    245                 250                 255
Lys Glu Leu Ile Glu Lys Ile Pro Asp Met Ser Glu Leu Lys Lys Ser
                    260                 265                 270
Gln Val Phe Tyr Lys Tyr Leu Asp Lys Glu Glu Leu Asn Asp Lys
                    275                 280                 285
Asn Ile Lys Tyr Ala Phe Cys His Phe Val Glu Ile Glu Met Ser Gln
                    290                 295                 300
Leu Leu Lys Asn Tyr Val Tyr Lys Arg Leu Ser Asn Ile Ser Asn Asp
305                 310                 315                 320
Lys Ile Lys Arg Ile Phe Glu Tyr Gln Asn Leu Lys Lys Leu Ile Glu
                    325                 330                 335
Asn Lys Leu Leu Asn Lys Leu Asp Thr Tyr Val Arg Asn Cys Gly Lys
                    340                 345                 350
Tyr Asn Tyr Tyr Leu Gln Val Gly Glu Ile Ala Thr Ser Asp Phe Ile
                    355                 360                 365
Ala Arg Asn Arg Gln Asn Glu Ala Phe Leu Arg Asn Ile Ile Gly Val
                    370                 375                 380
Ser Ser Val Ala Tyr Phe Ser Leu Arg Asn Ile Leu Glu Thr Glu Asn
385                 390                 395                 400
Glu Asn Asp Ile Thr Gly Arg Met Arg Gly Lys Thr Val Lys Asn Asn
                    405                 410                 415
Lys Gly Glu Glu Lys Tyr Val Ser Gly Glu Val Asp Lys Ile Tyr Asn
                    420                 425                 430
Glu Asn Lys Gln Asn Glu Val Lys Glu Asn Leu Lys Met Phe Tyr Ser
                    435                 440                 445
Tyr Asp Phe Asn Met Asp Asn Lys Asn Glu Ile Glu Asp Phe Phe Ala
                    450                 455                 460
Asn Ile Asp Glu Ala Ile Ser Ser Ile Arg His Gly Ile Val His Phe
465                 470                 475                 480
Asn Leu Glu Leu Glu Gly Lys Asp Ile Phe Ala Phe Lys Asn Ile Ala
                    485                 490                 495
```

```
Pro Ser Glu Ile Ser Lys Lys Met Phe Gln Asn Glu Ile Asn Glu Lys
            500                 505                 510
Lys Leu Lys Leu Lys Ile Phe Lys Gln Leu Asn Ser Ala Asn Val Phe
        515                 520                 525
Asn Tyr Tyr Glu Lys Asp Val Ile Ile Lys Tyr Leu Lys Asn Thr Lys
    530                 535                 540
Phe Asn Phe Val Asn Lys Asn Ile Pro Phe Val Pro Ser Phe Thr Lys
545                 550                 555                 560
Leu Tyr Asn Lys Ile Glu Asp Leu Arg Asn Thr Leu Lys Phe Phe Trp
            565                 570                 575
Ser Val Pro Lys Asp Lys Glu Glu Lys Asp Ala Gln Ile Tyr Leu Leu
        580                 585                 590
Lys Asn Ile Tyr Tyr Gly Glu Phe Leu Asn Lys Phe Val Lys Asn Ser
    595                 600                 605
Lys Val Phe Phe Lys Ile Thr Asn Glu Val Ile Lys Ile Asn Lys Gln
    610                 615                 620
Arg Asn Gln Lys Thr Gly His Tyr Lys Tyr Gln Lys Phe Glu Asn Ile
625                 630                 635                 640
Glu Lys Thr Val Pro Val Glu Tyr Leu Ala Ile Ile Gln Ser Arg Glu
            645                 650                 655
Met Ile Asn Asn Gln Asp Lys Glu Glu Lys Asn Thr Tyr Ile Asp Phe
        660                 665                 670
Ile Gln Gln Ile Phe Leu Lys Gly Phe Ile Asp Tyr Leu Asn Lys Asn
    675                 680                 685
Asn Leu Lys Tyr Ile Glu Ser Asn Asn Asn Asn Asp Asn Asn Asp Ile
    690                 695                 700
Phe Ser Lys Ile Lys Ile Lys Asp Asn Lys Glu Lys Tyr Asp Lys
705                 710                 715                 720
Ile Leu Lys Asn Tyr Glu Lys His Asn Arg Asn Lys Glu Ile Pro His
            725                 730                 735
Glu Ile Asn Glu Phe Val Arg Glu Ile Lys Leu Gly Lys Ile Leu Lys
        740                 745                 750
Tyr Thr Glu Asn Leu Asn Met Phe Tyr Leu Ile Leu Lys Leu Leu Asn
    755                 760                 765
His Lys Glu Leu Thr Asn Leu Lys Gly Ser Leu Glu Lys Tyr Gln Ser
    770                 775                 780
Ala Asn Lys Glu Glu Thr Phe Ser Asp Glu Leu Glu Leu Ile Asn Leu
785                 790                 795                 800
Leu Asn Leu Asp Asn Asn Arg Val Thr Glu Asp Phe Glu Leu Glu Ala
            805                 810                 815
Asn Glu Ile Gly Lys Phe Leu Asp Phe Asn Glu Asn Lys Ile Lys Asp
        820                 825                 830
Arg Lys Glu Leu Lys Lys Phe Asp Thr Asn Lys Ile Tyr Phe Asp Gly
    835                 840                 845
Glu Asn Ile Ile Lys His Arg Ala Phe Tyr Asn Ile Lys Lys Tyr Gly
    850                 855                 860
Met Leu Asn Leu Leu Glu Lys Ile Ala Asp Lys Ala Lys Tyr Lys Ile
865                 870                 875                 880
Ser Leu Lys Glu Leu Lys Glu Tyr Ser Asn Lys Lys Asn Glu Ile Glu
            885                 890                 895
Lys Asn Tyr Thr Met Gln Gln Asn Leu His Arg Lys Tyr Ala Arg Pro
        900                 905                 910
```

```
Lys Lys Asp Glu Lys Phe Asn Asp Glu Asp Tyr Lys Tyr Glu Lys
            915                 920                 925

Ala Ile Gly Asn Ile Gln Lys Tyr Thr His Leu Lys Asn Lys Val Glu
        930                 935                 940

Phe Asn Glu Leu Asn Leu Leu Gln Gly Leu Leu Leu Lys Ile Leu His
945                 950                 955                 960

Arg Leu Val Gly Tyr Thr Ser Ile Trp Glu Arg Asp Leu Arg Phe Arg
                965                 970                 975

Leu Lys Gly Glu Phe Pro Glu Asn His Tyr Ile Glu Glu Ile Phe Asn
            980                 985                 990

Phe Asp Asn Ser Lys Asn Val Lys Tyr Lys Ser Gly Gln Ile Val Glu
        995                 1000                1005

Lys Tyr Ile Asn Phe Tyr Lys Glu Leu Tyr Lys Asp Asn Val Glu Lys
        1010                1015                1020

Arg Ser Ile Tyr Ser Asp Lys Lys Val Lys Lys Leu Lys Gln Glu Lys
1025                1030                1035                1040

Lys Asp Leu Tyr Ile Arg Asn Tyr Ile Ala His Phe Asn Tyr Ile Pro
                1045                1050                1055

His Ala Glu Ile Ser Leu Leu Glu Val Leu Glu Asn Leu Arg Lys Leu
            1060                1065                1070

Leu Ser Tyr Asp Arg Lys Leu Lys Asn Ala Ile Met Lys Ser Ile Val
        1075                1080                1085

Asp Ile Leu Lys Glu Tyr Gly Phe Val Ala Thr Phe Lys Ile Gly Ala
        1090                1095                1100

Asp Lys Lys Ile Glu Ile Gln Thr Leu Glu Ser Glu Lys Ile Val His
1105                1110                1115                1120

Leu Lys Asn Leu Lys Lys Lys Leu Met Thr Asp Arg Asn Ser Glu
                1125                1130                1135

Glu Leu Cys Glu Leu Val Lys Val Met Phe Glu Tyr Lys Ala Leu Glu
            1140                1145                1150

<210> SEQ ID NO 25
<211> LENGTH: 43
<212> TYPE: DNA
<213> ORGANISM: Artificial Sequence
<220> FEATURE:
<223> OTHER INFORMATION: T7 promoter and DNA sequence for producing
      crRNA

<400> SEQUENCE: 25
aattctaata cgactcacta taggaatttc tactgttgta gat                        43

<210> SEQ ID NO 26
<211> LENGTH: 32
<212> TYPE: DNA
<213> ORGANISM: Artificial Sequence
<220> FEATURE:
<223> OTHER INFORMATION: DNA sequence of BRCA1 Exon 7 in normal cell

<400> SEQUENCE: 26
caaagtatgg gctacagaaa ccgtgccaaa ag                                    32

<210> SEQ ID NO 27
<211> LENGTH: 32
<212> TYPE: DNA
<213> ORGANISM: Artificial Sequence
<220> FEATURE:
<223> OTHER INFORMATION: DNA sequence of BRCA1 Exon 7 in cancer cell

<400> SEQUENCE: 27
```

-continued caaagtatgg gcttcagaaa ccgtgccaaa ag                              32

<210> SEQ ID NO 28
<211> LENGTH: 32
<212> TYPE: DNA
<213> ORGANISM: Artificial Sequence
<220> FEATURE:
<223> OTHER INFORMATION: DNA sequence of BRCA1 Exon 10 in  normal cell

<400> SEQUENCE: 28
tgggaaaacc tatcggaaga aggcaagcct cc                              32

<210> SEQ ID NO 29
<211> LENGTH: 32
<212> TYPE: DNA
<213> ORGANISM: Artificial Sequence
<220> FEATURE:
<223> OTHER INFORMATION: DNA sequence of BRCA1 Exon 10 in cancerl cell

<400> SEQUENCE: 29
tgggaaaacc tatcggtaga aggcaagcct cc                              32

<210> SEQ ID NO 30
<211> LENGTH: 30
<212> TYPE: DNA
<213> ORGANISM: Artificial Sequence
<220> FEATURE:
<223> OTHER INFORMATION: DNA sequence of BRCA1 Exon 11 in normal cell

<400> SEQUENCE: 30
ggggccaaga aattagagtc ctcagaagag                                 30

<210> SEQ ID NO 31
<211> LENGTH: 31
<212> TYPE: DNA
<213> ORGANISM: Artificial Sequence
<220> FEATURE:
<223> OTHER INFORMATION: DNA sequence of BRCA1 Exon 11 in cancer cell

<400> SEQUENCE: 31
ggggccaaga aaattagagt cctcagaaga g                               31

<210> SEQ ID NO 32
<211> LENGTH: 31
<212> TYPE: DNA
<213> ORGANISM: Artificial Sequence
<220> FEATURE:
<223> OTHER INFORMATION: DNA sequence of BRCA1 Exon 11 in normal cell

<400> SEQUENCE: 32
atgatgaaga aagaggaacg ggcttggaag a                               31

<210> SEQ ID NO 33
<211> LENGTH: 29
<212> TYPE: DNA
<213> ORGANISM: Artificial Sequence
<220> FEATURE:
<223> OTHER INFORMATION: DNA sequence of BRCA1 Exon 11 in cancer cell

<400> SEQUENCE: 33
atgatgaaga aaggaacggg cttggaaga                                  29

<210> SEQ ID NO 34
<211> LENGTH: 33
<212> TYPE: DNA

```
<213> ORGANISM: Artificial Sequence
<220> FEATURE:
<223> OTHER INFORMATION: DNA sequence of BRCA1 Exon 11 in normal cell

<400> SEQUENCE: 34
catctcaggt tgttctgag acacctgatg acc                                    33

<210> SEQ ID NO 35
<211> LENGTH: 32
<212> TYPE: DNA
<213> ORGANISM: Artificial Sequence
<220> FEATURE:
<223> OTHER INFORMATION: DNA sequence of BRCA1 Exon 11 in cancer cell

<400> SEQUENCE: 35
catctcaggt tgttctaga cacctgatga cc                                     32

<210> SEQ ID NO 36
<211> LENGTH: 33
<212> TYPE: DNA
<213> ORGANISM: Artificial Sequence
<220> FEATURE:
<223> OTHER INFORMATION: DNA sequence of BRCA1 Exon 15 in normal cell

<400> SEQUENCE: 36
atatacagga tatgcgaatt aagaagaaac aaa                                   33

<210> SEQ ID NO 37
<211> LENGTH: 33
<212> TYPE: DNA
<213> ORGANISM: Artificial Sequence
<220> FEATURE:
<223> OTHER INFORMATION: DNA sequence of BRCA1 Exon 15 in cancer cell

<400> SEQUENCE: 37
atatacagga tatgtgaatt aagaagaaac aaa                                   33

<210> SEQ ID NO 38
<211> LENGTH: 32
<212> TYPE: DNA
<213> ORGANISM: Artificial Sequence
<220> FEATURE:
<223> OTHER INFORMATION: DNA sequence of TP53 in normal cell

<400> SEQUENCE: 38
taggaggccg agctctgttg cttcgaactc ca                                    32

<210> SEQ ID NO 39
<211> LENGTH: 31
<212> TYPE: DNA
<213> ORGANISM: Artificial Sequence
<220> FEATURE:
<223> OTHER INFORMATION: DNA sequence of TP53 in cancer cell

<400> SEQUENCE: 39
taggaggccg agctctttgc ttcgaactcc a                                     31

<210> SEQ ID NO 40
<211> LENGTH: 31
<212> TYPE: DNA
<213> ORGANISM: Artificial Sequence
<220> FEATURE:
<223> OTHER INFORMATION: DNA sequence of MSH2 in normal cell

<400> SEQUENCE: 40
tgaggaggtt tcgacatggc ggtgcagccg a                                     31
```

<210> SEQ ID NO 41
<211> LENGTH: 31
<212> TYPE: DNA
<213> ORGANISM: Artificial Sequence
<220> FEATURE:
<223> OTHER INFORMATION: DNA sequence of MSH2 in cancer cell

<400> SEQUENCE: 41
tgaggaggtt tcgacctggc ggtgcagccg a                              31

<210> SEQ ID NO 42
<211> LENGTH: 32
<212> TYPE: DNA
<213> ORGANISM: Artificial Sequence
<220> FEATURE:
<223> OTHER INFORMATION: DNA sequence of EGFR in normal cell

<400> SEQUENCE: 42
aaaaagatca agtgctggg ctccggtgcg tt                              32

<210> SEQ ID NO 43
<211> LENGTH: 32
<212> TYPE: DNA
<213> ORGANISM: Artificial Sequence
<220> FEATURE:
<223> OTHER INFORMATION: DNA sequence of EGFR in cancer cell

<400> SEQUENCE: 43
aaaaagatca agtgctgag ctccggtgcg tt                              32

<210> SEQ ID NO 44
<211> LENGTH: 33
<212> TYPE: DNA
<213> ORGANISM: Artificial Sequence
<220> FEATURE:
<223> OTHER INFORMATION: DNA sequence of FGFR3 in normal cell

<400> SEQUENCE: 44
atcctctctc tgaaatcact gagcaggaga aag                            33

<210> SEQ ID NO 45
<211> LENGTH: 33
<212> TYPE: DNA
<213> ORGANISM: Artificial Sequence
<220> FEATURE:
<223> OTHER INFORMATION: DNA sequence of FGFR3 in cancer cell

<400> SEQUENCE: 45
atcctctctc tgaaatcact gcgcaggaga aag                            33

<210> SEQ ID NO 46
<211> LENGTH: 1442
<212> TYPE: PRT
<213> ORGANISM: Artificial Sequence
<220> FEATURE:
<223> OTHER INFORMATION: SpyCas9

<400> SEQUENCE: 46

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Glu Phe Glu Leu Arg Arg Gln Ala Cys Gly Arg Met Asp Lys
        35                  40                  45

-continued

```
Lys Tyr Ser Ile Gly Leu Asp Ile Gly Thr Asn Ser Val Gly Trp Ala
     50                  55                  60

Val Ile Thr Asp Glu Tyr Lys Val Pro Ser Lys Lys Phe Lys Val Leu
 65                  70                  75                  80

Gly Asn Thr Asp Arg His Ser Ile Lys Lys Asn Leu Ile Gly Ala Leu
                 85                  90                  95

Leu Phe Asp Ser Gly Glu Thr Ala Glu Ala Thr Arg Leu Lys Arg Thr
                100                 105                 110

Ala Arg Arg Arg Tyr Thr Arg Arg Lys Asn Arg Ile Cys Tyr Leu Gln
            115                 120                 125

Glu Ile Phe Ser Asn Glu Met Ala Lys Val Asp Asp Ser Phe Phe His
            130                 135                 140

Arg Leu Glu Glu Ser Phe Leu Val Glu Asp Lys Lys His Glu Arg
145                 150                 155                 160

His Pro Ile Phe Gly Asn Ile Val Asp Glu Val Ala Tyr His Glu Lys
                165                 170                 175

Tyr Pro Thr Ile Tyr His Leu Arg Lys Lys Leu Val Asp Ser Thr Asp
                180                 185                 190

Lys Ala Asp Leu Arg Leu Ile Tyr Leu Ala Leu Ala His Met Ile Lys
            195                 200                 205

Phe Arg Gly His Phe Leu Ile Glu Gly Asp Leu Asn Pro Asp Asn Ser
210                 215                 220

Asp Val Asp Lys Leu Phe Ile Gln Leu Val Gln Thr Tyr Asn Gln Leu
225                 230                 235                 240

Phe Glu Glu Asn Pro Ile Asn Ala Ser Gly Val Asp Ala Lys Ala Ile
                245                 250                 255

Leu Ser Ala Arg Leu Ser Lys Ser Arg Arg Leu Glu Asn Leu Ile Ala
            260                 265                 270

Gln Leu Pro Gly Glu Lys Lys Asn Gly Leu Phe Gly Asn Leu Ile Ala
            275                 280                 285

Leu Ser Leu Gly Leu Thr Pro Asn Phe Lys Ser Asn Phe Asp Leu Ala
290                 295                 300

Glu Asp Ala Lys Leu Gln Leu Ser Lys Asp Thr Tyr Asp Asp Asp Leu
305                 310                 315                 320

Asp Asn Leu Leu Ala Gln Ile Gly Asp Gln Tyr Ala Asp Leu Phe Leu
                325                 330                 335

Ala Ala Lys Asn Leu Ser Asp Ala Ile Leu Leu Ser Asp Ile Leu Arg
            340                 345                 350

Val Asn Thr Glu Ile Thr Lys Ala Pro Leu Ser Ala Ser Met Ile Lys
            355                 360                 365

Arg Tyr Asp Glu His His Gln Asp Leu Thr Leu Leu Lys Ala Leu Val
370                 375                 380

Arg Gln Gln Leu Pro Glu Lys Tyr Lys Glu Ile Phe Phe Asp Gln Ser
385                 390                 395                 400

Lys Asn Gly Tyr Ala Gly Tyr Ile Asp Gly Gly Ala Ser Gln Glu Glu
                405                 410                 415

Phe Tyr Lys Phe Ile Lys Pro Ile Leu Glu Lys Met Asp Gly Thr Glu
            420                 425                 430

Glu Leu Leu Val Lys Leu Asn Arg Glu Asp Leu Leu Arg Lys Gln Arg
            435                 440                 445

Thr Phe Asp Asn Gly Ser Ile Pro His Gln Ile His Leu Gly Glu Leu
450                 455                 460
```

His Ala Ile Leu Arg Arg Gln Glu Asp Phe Tyr Pro Phe Leu Lys Asp
465                 470                 475                 480

Asn Arg Glu Lys Ile Glu Lys Ile Leu Thr Phe Arg Ile Pro Tyr Tyr
            485                 490                 495

Val Gly Pro Leu Ala Arg Gly Asn Ser Arg Phe Ala Trp Met Thr Arg
            500                 505                 510

Lys Ser Glu Glu Thr Ile Thr Pro Trp Asn Phe Glu Glu Val Val Asp
            515                 520                 525

Lys Gly Ala Ser Ala Gln Ser Phe Ile Glu Arg Met Thr Asn Phe Asp
            530                 535                 540

Lys Asn Leu Pro Asn Glu Lys Val Leu Pro Lys His Ser Leu Leu Tyr
545                 550                 555                 560

Glu Tyr Phe Thr Val Tyr Asn Glu Leu Thr Lys Val Lys Tyr Val Thr
            565                 570                 575

Glu Gly Met Arg Lys Pro Ala Phe Leu Ser Gly Glu Gln Lys Lys Ala
            580                 585                 590

Ile Val Asp Leu Leu Phe Lys Thr Asn Arg Lys Val Thr Val Lys Gln
            595                 600                 605

Leu Lys Glu Asp Tyr Phe Lys Lys Ile Glu Cys Phe Asp Ser Val Glu
            610                 615                 620

Ile Ser Gly Val Glu Asp Arg Phe Asn Ala Ser Leu Gly Thr Tyr His
625                 630                 635                 640

Asp Leu Leu Lys Ile Ile Lys Asp Lys Asp Phe Leu Asp Asn Glu Glu
            645                 650                 655

Asn Glu Asp Ile Leu Glu Asp Ile Val Leu Thr Leu Thr Leu Phe Glu
            660                 665                 670

Asp Arg Glu Met Ile Glu Glu Arg Leu Lys Thr Tyr Ala His Leu Phe
            675                 680                 685

Asp Asp Lys Val Met Lys Gln Leu Lys Arg Arg Arg Tyr Thr Gly Trp
            690                 695                 700

Gly Arg Leu Ser Arg Lys Leu Ile Asn Gly Ile Arg Asp Lys Gln Ser
705                 710                 715                 720

Gly Lys Thr Ile Leu Asp Phe Leu Lys Ser Asp Gly Phe Ala Asn Arg
            725                 730                 735

Asn Phe Met Gln Leu Ile His Asp Asp Ser Leu Thr Phe Lys Glu Asp
            740                 745                 750

Ile Gln Lys Ala Gln Val Ser Gly Gln Gly Asp Ser Leu His Glu His
            755                 760                 765

Ile Ala Asn Leu Ala Gly Ser Pro Ala Ile Lys Lys Gly Ile Leu Gln
770                 775                 780

Thr Val Lys Val Val Asp Glu Leu Val Lys Val Met Gly Arg His Lys
785                 790                 795                 800

Pro Glu Asn Ile Val Ile Glu Met Ala Arg Glu Asn Gln Thr Thr Gln
            805                 810                 815

Lys Gly Gln Lys Asn Ser Arg Glu Arg Met Lys Arg Ile Glu Glu Gly
            820                 825                 830

Ile Lys Glu Leu Gly Ser Gln Ile Leu Lys Glu His Pro Val Glu Asn
            835                 840                 845

Thr Gln Leu Gln Asn Glu Lys Leu Tyr Leu Tyr Leu Gln Asn Gly
            850                 855                 860

Arg Asp Met Tyr Val Asp Gln Glu Leu Asp Ile Asn Arg Leu Ser Asp
865                 870                 875                 880

Tyr Asp Val Asp His Ile Val Pro Gln Ser Phe Leu Lys Asp Asp Ser

-continued

```
            885                 890                 895

Ile Asp Asn Lys Val Leu Thr Arg Ser Asp Lys Asn Arg Gly Lys Ser
            900                 905                 910

Asp Asn Val Pro Ser Glu Glu Val Val Lys Lys Met Lys Asn Tyr Trp
            915                 920                 925

Arg Gln Leu Leu Asn Ala Lys Leu Ile Thr Gln Arg Lys Phe Asp Asn
            930                 935                 940

Leu Thr Lys Ala Glu Arg Gly Gly Leu Ser Glu Leu Asp Lys Ala Gly
945                 950                 955                 960

Phe Ile Lys Arg Gln Leu Val Glu Thr Arg Gln Ile Thr Lys His Val
                965                 970                 975

Ala Gln Ile Leu Asp Ser Arg Met Asn Thr Lys Tyr Asp Glu Asn Asp
            980                 985                 990

Lys Leu Ile Arg Glu Val Lys Val Ile Thr Leu Lys Ser Lys Leu Val
            995                 1000                1005

Ser Asp Phe Arg Lys Asp Phe Gln Phe Tyr Lys Val Arg Glu Ile Asn
        1010                1015                1020

Asn Tyr His His Ala His Asp Ala Tyr Leu Asn Ala Val Val Gly Thr
1025                1030                1035                1040

Ala Leu Ile Lys Lys Tyr Pro Lys Leu Glu Ser Glu Phe Val Tyr Gly
                1045                1050                1055

Asp Tyr Lys Val Tyr Asp Val Arg Lys Met Ile Ala Lys Ser Glu Gln
            1060                1065                1070

Glu Ile Gly Lys Ala Thr Ala Lys Tyr Phe Phe Tyr Ser Asn Ile Met
            1075                1080                1085

Asn Phe Phe Lys Thr Glu Ile Thr Leu Ala Asn Gly Glu Ile Arg Lys
        1090                1095                1100

Arg Pro Leu Ile Glu Thr Asn Gly Glu Thr Gly Glu Ile Val Trp Asp
1105                1110                1115                1120

Lys Gly Arg Asp Phe Ala Thr Val Arg Lys Val Leu Ser Met Pro Gln
                1125                1130                1135

Val Asn Ile Val Lys Lys Thr Glu Val Gln Thr Gly Gly Phe Ser Lys
            1140                1145                1150

Glu Ser Ile Leu Pro Lys Arg Asn Ser Asp Lys Leu Ile Ala Arg Lys
        1155                1160                1165

Lys Asp Trp Asp Pro Lys Lys Tyr Gly Gly Phe Asp Ser Pro Thr Val
        1170                1175                1180

Ala Tyr Ser Val Leu Val Val Ala Lys Val Glu Lys Gly Lys Ser Lys
1185                1190                1195                1200

Lys Leu Lys Ser Val Lys Glu Leu Leu Gly Ile Thr Ile Met Glu Arg
                1205                1210                1215

Ser Ser Phe Glu Lys Asn Pro Ile Asp Phe Leu Glu Ala Lys Gly Tyr
        1220                1225                1230

Lys Glu Val Lys Lys Asp Leu Ile Ile Lys Leu Pro Lys Tyr Ser Leu
            1235                1240                1245

Phe Glu Leu Glu Asn Gly Arg Lys Arg Met Leu Ala Ser Ala Gly Glu
        1250                1255                1260

Leu Gln Lys Gly Asn Glu Leu Ala Leu Pro Ser Lys Tyr Val Asn Phe
1265                1270                1275                1280

Leu Tyr Leu Ala Ser His Tyr Glu Lys Leu Lys Gly Ser Pro Glu Asp
                1285                1290                1295

Asn Glu Gln Lys Gln Leu Phe Val Glu Gln His Lys His Tyr Leu Asp
            1300                1305                1310
```

-continued

```
Glu Ile Ile Glu Gln Ile Ser Glu Phe Ser Lys Arg Val Ile Leu Ala
        1315                1320                1325
Asp Ala Asn Leu Asp Lys Val Leu Ser Ala Tyr Asn Lys His Arg Asp
    1330                1335                1340
Lys Pro Ile Arg Glu Gln Ala Glu Asn Ile Ile His Leu Phe Thr Leu
1345                1350                1355                1360
Thr Asn Leu Gly Ala Pro Ala Ala Phe Lys Tyr Phe Asp Thr Thr Ile
                1365                1370                1375
Asp Arg Lys Arg Tyr Thr Ser Thr Lys Glu Val Leu Asp Ala Thr Leu
            1380                1385                1390
Ile His Gln Ser Ile Thr Gly Leu Tyr Glu Thr Arg Ile Asp Leu Ser
        1395                1400                1405
Gln Leu Gly Gly Asp Ala Ala Ala Leu Asp Leu Glu Lys Arg Pro Ala
    1410                1415                1420
Ala Thr Lys Lys Ala Gly Gln Ala Lys Lys Lys Glu His His His His
1425                1430                1435                1440
His His

<210> SEQ ID NO 47
<211> LENGTH: 20
<212> TYPE: DNA
<213> ORGANISM: Artificial Sequence
<220> FEATURE:
<223> OTHER INFORMATION: HCC827 EGFR Target Sequence

<400> SEQUENCE: 47
cggagatgtc ttgatagcga                                              20

<210> SEQ ID NO 48
<211> LENGTH: 20
<212> TYPE: DNA
<213> ORGANISM: Artificial Sequence
<220> FEATURE:
<223> OTHER INFORMATION: HCC827 VSTM2A Target Sequence

<400> SEQUENCE: 48
agcttcctag caagtaacag                                              20

<210> SEQ ID NO 49
<211> LENGTH: 20
<212> TYPE: DNA
<213> ORGANISM: Artificial Sequence
<220> FEATURE:
<223> OTHER INFORMATION: HCC827 KIF5A Target Sequence

<400> SEQUENCE: 49
gcgcatcttc cctttgttat                                              20

<210> SEQ ID NO 50
<211> LENGTH: 20
<212> TYPE: DNA
<213> ORGANISM: Artificial Sequence
<220> FEATURE:
<223> OTHER INFORMATION: H1563 IRX1 Target Sequence

<400> SEQUENCE: 50
gtccggaaga ggaactagaa                                              20

<210> SEQ ID NO 51
<211> LENGTH: 20
<212> TYPE: DNA
```

```
<213> ORGANISM: Artificial Sequence
<220> FEATURE:
<223> OTHER INFORMATION: H1563 ADAMTS16 Target Sequence

<400> SEQUENCE: 51
ctccgtgccg ctggtttatt                                               20

<210> SEQ ID NO 52
<211> LENGTH: 20
<212> TYPE: DNA
<213> ORGANISM: Artificial Sequence
<220> FEATURE:
<223> OTHER INFORMATION: H1299 GNPDA2 Target Sequence

<400> SEQUENCE: 52
cagaagctct gcattcatcc                                               20

<210> SEQ ID NO 53
<211> LENGTH: 20
<212> TYPE: DNA
<213> ORGANISM: Artificial Sequence
<220> FEATURE:
<223> OTHER INFORMATION: H1299 KCNE2 Target Sequence

<400> SEQUENCE: 53
ggtgatgtga gttctagtcc                                               20

<210> SEQ ID NO 54
<211> LENGTH: 20
<212> TYPE: DNA
<213> ORGANISM: Artificial Sequence
<220> FEATURE:
<223> OTHER INFORMATION: H1299 SLC15A5 Target Sequence

<400> SEQUENCE: 54
ggaccgattg tgagaaatgc                                               20

<210> SEQ ID NO 55
<211> LENGTH: 20
<212> TYPE: DNA
<213> ORGANISM: Artificial Sequence
<220> FEATURE:
<223> OTHER INFORMATION: H1299 SMIM11 Target Sequence

<400> SEQUENCE: 55
gtgcccagtg tgatgatatt                                               20

<210> SEQ ID NO 56
<211> LENGTH: 20
<212> TYPE: DNA
<213> ORGANISM: Artificial Sequence
<220> FEATURE:
<223> OTHER INFORMATION: A549 DACH2 Target Sequence

<400> SEQUENCE: 56
gcatggcttt tggctgttcg                                               20

<210> SEQ ID NO 57
<211> LENGTH: 20
<212> TYPE: DNA
<213> ORGANISM: Artificial Sequence
<220> FEATURE:
<223> OTHER INFORMATION: A549 HERC2P2 Target Sequence

<400> SEQUENCE: 57
gctgtgattt caacaggacg                                               20
```

<210> SEQ ID NO 58
<211> LENGTH: 20
<212> TYPE: DNA
<213> ORGANISM: Artificial Sequence
<220> FEATURE:
<223> OTHER INFORMATION: A549 CD68 Target Sequence

<400> SEQUENCE: 58
agaccattgg agactacacg                                                    20

<210> SEQ ID NO 59
<211> LENGTH: 20
<212> TYPE: DNA
<213> ORGANISM: Artificial Sequence
<220> FEATURE:
<223> OTHER INFORMATION: A549 SHBG Target Sequence

<400> SEQUENCE: 59
atagtactag gctgcctcac                                                    20

<210> SEQ ID NO 60
<211> LENGTH: 20
<212> TYPE: DNA
<213> ORGANISM: Artificial Sequence
<220> FEATURE:
<223> OTHER INFORMATION: SKBR3 ERBB2 Target Sequence (chr17:37,863,
      321(+))

<400> SEQUENCE: 60
catgctccgc cacctctacc                                                    20

<210> SEQ ID NO 61
<211> LENGTH: 20
<212> TYPE: DNA
<213> ORGANISM: Artificial Sequence
<220> FEATURE:
<223> OTHER INFORMATION: SKBR3 ERBB2 Target Sequence (chr17:37,864,
      786(+))

<400> SEQUENCE: 61
ctgcagcttc gaagcctcac                                                    20

<210> SEQ ID NO 62
<211> LENGTH: 20
<212> TYPE: DNA
<213> ORGANISM: Artificial Sequence
<220> FEATURE:
<223> OTHER INFORMATION: SKBR3 ERBB2 Target Sequence (chr17:37,863,
      519(+))

<400> SEQUENCE: 62
cttgttgtgg tttctcaacc                                                    20

<210> SEQ ID NO 63
<211> LENGTH: 20
<212> TYPE: DNA
<213> ORGANISM: Artificial Sequence
<220> FEATURE:
<223> OTHER INFORMATION: SKBR3 ERBB2 Target Sequence (chr17:37,864,
      935(+))

<400> SEQUENCE: 63
ggaagacgcc ctcagaagat                                                    20

<210> SEQ ID NO 64

```
<211> LENGTH: 20
<212> TYPE: DNA
<213> ORGANISM: Artificial Sequence
<220> FEATURE:
<223> OTHER INFORMATION: SKBR3 ERBB2 Target Sequence (chr17:37,846,
      501(+))

<400> SEQUENCE: 64
gcctgtaatc ccagctactc                                                  20

<210> SEQ ID NO 65
<211> LENGTH: 20
<212> TYPE: DNA
<213> ORGANISM: Artificial Sequence
<220> FEATURE:
<223> OTHER INFORMATION: SKBR3 ERBB2 Target Sequence (chr17:37,880,
      586(+))

<400> SEQUENCE: 65
caggctagag tgaaatggtg                                                  20

<210> SEQ ID NO 66
<211> LENGTH: 20
<212> TYPE: DNA
<213> ORGANISM: Artificial Sequence
<220> FEATURE:
<223> OTHER INFORMATION: SKBR3 ERBB2 Target Sequence (locus N/A_1)

<400> SEQUENCE: 66
cttccttgta ccaacacgta                                                  20

<210> SEQ ID NO 67
<211> LENGTH: 20
<212> TYPE: DNA
<213> ORGANISM: Artificial Sequence
<220> FEATURE:
<223> OTHER INFORMATION: SKBR3 ERBB2 Target Sequence (locus N/A_2)

<400> SEQUENCE: 67
caggtgtgta ccaacacgta                                                  20

<210> SEQ ID NO 68
<211> LENGTH: 20
<212> TYPE: DNA
<213> ORGANISM: Artificial Sequence
<220> FEATURE:
<223> OTHER INFORMATION: SKBR3 KRT16 Target Sequence (chr17:39,766,
      652(-))

<400> SEQUENCE: 68
ccaggagtac cagctgccat                                                  20

<210> SEQ ID NO 69
<211> LENGTH: 20
<212> TYPE: DNA
<213> ORGANISM: Artificial Sequence
<220> FEATURE:
<223> OTHER INFORMATION: SKBR3 KRT16 Target Sequence (chr17:39,766,
      661(+))

<400> SEQUENCE: 69
tcttcacatc atgcagcagc                                                  20

<210> SEQ ID NO 70
<211> LENGTH: 20
<212> TYPE: DNA
<213> ORGANISM: Artificial Sequence
```

```
<220> FEATURE:
<223> OTHER INFORMATION: HT29 LINC00536 Target Sequence (chr8:117,336,
      549(+))

<400> SEQUENCE: 70
agtggccagg attgattcag                                                   20

<210> SEQ ID NO 71
<211> LENGTH: 20
<212> TYPE: DNA
<213> ORGANISM: Artificial Sequence
<220> FEATURE:
<223> OTHER INFORMATION: HT29 TRPS1 Target Sequence (chr8:116,630,
      763(-))

<400> SEQUENCE: 71
gacagcagaa tgaccttggt                                                   20

<210> SEQ ID NO 72
<211> LENGTH: 20
<212> TYPE: DNA
<213> ORGANISM: Artificial Sequence
<220> FEATURE:
<223> OTHER INFORMATION: HT29 CDK8 Target Sequence

<400> SEQUENCE: 72
cctgtcttgt tcccagtcat                                                   20

<210> SEQ ID NO 73
<211> LENGTH: 20
<212> TYPE: DNA
<213> ORGANISM: Artificial Sequence
<220> FEATURE:
<223> OTHER INFORMATION: HT29 TRAPPC9 Target Sequence

<400> SEQUENCE: 73
gtaagcttac ctagagaccc                                                   20

<210> SEQ ID NO 74
<211> LENGTH: 20
<212> TYPE: DNA
<213> ORGANISM: Artificial Sequence
<220> FEATURE:
<223> OTHER INFORMATION: HT29 HERC2P2 Target Sequence

<400> SEQUENCE: 74
gctgtgattt caacaggacg                                                   20

<210> SEQ ID NO 75
<211> LENGTH: 20
<212> TYPE: DNA
<213> ORGANISM: Artificial Sequence
<220> FEATURE:
<223> OTHER INFORMATION: HeLa PRDM9 Target Sequence

<400> SEQUENCE: 75
ggaccctatc tgaatgtgca                                                   20

<210> SEQ ID NO 76
<211> LENGTH: 20
<212> TYPE: DNA
<213> ORGANISM: Artificial Sequence
<220> FEATURE:
<223> OTHER INFORMATION: HeLa CDKN2B Target Sequence

<400> SEQUENCE: 76
```

```
gtgcattcca cgcgtaaaac                                               20

<210> SEQ ID NO 77
<211> LENGTH: 20
<212> TYPE: DNA
<213> ORGANISM: Artificial Sequence
<220> FEATURE:
<223> OTHER INFORMATION: HeLa HPV Target Sequence (locus: N/A_1)

<400> SEQUENCE: 77
tgcttattgc caccacctgc                                               20

<210> SEQ ID NO 78
<211> LENGTH: 20
<212> TYPE: DNA
<213> ORGANISM: Artificial Sequence
<220> FEATURE:
<223> OTHER INFORMATION: HeLa HPV Target Sequence (locus: N/A_2)

<400> SEQUENCE: 78
cctgcaggaa ccctaaaata                                               20

<210> SEQ ID NO 79
<211> LENGTH: 20
<212> TYPE: DNA
<213> ORGANISM: Artificial Sequence
<220> FEATURE:
<223> OTHER INFORMATION: HeLa HPV Target Sequence (locus: N/A_3)

<400> SEQUENCE: 79
ccatatttta gggttcctgc                                               20

<210> SEQ ID NO 80
<211> LENGTH: 20
<212> TYPE: DNA
<213> ORGANISM: Artificial Sequence
<220> FEATURE:
<223> OTHER INFORMATION: HeLa HPV Target Sequence (locus: N/A_4)

<400> SEQUENCE: 80
tgcaggtggt ggcaataagc                                               20

<210> SEQ ID NO 81
<211> LENGTH: 20
<212> TYPE: DNA
<213> ORGANISM: Artificial Sequence
<220> FEATURE:
<223> OTHER INFORMATION: LINE2(mt2) Target Sequence

<400> SEQUENCE: 81
aatctccccc acccttaaga                                               20

<210> SEQ ID NO 82
<211> LENGTH: 20
<212> TYPE: DNA
<213> ORGANISM: Artificial Sequence
<220> FEATURE:
<223> OTHER INFORMATION: CCR5 Target Sequence

<400> SEQUENCE: 82
tgacatcaat tattatacat                                               20

<210> SEQ ID NO 83
<211> LENGTH: 20
<212> TYPE: DNA
<213> ORGANISM: Artificial Sequence
```

```
<220> FEATURE:
<223> OTHER INFORMATION: HPRT1 Target Sequence

<400> SEQUENCE: 83
gcatttctca gtcctaaaca                                                    20

<210> SEQ ID NO 84
<211> LENGTH: 20
<212> TYPE: DNA
<213> ORGANISM: Artificial Sequence
<220> FEATURE:
<223> OTHER INFORMATION: NT1 Target Sequence

<400> SEQUENCE: 84
gggtaaccgt gcggtcgtac                                                    20

<210> SEQ ID NO 85
<211> LENGTH: 10
<212> TYPE: DNA
<213> ORGANISM: Artificial Sequence
<220> FEATURE:
<223> OTHER INFORMATION: NT2 Target Sequence

<400> SEQUENCE: 85
gggtaaccgt                                                               10

<210> SEQ ID NO 86
<211> LENGTH: 5
<212> TYPE: DNA
<213> ORGANISM: Artificial Sequence
<220> FEATURE:
<223> OTHER INFORMATION: NT3 Target Sequence

<400> SEQUENCE: 86 gggta                                                                     5

<210> SEQ ID NO 87
<211> LENGTH: 1951
<212> TYPE: PRT
<213> ORGANISM: Artificial Sequence
<220> FEATURE:
<223> OTHER INFORMATION: Cas9-RecJ

<400> SEQUENCE: 87
```

Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

-continued

```
Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
            420                 425                 430

Lys Asp Asn Arg Glu Lys Ile Glu Lys Ile Leu Thr Phe Arg Ile Pro
        435                 440                 445

Tyr Tyr Val Gly Pro Leu Ala Arg Gly Asn Ser Arg Phe Ala Trp Met
    450                 455                 460

Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560
```

-continued

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
            595                 600                 605

Glu Glu Asn Glu Asp Ile Leu Glu Asp Ile Val Leu Thr Leu Thr Leu
        610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
        690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
            755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
        850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val

```
            980             985                 990
Gly Thr Ala Leu Ile Lys Lys Tyr Pro Lys Leu Glu Ser Glu Phe Val
            995             1000                1005

Tyr Gly Asp Tyr Lys Val Tyr Asp Val Arg Lys Met Ile Ala Lys Ser
            1010            1015                1020

Glu Gln Glu Ile Gly Lys Ala Thr Ala Lys Tyr Phe Phe Tyr Ser Asn
1025            1030            1035                1040

Ile Met Asn Phe Phe Lys Thr Glu Ile Thr Leu Ala Asn Gly Glu Ile
                1045            1050                1055

Arg Lys Arg Pro Leu Ile Glu Thr Asn Gly Glu Thr Gly Glu Ile Val
                1060            1065                1070

Trp Asp Lys Gly Arg Asp Phe Ala Thr Val Arg Lys Val Leu Ser Met
                1075            1080                1085

Pro Gln Val Asn Ile Val Lys Lys Thr Glu Val Gln Thr Gly Gly Phe
                1090            1095                1100

Ser Lys Glu Ser Ile Leu Pro Lys Arg Asn Ser Asp Lys Leu Ile Ala
1105            1110            1115                1120

Arg Lys Lys Asp Trp Asp Pro Lys Lys Tyr Gly Gly Phe Asp Ser Pro
                1125            1130                1135

Thr Val Ala Tyr Ser Val Leu Val Val Ala Lys Val Glu Lys Gly Lys
                1140            1145                1150

Ser Lys Lys Leu Lys Ser Val Lys Glu Leu Leu Gly Ile Thr Ile Met
                1155            1160                1165

Glu Arg Ser Ser Phe Glu Lys Asn Pro Ile Asp Phe Leu Glu Ala Lys
                1170            1175                1180

Gly Tyr Lys Glu Val Lys Lys Asp Leu Ile Ile Lys Leu Pro Lys Tyr
1185            1190            1195                1200

Ser Leu Phe Glu Leu Glu Asn Gly Arg Lys Arg Met Leu Ala Ser Ala
                1205            1210                1215

Gly Glu Leu Gln Lys Gly Asn Glu Leu Ala Leu Pro Ser Lys Tyr Val
                1220            1225                1230

Asn Phe Leu Tyr Leu Ala Ser His Tyr Glu Lys Leu Lys Gly Ser Pro
                1235            1240                1245

Glu Asp Asn Glu Gln Lys Gln Leu Phe Val Glu Gln His Lys His Tyr
                1250            1255                1260

Leu Asp Glu Ile Ile Glu Gln Ile Ser Glu Phe Ser Lys Arg Val Ile
1265            1270            1275                1280

Leu Ala Asp Ala Asn Leu Asp Lys Val Leu Ser Ala Tyr Asn Lys His
                1285            1290                1295

Arg Asp Lys Pro Ile Arg Glu Gln Ala Glu Asn Ile Ile His Leu Phe
                1300            1305                1310

Thr Leu Thr Asn Leu Gly Ala Pro Ala Ala Phe Lys Tyr Phe Asp Thr
                1315            1320                1325

Thr Ile Asp Arg Lys Arg Tyr Thr Ser Thr Lys Glu Val Leu Asp Ala
                1330            1335                1340

Thr Leu Ile His Gln Ser Ile Thr Gly Leu Tyr Glu Thr Arg Ile Asp
1345            1350            1355                1360

Leu Ser Gln Leu Gly Gly Asp Ala Ala Leu Asp Leu Gln Val Lys
                1365            1370                1375

Gln Gln Ile Gln Leu Arg Arg Arg Glu Val Asp Glu Thr Ala Asp Leu
                1380            1385                1390

Pro Ala Glu Leu Pro Pro Leu Leu Arg Arg Leu Tyr Ala Ser Arg Gly
                1395            1400                1405
```

```
Val Arg Ser Ala Gln Glu Leu Glu Arg Ser Val Lys Gly Met Leu Pro
    1410                1415                1420

Trp Gln Gln Leu Ser Gly Val Glu Lys Ala Val Glu Ile Leu Tyr Asn
1425                1430                1435                1440

Ala Phe Arg Glu Gly Thr Arg Ile Ile Val Val Gly Asp Phe Asp Ala
            1445                1450                1455

Asp Gly Ala Thr Ser Thr Ala Leu Ser Val Leu Ala Met Arg Ser Leu
            1460                1465                1470

Gly Cys Ser Asn Ile Asp Tyr Leu Val Pro Asn Arg Phe Glu Asp Gly
            1475                1480                1485

Tyr Gly Leu Ser Pro Glu Val Val Asp Gln Ala His Ala Arg Gly Ala
            1490                1495                1500

Gln Leu Ile Val Thr Val Asp Asn Gly Ile Ser Ser His Ala Gly Val
1505                1510                1515                1520

Glu His Ala Arg Ser Leu Gly Ile Pro Val Ile Val Thr Asp His His
                1525                1530                1535

Leu Pro Gly Glu Thr Leu Pro Ala Ala Glu Ala Ile Ile Asn Pro Asn
            1540                1545                1550

Leu Arg Asp Cys Asn Phe Pro Ser Lys Ser Leu Ala Gly Val Gly Val
            1555                1560                1565

Ala Phe Tyr Leu Met Leu Ala Leu Arg Thr Phe Leu Arg Asp Gln Gly
            1570                1575                1580

Trp Phe Asp Glu Arg Gly Ile Ala Ile Pro Asn Leu Ala Glu Leu Leu
1585                1590                1595                1600

Asp Leu Val Ala Leu Gly Thr Val Ala Asp Val Val Pro Leu Asp Ala
            1605                1610                1615

Asn Asn Arg Ile Leu Thr Trp Gln Gly Met Ser Arg Ile Arg Ala Gly
            1620                1625                1630

Lys Cys Arg Pro Gly Ile Lys Ala Leu Leu Glu Val Ala Asn Arg Asp
            1635                1640                1645

Ala Gln Lys Leu Ala Ala Ser Asp Leu Gly Phe Ala Leu Gly Pro Arg
            1650                1655                1660

Leu Asn Ala Ala Gly Arg Leu Asp Asp Met Ser Val Gly Val Ala Leu
1665                1670                1675                1680

Leu Leu Cys Asp Asn Ile Gly Glu Ala Arg Val Leu Ala Asn Glu Leu
            1685                1690                1695

Asp Ala Leu Asn Gln Thr Arg Lys Glu Ile Glu Gln Gly Met Gln Val
            1700                1705                1710

Glu Ala Leu Thr Leu Cys Glu Lys Leu Glu Arg Ser Arg Asp Thr Leu
            1715                1720                1725

Pro Gly Gly Leu Ala Met Tyr His Pro Glu Trp His Gln Gly Val Val
            1730                1735                1740

Gly Ile Leu Ala Ser Arg Ile Lys Glu Arg Phe His Arg Pro Val Ile
1745                1750                1755                1760

Ala Phe Ala Pro Ala Gly Asp Gly Thr Leu Lys Gly Ser Gly Arg Ser
            1765                1770                1775

Ile Gln Gly Leu His Met Arg Asp Ala Leu Glu Arg Leu Asp Thr Leu
            1780                1785                1790

Tyr Pro Gly Met Ile Leu Lys Phe Gly Gly His Ala Met Ala Ala Gly
            1795                1800                1805

Leu Ser Leu Glu Glu Asp Lys Phe Glu Leu Phe Gln Gln Arg Phe Gly
            1810                1815                1820
```

Glu Leu Val Thr Glu Trp Leu Asp Pro Ser Leu Leu Gln Gly Glu Val
1825                1830                1835                1840

Val Ser Asp Gly Pro Leu Ser Pro Ala Glu Met Thr Met Glu Val Ala
            1845                1850                1855

Gln Leu Leu Arg Asp Ala Gly Pro Trp Gly Gln Met Phe Pro Glu Pro
        1860                1865                1870

Leu Phe Asp Gly His Phe Arg Leu Leu Gln Gln Arg Leu Val Gly Glu
    1875                1880                1885

Arg His Leu Lys Val Met Val Glu Pro Val Gly Gly Pro Leu Leu
    1890                1895                1900

Asp Gly Ile Ala Phe Asn Val Asp Thr Ala Leu Trp Pro Asp Asn Gly
1905                1910                1915                1920

Val Arg Glu Val Gln Leu Ala Tyr Lys Leu Asp Ile Asn Glu Phe Arg
            1925                1930                1935

Gly Asn Arg Ser Leu Gln Ile Ile Ile Asp Asn Ile Trp Pro Ile
        1940                1945                1950

<210> SEQ ID NO 88
<211> LENGTH: 96
<212> TYPE: DNA
<213> ORGANISM: Artificial Sequence
<220> FEATURE:
<223> OTHER INFORMATION: EGFR gRNA Sequence

<400> SEQUENCE: 88
cggagatgtc ttgatagcga gttttagagc tagaaatagc aagttaaaat aaggctagtc    60
cgttatcaac ttgaaaaagt ggcaccgagt cggtgc    96

<210> SEQ ID NO 89
<211> LENGTH: 96
<212> TYPE: DNA
<213> ORGANISM: Artificial Sequence
<220> FEATURE:
<223> OTHER INFORMATION: VSTM2A gRNA Sequence

<400> SEQUENCE: 89
agcttcctag caagtaacag gttttagagc tagaaatagc aagttaaaat aaggctagtc    60
cgttatcaac ttgaaaaagt ggcaccgagt cggtgc    96

<210> SEQ ID NO 90
<211> LENGTH: 96
<212> TYPE: DNA
<213> ORGANISM: Artificial Sequence
<220> FEATURE:
<223> OTHER INFORMATION: KIF5A gRNA Sequence

<400> SEQUENCE: 90
gcgcatcttc cctttgttat gttttagagc tagaaatagc aagttaaaat aaggctagtc    60
cgttatcaac ttgaaaaagt ggcaccgagt cggtgc    96

<210> SEQ ID NO 91
<211> LENGTH: 96
<212> TYPE: DNA
<213> ORGANISM: Artificial Sequence
<220> FEATURE:
<223> OTHER INFORMATION: IRX1 gRNA Sequence

<400> SEQUENCE: 91
gtccggaaga ggaactagaa gttttagagc tagaaatagc aagttaaaat aaggctagtc    60
cgttatcaac ttgaaaaagt ggcaccgagt cggtgc    96

<210> SEQ ID NO 92
<211> LENGTH: 96
<212> TYPE: DNA
<213> ORGANISM: Artificial Sequence
<220> FEATURE:
<223> OTHER INFORMATION: ADAMTS16 gRNA Sequence

<400> SEQUENCE: 92
ctccgtgccg ctggtttatt gttttagagc tagaaatagc aagttaaaat aaggctagtc      60
cgttatcaac ttgaaaaagt ggcaccgagt cggtgc                                96

<210> SEQ ID NO 93
<211> LENGTH: 96
<212> TYPE: DNA
<213> ORGANISM: Artificial Sequence
<220> FEATURE:
<223> OTHER INFORMATION: GNPDA2 gRNA Sequence

<400> SEQUENCE: 93
cagaagctct gcattcatcc gttttagagc tagaaatagc aagttaaaat aaggctagtc      60
cgttatcaac ttgaaaaagt ggcaccgagt cggtgc                                96

<210> SEQ ID NO 94
<211> LENGTH: 96
<212> TYPE: DNA
<213> ORGANISM: Artificial Sequence
<220> FEATURE:
<223> OTHER INFORMATION: KCNE2 Target Sequence

<400> SEQUENCE: 94
ggtgatgtga gttctagtcc gttttagagc tagaaatagc aagttaaaat aaggctagtc      60
cgttatcaac ttgaaaaagt ggcaccgagt cggtgc                                96

<210> SEQ ID NO 95
<211> LENGTH: 96
<212> TYPE: DNA
<213> ORGANISM: Artificial Sequence
<220> FEATURE:
<223> OTHER INFORMATION: SLC15A5 gRNA Sequence

<400> SEQUENCE: 95
ggaccgattg tgagaaatgc gttttagagc tagaaatagc aagttaaaat aaggctagtc      60
cgttatcaac ttgaaaaagt ggcaccgagt cggtgc                                96

<210> SEQ ID NO 96
<211> LENGTH: 96
<212> TYPE: DNA
<213> ORGANISM: Artificial Sequence
<220> FEATURE:
<223> OTHER INFORMATION: SMIM11 gRNA Sequence

<400> SEQUENCE: 96
gtgcccagtg tgatgatatt gttttagagc tagaaatagc aagttaaaat aaggctagtc      60
cgttatcaac ttgaaaaagt ggcaccgagt cggtgc                                96

<210> SEQ ID NO 97
<211> LENGTH: 96
<212> TYPE: DNA
<213> ORGANISM: Artificial Sequence
<220> FEATURE:
<223> OTHER INFORMATION: DACH2 gRNA Sequence

<400> SEQUENCE: 97
gcatggcttt tggctgttcg gttttagagc tagaaatagc aagttaaaat aaggctagtc    60
cgttatcaac ttgaaaaagt ggcaccgagt cggtgc    96

<210> SEQ ID NO 98
<211> LENGTH: 96
<212> TYPE: DNA
<213> ORGANISM: Artificial Sequence
<220> FEATURE:
<223> OTHER INFORMATION: HERC2P2 gRNA Sequence

<400> SEQUENCE: 98
gctgtgattt caacaggacg gttttagagc tagaaatagc aagttaaaat aaggctagtc    60
cgttatcaac ttgaaaaagt ggcaccgagt cggtgc    96

<210> SEQ ID NO 99
<211> LENGTH: 96
<212> TYPE: DNA
<213> ORGANISM: Artificial Sequence
<220> FEATURE:
<223> OTHER INFORMATION: CD68 gRNA Sequence

<400> SEQUENCE: 99
agaccattgg agactacacg gttttagagc tagaaatagc aagttaaaat aaggctagtc    60
cgttatcaac ttgaaaaagt ggcaccgagt cggtgc    96

<210> SEQ ID NO 100
<211> LENGTH: 96
<212> TYPE: DNA
<213> ORGANISM: Artificial Sequence
<220> FEATURE:
<223> OTHER INFORMATION: SHBG gRNA Sequence

<400> SEQUENCE: 100
atagtactag gctgcctcac gttttagagc tagaaatagc aagttaaaat aaggctagtc    60
cgttatcaac ttgaaaaagt ggcaccgagt cggtgc    96

<210> SEQ ID NO 101
<211> LENGTH: 96
<212> TYPE: DNA
<213> ORGANISM: Artificial Sequence
<220> FEATURE:
<223> OTHER INFORMATION: ERBB2 (1) gRNA Sequence

<400> SEQUENCE: 101
catgctccgc cacctctacc gttttagagc tagaaatagc aagttaaaat aaggctagtc    60
cgttatcaac ttgaaaaagt ggcaccgagt cggtgc    96

<210> SEQ ID NO 102
<211> LENGTH: 96
<212> TYPE: DNA
<213> ORGANISM: Artificial Sequence
<220> FEATURE:
<223> OTHER INFORMATION: ERBB2 (2) gRNA Sequence

<400> SEQUENCE: 102
ctgcagcttc gaagcctcac gttttagagc tagaaatagc aagttaaaat aaggctagtc    60
cgttatcaac ttgaaaaagt ggcaccgagt cggtgc    96

<210> SEQ ID NO 103
<211> LENGTH: 96

```
<212> TYPE: DNA
<213> ORGANISM: Artificial Sequence
<220> FEATURE:
<223> OTHER INFORMATION: ERBB2 (3) gRNA Sequence

<400> SEQUENCE: 103
cttgttgtgg tttctcaacc gttttagagc tagaaatagc aagttaaaat aaggctagtc    60
cgttatcaac ttgaaaaagt ggcaccgagt cggtgc                              96

<210> SEQ ID NO 104
<211> LENGTH: 96
<212> TYPE: DNA
<213> ORGANISM: Artificial Sequence
<220> FEATURE:
<223> OTHER INFORMATION: ERBB2 (4) gRNA Sequence

<400> SEQUENCE: 104
ggaagacgcc ctcagaagat gttttagagc tagaaatagc aagttaaaat aaggctagtc    60
cgttatcaac ttgaaaaagt ggcaccgagt cggtgc                              96

<210> SEQ ID NO 105
<211> LENGTH: 96
<212> TYPE: DNA
<213> ORGANISM: Artificial Sequence
<220> FEATURE:
<223> OTHER INFORMATION: ERBB2 (5) gRNA Sequence

<400> SEQUENCE: 105
gcctgtaatc ccagctactc gttttagagc tagaaatagc aagttaaaat aaggctagtc    60
cgttatcaac ttgaaaaagt ggcaccgagt cggtgc                              96

<210> SEQ ID NO 106
<211> LENGTH: 96
<212> TYPE: DNA
<213> ORGANISM: Artificial Sequence
<220> FEATURE:
<223> OTHER INFORMATION: ERBB2 (6) gRNA Sequence

<400> SEQUENCE: 106
caggctagag tgaaatggtg gttttagagc tagaaatagc aagttaaaat aaggctagtc    60
cgttatcaac ttgaaaaagt ggcaccgagt cggtgc                              96

<210> SEQ ID NO 107
<211> LENGTH: 96
<212> TYPE: DNA
<213> ORGANISM: Artificial Sequence
<220> FEATURE:
<223> OTHER INFORMATION: ERBB2 (7) gRNA Sequence

<400> SEQUENCE: 107
cttccttgta ccaacacgta gttttagagc tagaaatagc aagttaaaat aaggctagtc    60
cgttatcaac ttgaaaaagt ggcaccgagt cggtgc                              96

<210> SEQ ID NO 108
<211> LENGTH: 96
<212> TYPE: DNA
<213> ORGANISM: Artificial Sequence
<220> FEATURE:
<223> OTHER INFORMATION: ERBB2 (8) gRNA Sequence

<400> SEQUENCE: 108
caggtgtgta ccaacacgta gttttagagc tagaaatagc aagttaaaat aaggctagtc    60
```

```
cgttatcaac ttgaaaaagt ggcaccgagt cggtgc                                   96

<210> SEQ ID NO 109
<211> LENGTH: 96
<212> TYPE: DNA
<213> ORGANISM: Artificial Sequence
<220> FEATURE:
<223> OTHER INFORMATION: KRT16 (1) gRNA Sequence

<400> SEQUENCE: 109
ccaggagtac cagctgccat gttttagagc tagaaatagc aagttaaaat aaggctagtc         60
cgttatcaac ttgaaaaagt ggcaccgagt cggtgc                                   96

<210> SEQ ID NO 110
<211> LENGTH: 96
<212> TYPE: DNA
<213> ORGANISM: Artificial Sequence
<220> FEATURE:
<223> OTHER INFORMATION: KRT16 (2) gRNA Sequence

<400> SEQUENCE: 110
tcttcacatc atgcagcagc gttttagagc tagaaatagc aagttaaaat aaggctagtc         60
cgttatcaac ttgaaaaagt ggcaccgagt cggtgc                                   96

<210> SEQ ID NO 111
<211> LENGTH: 96
<212> TYPE: DNA
<213> ORGANISM: Artificial Sequence
<220> FEATURE:
<223> OTHER INFORMATION: LINC00536 gRNA Sequence

<400> SEQUENCE: 111
agtggccagg attgattcag gttttagagc tagaaatagc aagttaaaat aaggctagtc         60
cgttatcaac ttgaaaaagt ggcaccgagt cggtgc                                   96

<210> SEQ ID NO 112
<211> LENGTH: 96
<212> TYPE: DNA
<213> ORGANISM: Artificial Sequence
<220> FEATURE:
<223> OTHER INFORMATION: TRPS1 gRNA Sequence

<400> SEQUENCE: 112
gacagcagaa tgaccttggt gttttagagc tagaaatagc aagttaaaat aaggctagtc         60
cgttatcaac ttgaaaaagt ggcaccgagt cggtgc                                   96

<210> SEQ ID NO 113
<211> LENGTH: 96
<212> TYPE: DNA
<213> ORGANISM: Artificial Sequence
<220> FEATURE:
<223> OTHER INFORMATION: CDK8 gRNA Sequence

<400> SEQUENCE: 113
cctgtcttgt tcccagtcat gttttagagc tagaaatagc aagttaaaat aaggctagtc         60
cgttatcaac ttgaaaaagt ggcaccgagt cggtgc                                   96

<210> SEQ ID NO 114
<211> LENGTH: 96
<212> TYPE: DNA
<213> ORGANISM: Artificial Sequence
<220> FEATURE:
<223> OTHER INFORMATION: TRAPPC9 gRNA Sequence
```

```
<400> SEQUENCE: 114
gtaagcttac ctagagaccc gttttagagc tagaaatagc aagttaaaat aaggctagtc    60
cgttatcaac ttgaaaaagt ggcaccgagt cggtgc                              96

<210> SEQ ID NO 115
<211> LENGTH: 96
<212> TYPE: DNA
<213> ORGANISM: Artificial Sequence
<220> FEATURE:
<223> OTHER INFORMATION: SIRPB1 gRNA Sequence

<400> SEQUENCE: 115
gacaccctaa cagggttatg gttttagagc tagaaatagc aagttaaaat aaggctagtc    60
cgttatcaac ttgaaaaagt ggcaccgagt cggtgc                              96

<210> SEQ ID NO 116
<211> LENGTH: 96
<212> TYPE: DNA
<213> ORGANISM: Artificial Sequence
<220> FEATURE:
<223> OTHER INFORMATION: MRC1 gRNA Sequence

<400> SEQUENCE: 116
ctcactgcag ccttgacatc gttttagagc tagaaatagc aagttaaaat aaggctagtc    60
cgttatcaac ttgaaaaagt ggcaccgagt cggtgc                              96

<210> SEQ ID NO 117
<211> LENGTH: 96
<212> TYPE: DNA
<213> ORGANISM: Artificial Sequence
<220> FEATURE:
<223> OTHER INFORMATION: ATP11A gRNA Sequence

<400> SEQUENCE: 117
cgtccaagtg tgtgagtgag gttttagagc tagaaatagc aagttaaaat aaggctagtc    60
cgttatcaac ttgaaaaagt ggcaccgagt cggtgc                              96

<210> SEQ ID NO 118
<211> LENGTH: 96
<212> TYPE: DNA
<213> ORGANISM: Artificial Sequence
<220> FEATURE:
<223> OTHER INFORMATION: POTEB gRNA Sequence

<400> SEQUENCE: 118
gtggaaacct cagagatgtc gttttagagc tagaaatagc aagttaaaat aaggctagtc    60
cgttatcaac ttgaaaaagt ggcaccgagt cggtgc                              96

<210> SEQ ID NO 119
<211> LENGTH: 96
<212> TYPE: DNA
<213> ORGANISM: Artificial Sequence
<220> FEATURE:
<223> OTHER INFORMATION: PRDM9 gRNA Sequence

<400> SEQUENCE: 119
ggaccctatc tgaatgtgca gttttagagc tagaaatagc aagttaaaat aaggctagtc    60
cgttatcaac ttgaaaaagt ggcaccgagt cggtgc                              96

<210> SEQ ID NO 120
```

```
<211> LENGTH: 96
<212> TYPE: DNA
<213> ORGANISM: Artificial Sequence
<220> FEATURE:
<223> OTHER INFORMATION: CDKN2B gRNA Sequence

<400> SEQUENCE: 120
gtgcattcca cgcgtaaaac gttttagagc tagaaatagc aagttaaaat aaggctagtc    60
cgttatcaac ttgaaaaagt ggcaccgagt cggtgc                              96

<210> SEQ ID NO 121
<211> LENGTH: 96
<212> TYPE: DNA
<213> ORGANISM: Artificial Sequence
<220> FEATURE:
<223> OTHER INFORMATION: HPV (1) gRNA Sequence

<400> SEQUENCE: 121
tgcttattgc caccacctgc gttttagagc tagaaatagc aagttaaaat aaggctagtc    60
cgttatcaac ttgaaaaagt ggcaccgagt cggtgc                              96

<210> SEQ ID NO 122
<211> LENGTH: 96
<212> TYPE: DNA
<213> ORGANISM: Artificial Sequence
<220> FEATURE:
<223> OTHER INFORMATION: HPV (2) gRNA Sequence

<400> SEQUENCE: 122
cctgcaggaa ccctaaaata gttttagagc tagaaatagc aagttaaaat aaggctagtc    60
cgttatcaac ttgaaaaagt ggcaccgagt cggtgc                              96

<210> SEQ ID NO 123
<211> LENGTH: 96
<212> TYPE: DNA
<213> ORGANISM: Artificial Sequence
<220> FEATURE:
<223> OTHER INFORMATION: HPV (3) gRNA Sequence

<400> SEQUENCE: 123
ccatatttta gggttcctgc gttttagagc tagaaatagc aagttaaaat aaggctagtc    60
cgttatcaac ttgaaaaagt ggcaccgagt cggtgc                              96

<210> SEQ ID NO 124
<211> LENGTH: 96
<212> TYPE: DNA
<213> ORGANISM: Artificial Sequence
<220> FEATURE:
<223> OTHER INFORMATION: HPV (4) gRNA Sequence

<400> SEQUENCE: 124
tgcaggtggt ggcaataagc gttttagagc tagaaatagc aagttaaaat aaggctagtc    60
cgttatcaac ttgaaaaagt ggcaccgagt cggtgc                              96

<210> SEQ ID NO 125
<211> LENGTH: 96
<212> TYPE: DNA
<213> ORGANISM: Artificial Sequence
<220> FEATURE:
<223> OTHER INFORMATION: LINE2 (mt2) gRNA Sequence

<400> SEQUENCE: 125
aatctccccc acccttaaga gttttagagc tagaaatagc aagttaaaat aaggctagtc    60
```

```
cgttatcaac ttgaaaaagt ggcaccgagt cggtgc                                    96
```

```
<210> SEQ ID NO 126
<211> LENGTH: 96
<212> TYPE: DNA
<213> ORGANISM: Artificial Sequence
<220> FEATURE:
<223> OTHER INFORMATION: CCR5 gRNA Sequence

<400> SEQUENCE: 126
tgacatcaat tattatacat gttttagagc tagaaatagc aagttaaaat aaggctagtc          60
cgttatcaac ttgaaaaagt ggcaccgagt cggtgc                                    96
```

```
<210> SEQ ID NO 127
<211> LENGTH: 96
<212> TYPE: DNA
<213> ORGANISM: Artificial Sequence
<220> FEATURE:
<223> OTHER INFORMATION: HPRT1 gRNA Sequence

<400> SEQUENCE: 127
gcatttctca gtcctaaaca gttttagagc tagaaatagc aagttaaaat aaggctagtc          60
cgttatcaac ttgaaaaagt ggcaccgagt cggtgc                                    96
```

```
<210> SEQ ID NO 128
<211> LENGTH: 96
<212> TYPE: DNA
<213> ORGANISM: Artificial Sequence
<220> FEATURE:
<223> OTHER INFORMATION: NT (1) gRNA Sequence

<400> SEQUENCE: 128
gggtaaccgt gcggtcgtac gttttagagc tagaaatagc aagttaaaat aaggctagtc          60
cgttatcaac ttgaaaaagt ggcaccgagt cggtgc                                    96
```

```
<210> SEQ ID NO 129
<211> LENGTH: 86
<212> TYPE: DNA
<213> ORGANISM: Artificial Sequence
<220> FEATURE:
<223> OTHER INFORMATION: NT (2) gRNA Sequence

<400> SEQUENCE: 129
gggtaaccgt gttttagagc tagaaatagc aagttaaaat aaggctagtc cgttatcaac          60
ttgaaaaagt ggcaccgagt cggtgc                                               86
```

```
<210> SEQ ID NO 130
<211> LENGTH: 81
<212> TYPE: DNA
<213> ORGANISM: Artificial Sequence
<220> FEATURE:
<223> OTHER INFORMATION: NT (3) gRNA Sequence

<400> SEQUENCE: 130
gggtagtttt agagctagaa atagcaagtt aaaataaggc tagtccgtta tcaacttgaa          60
aaagtggcac cgagtcggtg c                                                    81
```

```
<210> SEQ ID NO 131
<211> LENGTH: 249
<212> TYPE: DNA
<213> ORGANISM: Artificial Sequence
<220> FEATURE:
```

<223> OTHER INFORMATION: Promoter Sequence

<400> SEQUENCE: 131

| | |
|---|---|
| gagggcctat ttcccatgat tccttcatat ttgcatatac gatacaaggc tgttagagag | 60 |
| ataattggaa ttaatttgac tgtaaacaca aagatattag tacaaaatac gtgacgtaga | 120 |
| aagtaataat ttcttgggta gtttgcagtt ttaaaattat gttttaaaat ggactatcat | 180 |
| atgcttaccg taacttgaaa gtatttcgat ttcttggctt tatatatctt gtggaaagga | 240 |
| cgaaacacc | 249 |

<210> SEQ ID NO 132
<211> LENGTH: 24
<212> TYPE: RNA
<213> ORGANISM: Artificial Sequence
<220> FEATURE:
<223> OTHER INFORMATION: DHCR7 crRNA

<400> SEQUENCE: 132

| | |
|---|---|
| cacuggcgag cgucaucuuc cuac | 24 |

<210> SEQ ID NO 133
<211> LENGTH: 1431
<212> TYPE: DNA
<213> ORGANISM: Artificial Sequence
<220> FEATURE:
<223> OTHER INFORMATION: DHCR7 dsDNA #1 (1431bp)

<400> SEQUENCE: 133

| | |
|---|---|
| gtaaaacgac ggccagtgaa ttgtaatacg actcactata gggcgaattg ggcccgacgt | 60 |
| cgcatgctcc cggccgccat ggcggccgcg ggaattcgat tgtcccttig gggactgaga | 120 |
| tgctcctttc cagacctggt gcaaggcgtg actcctgctg acaatggggc ttcctcagga | 180 |
| cagcactgcc ctcccacggg gttttgctcc tatcctcagc ttgtccctgc agagctgggc | 240 |
| gtgcccagca actgcatgca ggcatgccgt gaaggtgtat caaacgctga tgtgacaggt | 300 |
| gcctcctgcc ttacagctga ggatgaatct gaacatgtca gagtccaggg aatgccctgc | 360 |
| tgggtcccgg gaacccagat gtcaacctga gccaggatcc atgtcccaga caaatggaag | 420 |
| gactacccca gcaggagggc acgctcccca cctgctgtgt cccaaccccca gggcaggggc | 480 |
| tgctgacctg gaaggtgacc cacaaggtat agagctgggc ggctttcctc gttataggtg | 540 |
| gagtcttggc ccagatgtcc gagagccgag catgtccggt gacgatgtcc accacagggc | 600 |
| cagtcagggc gcagctgtac tggtcacaag ccatgatgaa gtagtagacg atgaagggg | 660 |
| cgaacagcag taggaagatg acgctcgcca gtgaaaacca gtccacctcc ctgcgaggac | 720 |
| ggatgcaggc agtcacactg gggcccatct gccctgggcc ccaccaggac cctaagaggc | 780 |
| tctgtgtggg agaactgttg ctcaaaccca ccagtacccc atgacagaag cattagctc | 840 |
| ctagcacggg ccctccttgc ggccagggaa gccactcaac atgcctgctc tactgtagtt | 900 |
| gattaactgg tggcactatc tgtggccccc atggaaggcc cagagctcag aatatgagcg | 960 |
| gaggtaggtc tttcacaacc accaaggcca gtggtttccc cagttccagg tcggagagga | 1020 |
| tactcaccct gcacgaagtc cccatggttc tatggcgaaa tggagctgt gacaataggt | 1080 |
| cataccccca gatggtggga aggccccagc tgcccttaa gcctttatct tttttctaa | 1140 |
| gttgttgact gaccatgatt tctagtttct ttttataatt ccttacttta taaagtggaa | 1200 |
| aactgtttac ctttcattag tcttgacaaa aaaaaaaaa tcttttttaa aaaggtcctt | 1260 |
| cattcctttg ggtccataca attccaaagg ctggaaagaa tcactagtga attcgcggcc | 1320 |

```
gcctgcaggt cgaccatatg ggagagctcc caacgcgttg gatgcatagc ttgagtattc    1380
tatagtgtca cctaaatagc ttggcgtaat catggtcata gctgtttcct g             1431

<210> SEQ ID NO 134
<211> LENGTH: 544
<212> TYPE: DNA
<213> ORGANISM: Artificial Sequence
<220> FEATURE:
<223> OTHER INFORMATION: DHCR7 dsDNA #2 (544bp)

<400> SEQUENCE: 134
gagccaagct ctccatctag tggacaggga agctagcagc aaaccttccc ttcactacaa      60
aacttcattg cttggccaaa aagagagtta attcaatgta gacatctatg taggcaatta     120
aaaacctatt gatgtataaa acagtttgca ttcatggagg gcaactaaat acattctagg     180
actttataaa agatcacttt ttatttatgc acagggtgga acaagatgga ttatcaagtg     240
tcaagtccaa tctatgacat caattattat acatcggagc cctgccaaaa aatcaatgtg     300
aagcaaatcg cagcccgcct cctgcctccg ctctactcac tggtgttcat ctttggtttt     360
gtgggcaaca tgctggtcat cctcatcctg ataaactgca aaaggctgaa gagcatgact     420
gacatctacc tgctcaacct ggccatctct gacctgtttt tccttcttac tgtccccttc     480
tgggctcact atgctgccgc ccagtgggac tttggaaata caatgtgtca actcttgaca     540
gggc                                                                  544

<210> SEQ ID NO 135
<211> LENGTH: 3825
<212> TYPE: DNA
<213> ORGANISM: Artificial Sequence
<220> FEATURE:
<223> OTHER INFORMATION: Cas12a

<400> SEQUENCE: 135
atgggcaaaa accaaaattt ccaagaattt atcggagtga gcccctgca gaaaaccctc       60 cggaacgagc ttattccgac tgagaccaca aagaaaaata aacccagct ggacttgctg      120 actgaagatg agatccgcgc ccagaaccgg gaaaagctca agagatgat ggacgattat      180 taccgcaatg ttattgacag tacccttcac gtcgggatcg ctgtggattg gtcttatctg     240
ttcagctgca tgcggaacca tttgcgcgaa aattccaagg agtcaaaacg ggaactggag     300
cgcacacagg acagcattcg gagtcagata cacaacaagt tgccgaacg cgcagatttc     360 aaagacatgt ttggcgcctc tatcattacc aagctccttc ctacttacat caaacaaaat     420
agcgagtatt ccgaacggta cgatgagtca atggaaattc tgaagttgta tggtaaattc     480
accacaagcc tgaccgacta ctttgagact cgcaagaaca tattcagtaa agaaaagatc     540
tctagcgctg taggctatcg gattgtggag gaaaatgccg agatctttct ccagaaccag     600
aatgcatacg atcgcatttg taaaatagcc ggacttgacc tgcatgggtt ggataacgaa     660
atcaccgctt atgttgacgg caagacactg aaagaggtct gctccgatga aggtttcgcc     720
aaggcaatta cccaagaggg catcgatcgg tacaatgaag ccattggagc tgtgaaccag     780
tatatgaatc tcctttgtca gaaaacaag gccctgaaac ccgggcaatt aagatgaaa     840 cgcttgcaca gcagatact gtgcaaaggc actacctcat tcgatatccc gaagaaattt     900
gagaatgaca gcaggtata cgatgcagtg aacagcttca cagaaattgt taccaaaaat     960
aacgacctca gcggcttct gaatatcact caaaacgcca atgattatga catgaacaaa    1020
```

```
atttacgtcg tggctgatgc ctatagtatg atatctcagt ttatcagcaa gaaatggaat    1080
ttgattgagg aatgtctgct cgactactat tccgataacc ttccaggtaa gggcaatgca    1140
aaagagaaca aggtaaaaaa ggccgtgaaa gaagagacct accgctcagt tagccagctg    1200
aatgaagtca tcgagaagta ttacgtggaa aaacaggac aaagtgtatg gaaggtggag     1260
tcttatatta gctccttggc tgaaatgata aaactggagc tctgccatga aatcgacaac    1320
gatgagaagc acaatcttat tgaggacgat gagaaaatct cagaaattaa ggagctgttg    1380
gacatgtaca tggatgtttt ccatataatc aaagtctttc gggtgaacga agtactgaat    1440
ttcgacgaga cctttttatag cgaaatggat gagatttacc aggacatgca ggaaatcgtg    1500
cccctctata accacgttcg caattacgtc actcaaaagc cgtataaaca ggagaagtac    1560
cggctttatt tccatacccc tacactggcc aacgggtgga gtaaatctaa ggaatacgat    1620
aataacgcaa ttatattggt gcgcgaggac aaatattacc tgggcatcct caatgccaag    1680
aaaaagccca gcaaagaaat tatggctggt aaggaggatt gttccgaaca cgcctatgca    1740
aaaatgaact actatcttct gccgggcgcc aataagatgt tgccaaaagt atttctgtca    1800
aagaaaggaa tccaggacta ccatcccagc agttatattg tggaggggta caacgaaaag    1860
aaacacataa agggctctaa aaatttcgat atccggtttt gccgcgacct cattgattat    1920
ttcaaggagt gtatcaaaaa gcatccggac tggaacaaat ttaatttcga atttagcgct    1980
accgagactt acgaagatat ttccgttttc tatcgggagg tcgaaaagca aggttaccgc    2040
gtggagtgga cctatataaa ctcagaggac atccagaaac ttgaggaaga tggccagctg    2100 ttttttgttcc aaatttacaa taaggacttt gccgtaggaa gcacagggaa acctaacctg    2160
cacaccctct atcttaagaa tctgttcagt gaggaaaact gcgggatat cgtgctgaaa     2220 ctcaatggcg aggcagaaat ttttttccgc aagtctagcg ttcagaaacc cgtcatacat    2280
aagtgcggtt ccatccttgt gaaccggact tacgagatta ccgaatcagg cacaacccgc    2340
gtacagagca tcccggagag tgaatatatg gagctgtatc ggtattttaa ttctgaaaaa    2400
caaattgagt tgagcgacga agccaagaaa tacctggata aggtgcagtg taacaaagct    2460
aagactgaca tagttaaaga ttatcgctac accatggaca agttctttat ccacctccca    2520
attacaatca atttcaaagt cgataaggga aacaatgtga acgccattgc acagcaatat    2580
atagccgggc ggaaagacct tcatgtaatc ggcattgatc gcggtgagcg gaatctgatc    2640
tacgtgtccg ttattgacat gtatggccgc atattggaac agaagtcatt taacctggtc    2700
gagcaggtga gcagtcaagg aaccaaacgg tactatgatt acaaggaaaa actccagaat    2760
cgcgaggaag agcgggacaa ggctcgccag tcttggaaaa ctatcgggaa gattaaagaa    2820
cttaaggagg gctatctgag ctccgtaatc cacgaaattg cccaaatggt ggttaaatac    2880
aacgcaataa tcgccatgga ggatttgaat tatggtttca gcggggccg ctttaaagtc     2940 gaacggcagg tgtaccagaa gttcgagacc atgctgattt caaaactcaa ctatcttgct    3000
gacaagagcc aagccgtaga tgaacccgga gggattctgc gcggctacca gatgacatat    3060
gtgccggaca atattaaaaa cgttggtcgg cagtgcggca ataatctttta cgtccctgca    3120 gcctatacca gtaagattga tcccactacc ggattcatca atgcttttaa acgcgacgtg    3180
gtatctacaa acgatgccaa ggagaatttc ttgatgaaat ttgacagcat tcaatacgat    3240
atagaaaagg ggctgttcaa atttttccttc gactataaga actttgcaac ccataaactc    3300
actcttgcca agaccaaatg ggatgtgtac acaaatggca cccggattca gaacatgaag    3360
gttgagggtc actggctgtc aatggaagtc gagttgacta ccaaaatgaa ggaactgctc    3420
```

```
gacgatagcc atattccgta tgaggaaggc cagaatatcc ttgacgatct gcgcgagatg    3480
aaagacatta caaccatagt gaacggaatc ttggaaattt tctggctgac tgtacaactc    3540
cggaatagtc gcatcgataa cccagactac gatcggatta tatctcccgt gcttaataag    3600
aacggggagt ttttcgacag cgatgaatat aattcctaca tcgacgctca gaaagccccg    3660
ctgcctattg atgcagacgc caacggcgct ttttgtatcg ccttgaaggg tatgtatacc    3720
gcaaatcaga ttaaagagaa ctgggttgaa ggcgagaagc tgcccgccga ttgcctcaaa    3780
atagaacacg cttcatggct tgccttcatg caaggagagc gcggg                    3825
```

<210> SEQ ID NO 136
<211> LENGTH: 1275
<212> TYPE: PRT
<213> ORGANISM: Artificial Sequence
<220> FEATURE:
<223> OTHER INFORMATION: Cas12a

<400> SEQUENCE: 136

```
Met Gly Lys Asn Gln Asn Phe Gln Glu Phe Ile Gly Val Ser Pro Leu
 1               5                  10                  15

Gln Lys Thr Leu Arg Asn Glu Leu Ile Pro Thr Glu Thr Thr Lys Lys
            20                  25                  30

Asn Ile Thr Gln Leu Asp Leu Leu Thr Glu Asp Glu Ile Arg Ala Gln
        35                  40                  45

Asn Arg Glu Lys Leu Lys Glu Met Met Asp Asp Tyr Tyr Arg Asn Val
    50                  55                  60

Ile Asp Ser Thr Leu His Val Gly Ile Ala Val Asp Trp Ser Tyr Leu
65                  70                  75                  80

Phe Ser Cys Met Arg Asn His Leu Arg Glu Asn Ser Lys Glu Ser Lys
                85                  90                  95

Arg Glu Leu Glu Arg Thr Gln Asp Ser Ile Arg Ser Gln Ile His Asn
            100                 105                 110

Lys Phe Ala Glu Arg Ala Asp Phe Lys Asp Met Phe Gly Ala Ser Ile
        115                 120                 125

Ile Thr Lys Leu Leu Pro Thr Tyr Ile Lys Gln Asn Ser Glu Tyr Ser
    130                 135                 140

Glu Arg Tyr Asp Glu Ser Met Glu Ile Leu Lys Leu Tyr Gly Lys Phe
145                 150                 155                 160

Thr Thr Ser Leu Thr Asp Tyr Phe Glu Thr Arg Lys Asn Ile Phe Ser
                165                 170                 175

Lys Glu Lys Ile Ser Ser Ala Val Gly Tyr Arg Ile Val Glu Glu Asn
            180                 185                 190

Ala Glu Ile Phe Leu Gln Asn Gln Asn Ala Tyr Asp Arg Ile Cys Lys
        195                 200                 205

Ile Ala Gly Leu Asp Leu His Gly Leu Asp Asn Glu Ile Thr Ala Tyr
    210                 215                 220

Val Asp Gly Lys Thr Leu Lys Glu Val Cys Ser Asp Glu Gly Phe Ala
225                 230                 235                 240

Lys Ala Ile Thr Gln Glu Gly Ile Asp Arg Tyr Asn Glu Ala Ile Gly
                245                 250                 255

Ala Val Asn Gln Tyr Met Asn Leu Leu Cys Gln Lys Asn Lys Ala Leu
            260                 265                 270

Lys Pro Gly Gln Phe Lys Met Lys Arg Leu His Lys Gln Ile Leu Cys
        275                 280                 285
```

-continued

```
Lys Gly Thr Thr Ser Phe Asp Ile Pro Lys Lys Phe Glu Asn Asp Lys
290                 295                 300

Gln Val Tyr Asp Ala Val Asn Ser Phe Thr Glu Ile Val Thr Lys Asn
305                 310                 315                 320

Asn Asp Leu Lys Arg Leu Leu Asn Ile Thr Gln Asn Ala Asn Asp Tyr
            325                 330                 335

Asp Met Asn Lys Ile Tyr Val Val Ala Asp Ala Tyr Ser Met Ile Ser
        340                 345                 350

Gln Phe Ile Ser Lys Lys Trp Asn Leu Ile Glu Glu Cys Leu Leu Asp
            355                 360                 365

Tyr Tyr Ser Asp Asn Leu Pro Gly Lys Gly Asn Ala Lys Glu Asn Lys
370                 375                 380

Val Lys Lys Ala Val Lys Glu Glu Thr Tyr Arg Ser Val Ser Gln Leu
385                 390                 395                 400

Asn Glu Val Ile Glu Lys Tyr Val Glu Lys Thr Gly Gln Ser Val
                405                 410                 415

Trp Lys Val Glu Ser Tyr Ile Ser Ser Leu Ala Glu Met Ile Lys Leu
            420                 425                 430

Glu Leu Cys His Glu Ile Asp Asn Asp Glu Lys His Asn Leu Ile Glu
            435                 440                 445

Asp Asp Glu Lys Ile Ser Glu Ile Lys Glu Leu Leu Asp Met Tyr Met
450                 455                 460

Asp Val Phe His Ile Ile Lys Val Phe Arg Val Asn Glu Val Leu Asn
465                 470                 475                 480

Phe Asp Glu Thr Phe Tyr Ser Glu Met Asp Glu Ile Tyr Gln Asp Met
            485                 490                 495

Gln Glu Ile Val Pro Leu Tyr Asn His Val Arg Asn Tyr Val Thr Gln
            500                 505                 510

Lys Pro Tyr Lys Gln Glu Lys Tyr Arg Leu Tyr Phe His Thr Pro Thr
        515                 520                 525

Leu Ala Asn Gly Trp Ser Lys Ser Lys Glu Tyr Asp Asn Asn Ala Ile
530                 535                 540

Ile Leu Val Arg Glu Asp Lys Tyr Tyr Leu Gly Ile Leu Asn Ala Lys
545                 550                 555                 560

Lys Lys Pro Ser Lys Glu Ile Met Ala Gly Lys Glu Asp Cys Ser Glu
            565                 570                 575

His Ala Tyr Ala Lys Met Asn Tyr Tyr Leu Leu Pro Gly Ala Asn Lys
            580                 585                 590

Met Leu Pro Lys Val Phe Leu Ser Lys Lys Gly Ile Gln Asp Tyr His
        595                 600                 605

Pro Ser Ser Tyr Ile Val Glu Gly Tyr Asn Glu Lys Lys His Ile Lys
610                 615                 620

Gly Ser Lys Asn Phe Asp Ile Arg Phe Cys Arg Asp Leu Ile Asp Tyr
625                 630                 635                 640

Phe Lys Glu Cys Ile Lys Lys His Pro Asp Trp Asn Lys Phe Asn Phe
            645                 650                 655

Glu Phe Ser Ala Thr Glu Thr Tyr Glu Asp Ile Ser Val Phe Tyr Arg
            660                 665                 670

Glu Val Glu Lys Gln Gly Tyr Arg Val Glu Trp Thr Tyr Ile Asn Ser
        675                 680                 685

Glu Asp Ile Gln Lys Leu Glu Glu Asp Gly Gln Leu Phe Leu Phe Gln
690                 695                 700

Ile Tyr Asn Lys Asp Phe Ala Val Gly Ser Thr Gly Lys Pro Asn Leu
```

```
            705                 710                 715                 720
His Thr Leu Tyr Leu Lys Asn Leu Phe Ser Glu Glu Asn Leu Arg Asp
                725                 730                 735

Ile Val Leu Lys Leu Asn Gly Glu Ala Glu Ile Phe Arg Lys Ser
                740                 745                 750

Ser Val Gln Lys Pro Val Ile His Lys Cys Gly Ser Ile Leu Val Asn
                755                 760                 765

Arg Thr Tyr Glu Ile Thr Glu Ser Gly Thr Thr Arg Val Gln Ser Ile
                770                 775                 780

Pro Glu Ser Glu Tyr Met Glu Leu Tyr Arg Tyr Phe Asn Ser Glu Lys
785                 790                 795                 800

Gln Ile Glu Leu Ser Asp Glu Ala Lys Lys Tyr Leu Asp Lys Val Gln
                805                 810                 815

Cys Asn Lys Ala Lys Thr Asp Ile Val Lys Asp Tyr Arg Tyr Thr Met
                820                 825                 830

Asp Lys Phe Phe Ile His Leu Pro Ile Thr Ile Asn Phe Lys Val Asp
                835                 840                 845

Lys Gly Asn Asn Val Asn Ala Ile Ala Gln Gln Tyr Ile Ala Gly Arg
                850                 855                 860

Lys Asp Leu His Val Ile Gly Ile Asp Arg Gly Glu Arg Asn Leu Ile
865                 870                 875                 880

Tyr Val Ser Val Ile Asp Met Tyr Gly Arg Ile Leu Glu Gln Lys Ser
                885                 890                 895

Phe Asn Leu Val Glu Gln Val Ser Ser Gln Gly Thr Lys Arg Tyr Tyr
                900                 905                 910

Asp Tyr Lys Glu Lys Leu Gln Asn Arg Glu Glu Arg Asp Lys Ala
                915                 920                 925

Arg Gln Ser Trp Lys Thr Ile Gly Lys Ile Lys Glu Leu Lys Glu Gly
                930                 935                 940

Tyr Leu Ser Ser Val Ile His Glu Ile Ala Gln Met Val Val Lys Tyr
945                 950                 955                 960

Asn Ala Ile Ile Ala Met Glu Asp Leu Asn Tyr Gly Phe Lys Arg Gly
                965                 970                 975

Arg Phe Lys Val Glu Arg Gln Val Tyr Gln Lys Phe Glu Thr Met Leu
                980                 985                 990

Ile Ser Lys Leu Asn Tyr Leu Ala Asp Lys Ser Gln Ala Val Asp Glu
                995                 1000                1005

Pro Gly Gly Ile Leu Arg Gly Tyr Gln Met Thr Tyr Val Pro Asp Asn
                1010                1015                1020

Ile Lys Asn Val Gly Arg Gln Cys Gly Ile Ile Phe Tyr Val Pro Ala
1025                1030                1035                1040

Ala Tyr Thr Ser Lys Ile Asp Pro Thr Thr Gly Phe Ile Asn Ala Phe
                1045                1050                1055

Lys Arg Asp Val Val Ser Thr Asn Asp Ala Lys Glu Asn Phe Leu Met
                1060                1065                1070

Lys Phe Asp Ser Ile Gln Tyr Asp Ile Glu Lys Gly Leu Phe Lys Phe
                1075                1080                1085

Ser Phe Asp Tyr Lys Asn Phe Ala Thr His Lys Leu Thr Leu Ala Lys
                1090                1095                1100

Thr Lys Trp Asp Val Tyr Thr Asn Gly Thr Arg Ile Gln Asn Met Lys
1105                1110                1115                1120

Val Glu Gly His Trp Leu Ser Met Glu Val Glu Leu Thr Thr Lys Met
                1125                1130                1135
```

```
Lys Glu Leu Leu Asp Asp Ser His Ile Pro Tyr Glu Gly Gln Asn
            1140                1145                1150

Ile Leu Asp Asp Leu Arg Glu Met Lys Asp Ile Thr Thr Ile Val Asn
        1155                1160                1165

Gly Ile Leu Glu Ile Phe Trp Leu Thr Val Gln Leu Arg Asn Ser Arg
    1170                1175                1180

Ile Asp Asn Pro Asp Tyr Asp Arg Ile Ile Ser Pro Val Leu Asn Lys
1185                1190                1195                1200

Asn Gly Glu Phe Phe Asp Ser Asp Glu Tyr Asn Ser Tyr Ile Asp Ala
            1205                1210                1215

Gln Lys Ala Pro Leu Pro Ile Asp Ala Asp Ala Asn Gly Ala Phe Cys
            1220                1225                1230

Ile Ala Leu Lys Gly Met Tyr Thr Ala Asn Gln Ile Lys Glu Asn Trp
            1235                1240                1245

Val Glu Gly Glu Lys Leu Pro Ala Asp Cys Leu Lys Ile Glu His Ala
        1250                1255                1260

Ser Trp Leu Ala Phe Met Gln Gly Glu Arg Gly
1265                1270                1275

<210> SEQ ID NO 137
<211> LENGTH: 24
<212> TYPE: RNA
<213> ORGANISM: Artificial Sequence
<220> FEATURE:
<223> OTHER INFORMATION: EGFR_WT crRNA

<400> SEQUENCE: 137
ggagauguug cuucucuuaa uucc                                          24

<210> SEQ ID NO 138
<211> LENGTH: 24
<212> TYPE: RNA
<213> ORGANISM: Artificial Sequence
<220> FEATURE:
<223> OTHER INFORMATION: CCR5 crRNA

<400> SEQUENCE: 138
ugcacagggu ggaacaagau ggau                                          24

<210> SEQ ID NO 139
<211> LENGTH: 24
<212> TYPE: RNA
<213> ORGANISM: Artificial Sequence
<220> FEATURE:
<223> OTHER INFORMATION: EGFR_E2 crRNA

<400> SEQUENCE: 139
ggagaugucu ugauagcgac ggga                                          24
```